(12) United States Patent
Izsvak et al.

(10) Patent No.: US 9,840,696 B2
(45) Date of Patent: Dec. 12, 2017

(54) NUCLEIC ACIDS ENCODING SB10 VARIANTS

(71) Applicants: Zsuzsanna Izsvak, Berlin (DE); Zoltan Ivics, Berlin (DE); Lajos Mates, Berlin (DE); Namitha Manoj, Boulder, CO (US); Carmen-Anisia Judis, Berlin (DE); Andrea Katzer, Wandlitz (DE)

(72) Inventors: Zsuzsanna Izsvak, Berlin (DE); Zoltan Ivics, Berlin (DE); Lajos Mates, Berlin (DE); Namitha Manoj, Boulder, CO (US); Carmen-Anisia Judis, Berlin (DE); Andrea Katzer, Wandlitz (DE)

(73) Assignee: Max-Delbruck-Centrum Fur Molekulare Medizin, Berlin (DE)

( * ) Notice: Subject to any disclaimer, the term of this patent is extended or adjusted under 35 U.S.C. 154(b) by 0 days.

(21) Appl. No.: 14/957,877

(22) Filed: Dec. 3, 2015

(65) Prior Publication Data
US 2016/0264949 A1  Sep. 15, 2016

Related U.S. Application Data

(62) Division of application No. 12/667,527, filed as application No. PCT/EP2008/005342 on Jun. 30, 2008, now Pat. No. 9,228,180.

(30) Foreign Application Priority Data

Jul. 4, 2007  (EP) ..................... 07013109
Aug. 17, 2007 (EP) ..................... 07016202

(51) Int. Cl.
| | |
|---|---|
| A61K 38/00 | (2006.01) |
| C12N 9/12 | (2006.01) |
| C12N 9/22 | (2006.01) |
| C12N 15/90 | (2006.01) |
| A61K 38/45 | (2006.01) |
| A61K 48/00 | (2006.01) |

(52) U.S. Cl.
CPC ............ *C12N 9/1241* (2013.01); *A61K 38/45* (2013.01); *A61K 48/0066* (2013.01); *C12N 9/22* (2013.01); *C12N 15/90* (2013.01); *A61K 48/00* (2013.01); *C12N 2800/90* (2013.01); *C12Y 207/07* (2013.01)

(58) Field of Classification Search
None
See application file for complete search history.

(56) References Cited

U.S. PATENT DOCUMENTS

| | | | |
|---|---|---|---|
| 5,620,896 A | 4/1997 | Herrmann et al. | |
| 6,489,458 B2 | 12/2002 | Hackett et al. | |
| 6,613,752 B2 | 9/2003 | Kay et al. | |
| 9,228,180 B2* | 1/2016 | Izsvak ..................... | C12N 9/22 |
| 2002/0016975 A1 | 2/2002 | Hacket et al. | |
| 2005/0003542 A1 | 1/2005 | Kay et al. | |
| 2005/0112764 A1 | 5/2005 | Ivics et al. | |
| 2006/0252140 A1 | 11/2006 | Yant et al. | |
| 2011/0117072 A1* | 5/2011 | Izsvak ..................... | C12N 15/90 |
| | | | 424/94.5 |

FOREIGN PATENT DOCUMENTS

| | | |
|---|---|---|
| WO | WO98/40510 | 9/1998 |
| WO | WO99/25817 | 5/1999 |
| WO | 00/68399 | 11/2000 |
| WO | WO01/81565 | 11/2001 |
| WO | 2009/003671 | 1/2009 |

OTHER PUBLICATIONS

West, Biochemistry, vol. 29, pp. 8509-8517, 1990.*
Yant et al. (Nucleic Acid Research, vol. 35, No. 7, Mar. 7, 2007, pp. 1-13.*
Wells, Biochemistry, "Additivity of mutational effects in proteins," 1990; 29(37): 8509-17.
Yant, et al., Nucleic Acids Research, "Site-directed transposon integration in human cells," 2007; 35(7): e50.
Anderson W.F., Human Gene Therapy, Nature, Apr. 30, 1998; 25-30 392(6679 Suppl) Review.
Ivics Z. et al., Molecular Reconstruction of Sleeping Beauty, a TC1-like Transposon from Fish and Its Transposition in Human Cells, Cell, Nov. 14, 1997, 501-510, 91(4).
Izsvak Z. et al., Sleeping Beauty, A Wide Host-Range Transposon Vector for Genetic Transformation in Vertebrates, J. Mol. Biol., Sep. 8, 2000; 93-102, 302(1).
Luo G. et al., Chromosomal Transposition of a Tc1/mariner-like element in Mouse Embyonic Stem Cells, Proc Natl Acad Sci USA. Sep. 1, 1998; 10769-10773, 95(18).
Nicolau C. et al., In Vivo Expression of Rat Insulin After Intravenous Administration of the Liposome-entrapped Gene for Rat Insulin 1, Prc Natl Acad Sci USA, Feb. 1983; 1068-1072, 80(4).
Plasterk R.H. et al., Resident Aliens: the Tc1/Mariner Superfamily of Transposable Elements, Trends Genet., Aug. 1999; 326-332, 15(8).

(Continued)

Primary Examiner — Hope Robinson
(74) Attorney, Agent, or Firm — Klauber & Jackson LLC

(57) ABSTRACT

The present invention refers to hyperactive variants of a transposase of the transposon system Sleeping Beauty (SB). The invention further refers to corresponding nucleic acids producing these variants, to a gene transfer system for stably introducing nucleic acid(s) into the DNA of a cell by using these hyperactive variants of a transposase of the transposon system Sleeping Beauty (SB) and to transposons used in the inventive gene transfer system, comprising a nucleic acid sequence with flanking repeats (IRs and/or RSDs). Furthermore, applications of these transposase variants, the transposon, or the gene transfer system are also disclosed such as gene therapy, insertional mutagenesis, gene discovery (including genome mapping), mobilization of genes, library screening, or functional analysis of genomes in vivo and in vitro. Finally, pharmaceutical compositions and kits are also encompassed.

19 Claims, 28 Drawing Sheets

(56) References Cited

OTHER PUBLICATIONS

Verma I.M. et al., Gene Therapy—Promises, Problems, and Prospects, Nature, Sep. 18, 1997; 239-242; 389(6648).
Yant S.R. et al., Somatic Integration and Long-Term Transgene Expression in Normal and Haemophilic Mice Using a DNA Transposon System, Nat. Genet, May 2000, 35-41; 25(1).
Baus et al., "Hyperactive Transposase Mutants of the Sleeping Beauty Transposon", Molecular Therapy, vol. 12, No. 6 (2005), pp. 1148-1156.
Zayed et al., "Development of Hyperactive Sleeping Beauty Transposon Vectors by Mutational Analysis", Molecular Therapy, vol. 9, No. 2 (2004), pp. 292-304.
Yant et al., "Mutational Analysis of the N-Terminal DNA-Binding Domain of Sleeping Beauty Transposase: Critical Residues for DNA Binding and Hyperactivity in Mammalian Cells", Molecular and Cellular Biology, vol. 24, No. 20 (2004), pp. 9239-9247.
Geurts et al., "Gene Transfer into Genomes of Human Cells by the Sleeping Beauty Transposon System", Molecular Therapy, vol. 8, No. 1 (2003), pp. 108-117.

* cited by examiner

| Restriction fragments | Mutations |
|---|---|
| Group1 (5x) 114bp CDS and 130bp flanking | K13A |
| | K13D |
| | K14R |
| | K30R |
| | K33A |
| | T51N |
| | T52V |
| | L64A |
| | E69A |
| | L72A |
| Group2 (12x) 298bp CDS | T83A |
| | L91A |
| | G95A |
| | I100L |
| | N111G |
| | R115H |
| | N125K |
| Alone | T136R |
| | R143L |
| | R147E |
| | H187Y |
| | G189A |
| | AA199SS |
| Group3 (10x) 273bp CDS | T203V |
| | A205K |
| | KVRE 205,7,8,10 |
| | DAVQ 214-17 |
| | N217H |
| | M243H |
| | M243Q |
| | V253L |
| | VVA253HVR |
| | K262R |
| | E267D |
| Group4 (13x) 335bp CDS and 215bp flanking | S270A |
| | A283R |
| | R288A |
| | L303F |
| | H312P |
| | T314N |
| | G317E |
| Prediction: | |
| ~4 mutation/clone | |
| Found: | |
| 2,2 mutation/clone | |

Fig. 4

A 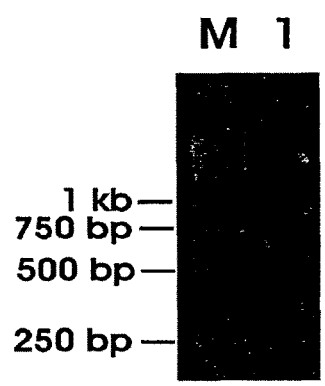 B 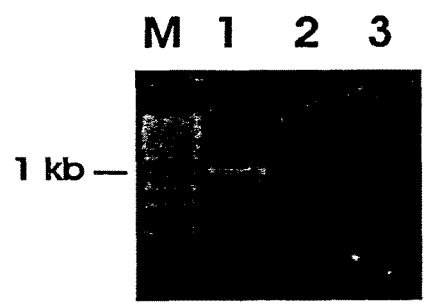
Fig. 6

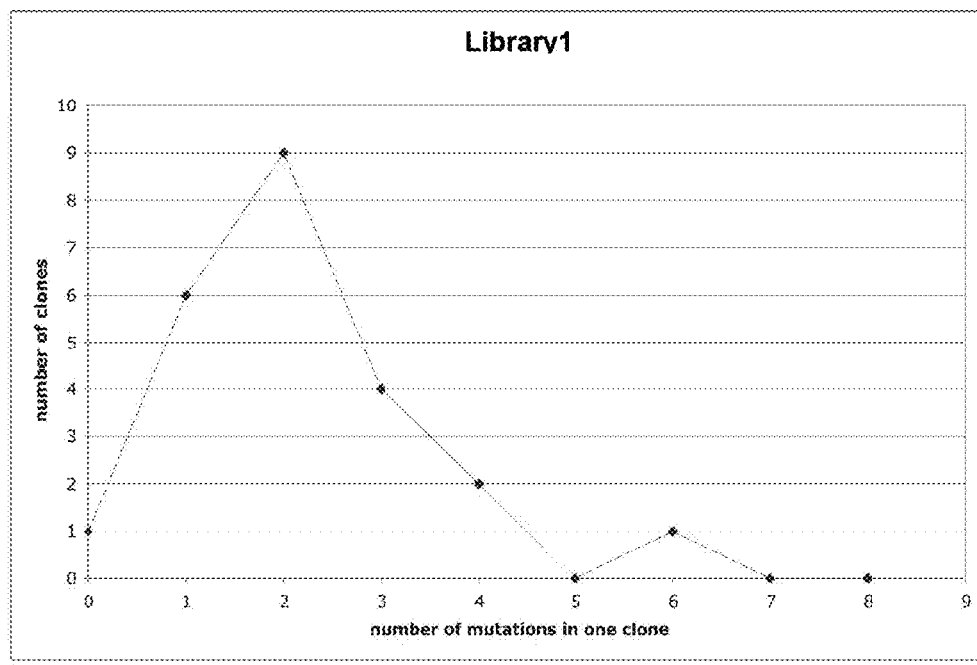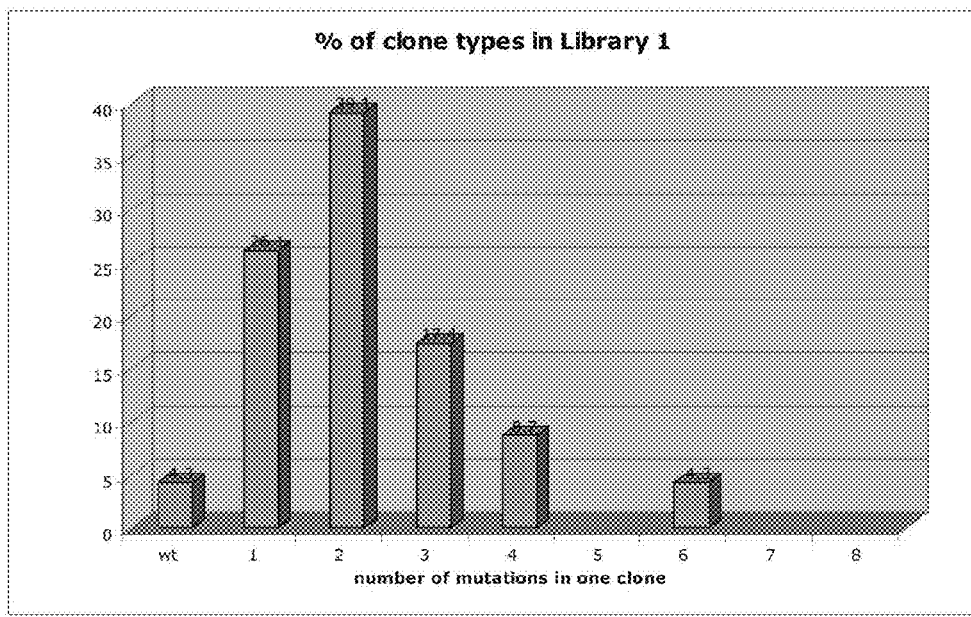
Fig. 7

A

| Position on plate: | 2G6 | 3D5 | 6A5 | 6G2 | 8B4 | 12D10 | 13H3 |
|---|---|---|---|---|---|---|---|
| | | | | | K13D | K13A | |
| | K14R | | K14R | K14R | | | |
| | | | K30R | | | | |
| | | K33A | | | K33A | K33A | K33A |
| | | | | | T83A | | T83A |
| | | R115H | | | | | |
| | | | 205KVRE | | 207VRE | | |
| | 214DAVQ | 214DAVQ | 214DAVQ | 214DAVQ | | 214DAVQ | 214DAVQ |
| | | M243H | M243H | | M243Q | | |
| | | | | | | | G317E |
| | 2 mutations | 4 mutations | 5 mutations | 2 mutations | 5 mutations | 3 mutations | 4 mutations |

B

| | mutations/clone | Incidence of 214DAVQ |
|---|---|---|
| Best 7 clones | 3,6 | 85% |
| Next 31 clones | 3 | 38% |

Fig. 8

LIBRARY

| 3D5 | 6A5 | S28L |
|---|---|---|
| | K1/R | K1/R |
| N23A | K30R | |
| R115H | | T63A |
| 214DAYQ | 209KYRE | |
| N243H | 216DAYQ | |
| | N243H | M243Q |
| 4 mutations | 5 mutations | 3 mutations |
| 30X | 30X | 15X |

ADDITIONAL MUTATIONS FROM THE SEQUENCED HYPERACTIVES

| |
|---|
| T10L |
| R14QL |
| R147E |
| E267D |
| T314N |
| G317E |

SEQ1

```
  1   MGKSKEISQD LRKKIVDLHK SGSSLGAISK RLKVPRSSVQ TIVRKYKHHG
 51   TTQPSYRSGR RRVLSPRDER TLVRKVQINP RTTAKDLVKM LEETGTKVSI
101   STVKRVLYRH NLKGRSARKK PLLQNRHKKA RLRFATAHGD KDRTFWRNVL
151   WSDETKIELF GHNDHRYVWR KKGEACKPKN TIPTVKHGGG SIMLWGCFAA
201   GGTGALHKID GIMRKENYVD ILKQHLKTSV RKLKLGRKWV FQMDNDPKHT
251   SKVVAKWLKD NKVKVLEWPS QSPDLNPIEN LWAELKKRVR ARRPTNLTQL
301   HQLCQEEWAK IHPTYCGKLV EGYPKRLTQV KQFKGNATKY *
```

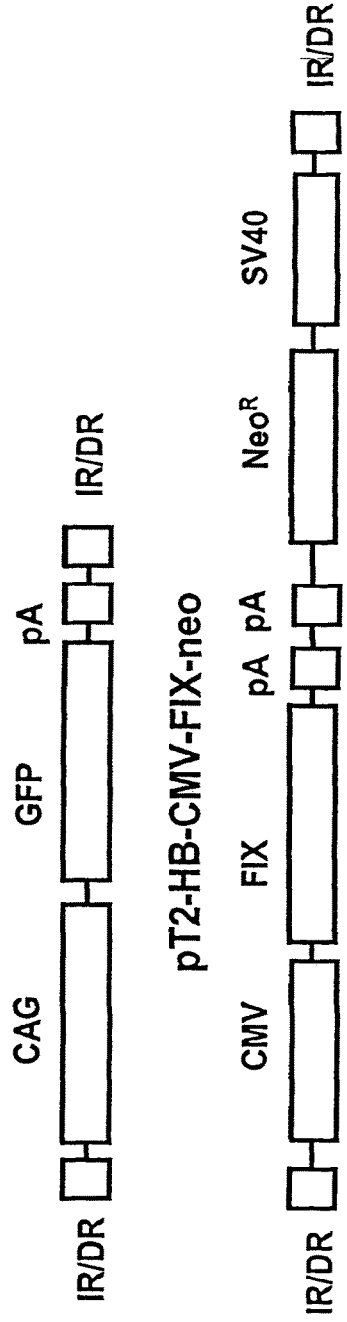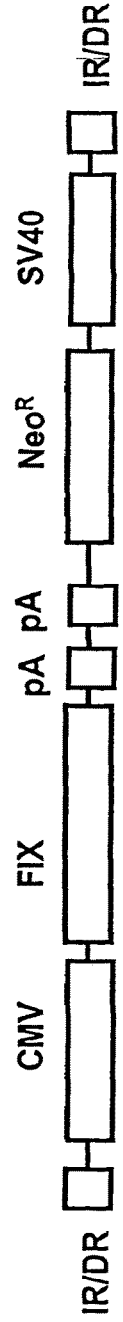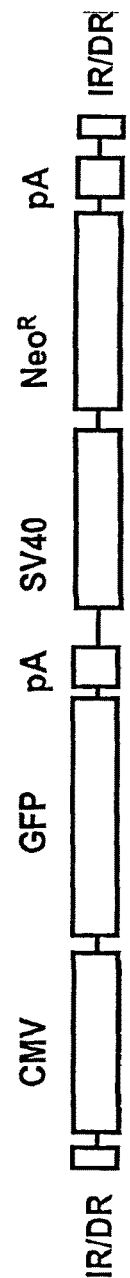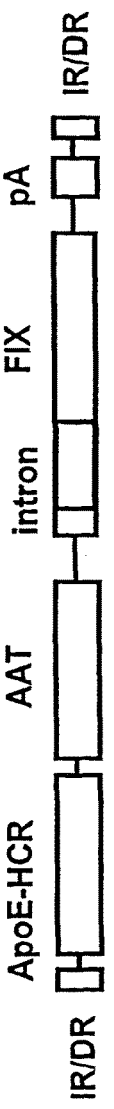
Fig. 11

NUCLEIC ACIDS ENCODING SB10 VARIANTS

CROSS REFERENCE TO RELATED APPLICATIONS

The present application is a division of U.S. Ser. No. 12/667,527, filed Jun. 28, 2010, now U.S. Pat. No. 9,228,180, which is National Stage Application claiming the priority of co-pending PCT Application No. PCT/EP2008/005342 filed Jun. 30, 2008 which in turn claims the benefit of priority to European Application No. 07013109.9, filed Jul. 4, 2007 and European Application No. 07016202.9, filed Aug. 17, 2007. Applicants claim the benefits of both 35 U.S.C. §119 and 35 U.S.C. §120 as to the PCT application, and the entire disclosures of all of the referenced applications are incorporated herein by reference in their entireties.

The present invention refers to hyperactive variants of a transposase of the transposon system Sleeping Beauty (SB). The invention further refers to corresponding nucleic acids producing these variants, to a gene transfer system for stably introducing nucleic acid(s) into the DNA of a cell by using these hyperactive variants of a transposase of the transposon system Sleeping Beauty (SB) and to transposons used in the inventive gene transfer system, comprising a nucleic acid sequence with flanking repeats (IRs and/or RSDs). Furthermore, applications of these transposase variants or the gene transfer system are also disclosed such as gene therapy, insertional mutagenesis, gene discovery (including genome mapping), mobilization of genes, library screening, or functional analysis of genomes in vivo and in vitro. Finally, pharmaceutical compositions and kits are also encompassed.

In the era of functional genomics, there is a sore need for developing efficient means to explore the roles of genes in different cellular functions and, if necessary, to provide effective means for adequately modulating these genes in vitro and in vivo. Such methods, apart from others, particularly comprise methods for introducing DNA into a cell.

Typical methods for introducing DNA into a cell include DNA condensing reagents such as calcium phosphate, polyethylene glycol, and the like, lipid-containing reagents, such as liposomes, multi-lamellar vesicles, and the like, as well as virus-mediated strategies. However, all of these methods have their limitations. For example, there are size constraints associated with DNA condensing reagents and virus-mediated strategies. Further, the amount of nucleic acid that can be transfected into a cell is limited in virus strategies. Not all methods facilitate insertion of the delivered nucleic acid into cellular nucleic acid and while DNA condensing methods and lipid-containing reagents are relatively easy to prepare, the insertion of nucleic acid into viral vectors can be labor intensive. Moreover, virus-mediated strategies can be cell-type or tissue-type specific and the use of virus-mediated strategies can create immunologic problems when used in vivo.

One suitable tool in order to overcome these problems are transposons. Transposons or transposable elements include a (short) nucleic acid sequence with terminal repeat sequences upstream and downstream thereof. Active transposons encode enzymes that facilitate the excision and insertion of the nucleic acid into target DNA sequences.

At present, two classes of transposons are known, i.e. class I and class II transposons.

Class I transposons, also called retrotransposons or retroposons, include retroviral-like retrotransposons and non-retroviral-like retrotransposons. They work by copying themselves and pasting copies back into the genome in multiple places. Initially, retrotransposons copy themselves to RNA (transcription) but, instead of being translated, the RNA is copied into DNA by a reverse transcriptase (often coded by the transposon itself) and inserted back into the genome. Typical representatives of class I transposons include e.g. Copia (*Drosophila*), Ty1 (yeast), THE-1 (human), Bs1 (maize), the F-element, L1 (human) or Cin4 (maize).

As a first step Class II transposons have to be transfected to the cells using standard methods like virus infection etc. Following that Class II transposons, also called "DNA-only transposons", move by a cut and paste mechanism, rather than by copy and paste, and use the transposase enzyme in this mechanism. Different types of transposases may work in different ways. Some can bind to any part of the DNA molecule, and the target site can be located at any position, while others bind to specific sequences. The transposase then cuts the target site to produce sticky ends, releases the transposon and ligates it into the target site. Typical class II representatives include the P element (*Drosophila*), Ac-Ds (maize), TN3 and IS1 (*E. coli*), Tam3 (snapdragon) etc.

Particularly, with class II transposons, the element-encoded transposase catalyzes the excision of the transposon from its original location and promotes its insertion elsewhere in the genome (Plasterk, 1996 Curr. Top. Microbiol. Immunol. 204, 125-143). Autonomous members of a transposon family can express an active transposase, the trans-acting factor for transposition, and thus are capable of transposing on their own. Non-autonomous elements have mutated transposase genes but may retain cis-acting DNA sequences. These cis-acting DNA sequences are also referred to as inverted terminal repeats (IR). Some inverted repeat sequences may include one or more direct repeat sequences. These sequences usually are embedded in the terminal inverted repeats (IRs) of the elements, which are required for mobilization in the presence of a complementary transposase from another element. Not a single autonomous element has been isolated from vertebrates so far with the exception of Tol2 (see below); all transposon-like sequences are defective, apparently as a result of a process called "vertical inactivation" (Lohe et al., 1995 Mol. Biol. Evol. 12, 62-72). According to one phylogenetic model (Hartl et al., 1997 Trends Genet. 13, 197-201), the ratio of non-autonomous to autonomous elements in eukaryotic genomes increases as a result of the trans-complementary nature of transposition. This process leads to a state where the ultimate disappearance of active, transposase-producing copies in a genome is inevitable. Consequently, DNA-transposons can be viewed as transitory components of genomes which, in order to avoid extinction, must find ways to establish themselves in a new host. Indeed, horizontal gene transmission between species is thought to be one of the important processes in the evolution of transposons (Lohe et al., 1995 supra and Kidwell, 1992. Curr. Opin. Genet Dev. 2, 868-873).

The natural process of horizontal gene transfer can be mimicked under laboratory conditions. In plants, transposons of the Ac/Ds and Spm families have been routinely transfected into heterologous species (Osborne and Baker, 1995 Curr. Opin. Cell Biol. 7, 406-413). In animals, however, a major obstacle to the transfer of an active transposon system from one species to another has been that of species-specificity of transposition due to the requirement for factors produced by the natural host.

Transposon systems as discussed above may occur in vertebrate and invertebrate systems. In vertebrates, the discovery of DNA-transposons, mobile elements that move via a DNA intermediate, is relatively recent (Radice, A. D., et al., 1994. Mol. Gen. Genet. 244, 606-612). Since then, inactive, highly mutated members of the Tc1/mariner as well as the hAT (hobo/Ac/Tam) superfamilies of eukaryotic transposons have been isolated from different fish species, Xenopus and human genomes (Oosumi et al., 1995. Nature 378, 873; Ivics et al. 1995. Mol. Gen. Genet. 247, 312-322; Koga et al., 1996. Nature 383, 30; Lam et al., 1996. J. Mol. Biol. 257, 359-366 and Lam, W. L., et al. Proc. Natl. Acad Sci. USA 93, 10870-10875).

Both invertebrate and vertebrate transposons hold potential for transgenesis and insertional mutagenesis in model organisms. Particularly, the availability of alternative transposon systems in the same species opens up new possibilities for genetic analyses. For example, piggyBac transposons can be mobilized in *Drosophila* in the presence of stably inserted P elements (Hacker et al., (2003), Proc Natl Acad Sci USA 100, 7720-5). Because P element- and piggyBac-based systems show different insertion site preferences (Spradling et al. (1995), Proc Natl Acad Sci USA 92, 10824-30, Hacker et al., (2003), Proc Natl Acad Sci USA 100, 7720-5), the number of fly genes that can be insertionally inactivated by transposons can greatly be increased. P element vectors have also been used to insert components of the mariner transposon into the *D. melanogaster* genome by stable germline transformation. In these transgenic flies, mariner transposition can be studied without accidental mobilization of P elements (Lohe and Hartl, (2002), Genetics 160, 519-26).

In vertebrates, three active transposons are currently known and used: the Tol2 element in medaka, and the reconstructed transposons Sleeping Beauty (SB) and Frog Prince (FP). A further interesting transposon system in vertebrates is the PiggyBac transposon system (Ding et al., Cell, 2005).

The Tol2 element is an active member of the hAT transposon family in medaka. It was discovered by a recessive mutation causing an albino phenotype of the Japanese medaka (*Oryzias latipes*), a small freshwater fish of East Asia. It was found that the mutation is due to a 4.7-kb long TE insertion into the fifth exon of the tyrosinase gene. The DNA sequence of the element, named Tol1, is similar to transposons of the hAT family, including hobo of *Drosophila*, Ac of maize and Tam3 of snapdragon.

Sleeping Beauty (SB) is a Tc1/mariner-like element from fish and exhibits high transpositional activity in a variety of vertebrate cultured cell lines, embryonic stem cells and in both somatic and germ line cells of the mouse in vivo.

Also Frog Prince (FP) is a Tc1/mariner-like element that was recently reactivated from genomic transposon copies of the Northern Leopard Frog (*Rana pipiens*). An open reading frame trapping method was used to identify uninterrupted transposase coding regions, and the majority rule consensus of these sequences revealed an active transposase gene. Thus, in contrast to the "resurrection" procedure of SB, the relatively young state of genomic elements in *Rana pipiens* made it possible to ground the majority rule consensus on transposon copies derived from a single species. The SB and FP transposons are clearly distinct, sharing only ~50% identity in their transposase sequences.

Transposons as the above, particularly Tol2, SB and FP, as well as piggyback (Ding et al., Cell 2005), do not interact and thus may be used as a genetic tool in the presence of others, which considerably broadens the utility of these elements. The preferences of these transposons to insert into expressed genes versus non-coding DNA, and preferences for insertion sites within genes may be substantially different. If so, different patterns of insertion of these transposon systems can be exploited in a complementary fashion. For instance, one could use different transposon systems to transfect several transgenes into cells sequentially, without accidental and unwanted mobilization of already inserted transgenes. In addition, the number of target loci that can be mutagenized by transposon vectors could dramatically increase by combining different transposon systems in genome-wide screens.

In addition to the variation in transpositional activity in hosts, and differences in target site specificity, distinct structural properties of various elements could also be advantageous in certain applications. For example, transposon insertions can be utilized to misexpress genes and to look for gain-of-function phenotypes Rorth, P. (1996, A modular misexpression screen in *Drosophila* detecting tissue-specific phenotypes. Proc Natl Acad Sci USA 93, 12418-22.) used a modified P element transposon that carried an inducible promoter directed out from the element to force expression of host genes near to transposon insertion sites and detected tissue specific phenotypes. A prerequisite of such an experimental setup is that the transposon IRs allow read through transcription/translation across the IRs.

As was already explained above DNA transposons have been developed as gene transfer vectors in invertebrate model organisms and more recently, in vertebrates too. They also rose to be strong rivals of the retroviral systems in human gene therapy. As said before the most useful transposable elements (TEs) for genetic analyses and for therapeutic approaches are the Class II TEs moving in the host genome via a "cut-and-paste" mechanism (FIG. 1), due to their easy laboratory handling and controllable nature. Sleeping Beauty (hereinafter abbreviated as "SB") belongs to the Tc1/mariner family of the "cut-and-paste" transposons. The schematic outline of the transposition process of a "cut-and-paste" TE is represented in FIG. 1. These mobile DNA elements are simply organized, encoding a transposase protein in their genome flanked by the inverted terminal repeats (ITR). The ITRs carry the transposase binding sites necessary for transposition (FIG. 1). Their activities can easily be controlled by separating the transposase source from the transposable DNA harboring the ITRs, thereby creating a non-autonomous TE. In such a two-component system, the transposon can only move by transsupplementing the transposase protein (FIG. 1). Practically any sequence of interest can be positioned between the ITR elements according to experimental needs. The transposition will result in excision of the element from the vector DNA and subsequent single copy integration into a new sequence environment.

In general the transposon mediated chromosomal entry seems to be advantageous over viral approaches because on one hand transposons if compared to viral systems do not favour so much the active genes and 5' regulatory regions and thus are not so prone to mutagenesis, and on the other hand due to there special mechanism of chromosomal entry into of the gene of interest are more physiologically controlled.

SB already proved to be a valuable tool for functional genomics in several vertebrate model organisms (Miskey, C., Izsvak, Z., Kawakami, K. and Ivics, Z. (2005); DNA transposons in vertebrate functional genomics. *Cell Mol. Life. Sci.* 62: 629-641) and shows promise for human gene therapeutic applications (Ivics, Z. and Izsvak, Z. (2006). Transposons for gene therapy; *Curr. Gene Ther.* 6: 593-607). However for all of these applications the transpositional activity of the system is a key issue of usability and efficiency. Even though functional and valuable as commonly known and described as of today the transposase activity is likely to be one of the factors that still causes the SB system to reach its limits. Thus, a remarkable improvement of transpositional activity could breach current experimental barriers in both directions.

Thus, there still remains a need for improving the already valuable SB system as a method for introducing DNA into a cell. Accordingly, it is desired to enhance efficient insertion of transposons of varying size into the nucleic acid of a cell or the insertion of DNA into the genome of a cell thus allowing more efficient transcription/translation than currently available in the state of the art.

The object underlying the present invention is solved by a polypeptide selected from variants of SB10 transposase comprising an amino acid sequence differing from the sequence of native SB10 transposase according to SEQ ID NO: 1 by 1 to 20 amino acids including at least one of the following mutations or groups of mutations selected from: [0023] K14R, [0024] K13D, [0025] K13A, [0026] K30R, [0027] K33A, [0028] T83A, [0029] I100L, [0030] R115H, R143L, [0032] R147E, [0033] A205K/H207V/K208R/D210E; [0034] H207V/K208R/D210E; [0035] R214D/K215A/E216V/N217Q; [0036] M243H; [0037] M243Q; [0039] E267D;T314N; [0040] G317E.

The "SB10 transposase" is a well-known transposase of the "Sleeping Beauty Transposon System". Its amino acid sequence is included herein as SEQ. ID No.1 (FIG. 10).

"Mutation" or "mutations" is defined herein as the exchange of 1 or more amino acids of a known amino acid sequence by 1 or more other amino acids, respectively, and might—if specifically indicated—also a "group of mutations" or "groups of mutations". A "group of mutations" or "groups of mutations" are defined herein as the exchange of groups, e.g. 3 or 4, of amino acids from the original sequence by 3 or 4 other amino acids at the indicated positions, respectively. As a definition the following code is used to identify the above mutations. "XNo.Z" means that the amino acid "X" of the original amino acid sequence at position "No." is exchanged for amino acid "Z", whereas "XNo.Y/X'No.'Z'/X''No.''Z'''" is intended to mean that in this mutation amino acids "X" at position "No.", "X'" in position "No.'" and "X''" in position "No.''" are simultaneously exchanged for amino acid "Z", "Z'" and "Z''" respectively. If a "combination of mutations" is defined "//" is used to separate and indicate "simultaneous mutations" in this combination but otherwise is identical to a single slash "/".

In a preferred embodiment of the inventive polypeptide it is a variant of SB10 transposase differing from SEQ ID NO: 1 by 1 to 20 amino acids including at least one of the above-listed mutations or groups of mutations.

The inventive polypeptides (transposase variants), preferably combined in an inventive transposon as defined below, have several advantages compared to approaches in the prior art with the most prominent exhibiting a 100 fold increase in the transposase activity if compared to the activity of natural SB10.

Systematic mutagenesis studies have already been undertaken in the art to increase the activity of the SB transposases like the systematic exchange of the N-terminal 95 AA of the SB transposase for alanine (Yant, S. R., Park, J., Huang, Y., Mikkelsen, J. H G. and Kay, M. A. (2004) Mutational analysis of the N-terminal DNA-binding domain of Sleeping Beauty transposase: critical residues for DNA binding and hyperactivity in mammalian cells. *Mol. Cell Biol.* 24: 9239-9247). 10 out of these substitutions caused hyperactivity between 200-400% as compared to SB10 as a reference (Yant, 2004). In addition, a further variant being described in the art is SB16 (Baus, J., Liu, L., Heggestad, A. D., Sanz, S. and Fletcher, B. S. (2005) Hyperactive transposase mutants of the Sleeping Beauty transposon. *Mol. Therapy* 12: 1148-1156), which was reported to have a 16-fold activity increase as compared to natural SB10 and up to now by far the SB transposase published with the highest activity. SB16 was constructed by combining 5 individual hyperactive mutations (Baus, 2005).

In another preferred embodiment of the inventive polypeptide the variants are differing by at least 2, or by at least 1 to 8, preferably by 2 to 7 of the above-listed mutations or groups of mutations, even more preferably by at least 4 to 7 of the above-listed mutations or groups of mutations.

In another preferred embodiment of this inventive polypeptide the variants of SB10 transposase are selected from variants comprising the following combination of mutations:

Variant 1: K14R//R214D/K215A/E216V/N217Q;
Variant 2: K33A/R115H//R214D/K215A/E216V/N217Q//M243H;
Variant 3: K14R/K30R//A205K/H207V/K208R/D210E//R214D/K215A/E216V/N217Q//M243H;
Variant 4: K13D/K33A/T83A//H207V/K208R/D210E//M243Q;
Variant 5: K13A/K33A//R214D/K215A/E216V/N217Q;
Variant 6: K33A/T83A//R214D/K215A/E216V/N217Q//G317E;
Variant 7: K14R/T83A/M243Q;
Variant 8: K14R/T83A/I100L/M243Q;
Variant 9: K14R/T83A/R143L/M243Q;
Variant 10: K14R/T83A/R147E/M243Q;
Variant 11: K14R/T83A/M243Q/E267D;
Variant 12: K14R/T83A/M243Q/T314N;
Variant 13: K14R/K30R/I100L//A205K/H207V/K208R/D210E//R214D/K215A/E216V/N217Q//M243H;
Variant 14: K14R/K30R/R143L//A205K/H207V/K208R/D210E//R214D/K215A/E216V/N217Q//M243H;
Variant 15: K14R/K30R/R147E//A205K/H207V/K208R/D210E//R214D/K215A/E216V/N217Q//M243H;
Variant 16: K14R/K30R//A205K/H207V/K208R/D210E//R214D/K215A/E216V/N217Q//M243H/E267D;
Variant 17: K14R/K30R//A205K/H207V/K208R/D210E//R214D/K215A/E216V/N217Q//M243H/T314N;
Variant 18: K14R/K30R//A205K/H207V/K208R/D210E//R214D/K215A/E216V/N217Q//M243H/G317E;
Variant 19: K14R/K33A/R115H//R214D/K215A/E216V/N217Q//M243H;
Variant 20: K14R/K30R/R147E//A205K/H207V/K208R/D210E//R214D/K215A/E216V/N217Q//M243H/T314N;
Variant 21: K14R/K30R/R143L//A205K/H207V/K208R/D210E//R214D/K215A/E216V/N217Q//M243H/E267D;
Variant 22: K14R/K30R/R143L//A205K/H207V/K208R/D210E//R214D/K215A/E216V/N217Q//M243H/T314N;

Variant 23:
  K14R/K30R/R143L//A205K/H207V/K208R/D210E//
  R214D/K215A/E216V/N217Q//M243H/G317E;
Variant 24:
  K14R/K33A/R115H/R143L//R214D/K215A/E216V/
  N217Q//M243H;
Variant 25:
  K14R/K33A/R115H/R147E//R214D/K215A/E216V/
  N217Q//M243H;
Variant 26:
  K14R/K33A/R115H//R214D/K215A/E216V/N217Q//
  M243H/E267D;
Variant 27:
  K14R/K33A/R115H//R214D/K215A/E216V/N217Q//
  M243H/T314N;
Variant 28:
  K14R/K33A/R115H//R214D/K215A/E216V/N217Q//
  M243H/G317E;
Variant 29: K14R/T83A/M243Q/G317E;
Variant 30: K13A/K33A/T83A//R214D/K215A/E216V/
  N217Q
preferably selected from
Variant 1: K14R//R214D/K215A/E216V/N217Q;
Variant 2: K33A/R115H//R214D/K215A/E216V/
  N217Q//M243H;
Variant 3:
  K14R/K30R//A205K/H207V/K208R/D210E//R214D/
  K215A/E216V/N217Q//M243H;
Variant 4: K13D/K33A/T83A//H207V/K208R/D210E//
  M243Q;
Variant 5: K13A/K33A//R214D/K215A/E216V/N217Q;
Variant 6: K33A/T83A//R214D/K215A/E216V/N217Q//
  G317E;
Variant 7: K14R/T83A/M243Q;
Variant 8: K14R/T83A/I100L/M243Q;
Variant 9: K14R/T83A/R143L/M243Q;
Variant 10: K14R/T83A/R147E/M243Q;
Variant 11: K14R/T83A/M243Q/E267D;
Variant 12: K14R/T83A/M243Q/T314N;
Variant 14:
  K14R/K30R/R143L//A205K/H207V/K208R/D210E//
  R214D/K215A/E216V/N217Q//M243H;
Variant 15:
  K14R/K30R/R147E//A205K/H207V/K208R/D210E//
  R214D/K215A/E216V/N217Q//M243H;
Variant 16:
  K14R/K30R//A205K/H207V/K208R/D210E//R214D/
  K215A/E216V/N217Q//M243H/E267D;
Variant 17:
  K14R/K30R//A205K/H207V/K208R/D210E//R214D/
  K215A/E216V/N217Q//M243H/T314N;
Variant 18:
  K14R/K30R//A205K/H207V/K208R/D210E//R214D/
  K215A/E216V/N217Q//M243H/G317E;
Variant 19:
  K14R/K33A/R115H//R214D/K215A/E216V/N217Q//
  M243H;
Variant 20:
  K14R/K30R/R147E//A205K/H207V/K208R/D210E//
  R214D/K215A/E216V/N217Q//M243H/T314N;
Variant 21:
  K14R/K30R/R143L//A205K/H207V/K208R/D210E//
  R214D/K215A/E216V/N217Q//M243H/E267D;
Variant 23:
  K14R/K30R/R143L//A205K/H207V/K208R/D210E//
  R214D/K215A/E216V/N217Q//M243H/G317E;
Variant 24:
  K14R/K33A/R115H/R143L//R214D/K215A/E216V/
  N217Q//M243H;
Variant 25:
  K14R/K33A/R115H/R147E//R214D/K215A/E216V/
  N217Q//M243H;
Variant 26:
  K14R/K33A/R115H//R214D/K215A/E216V/N217Q//
  M243H/E267D;
Variant 27:
  K14R/K33A/R115H//R214D/K215A/E216V/N217Q//
  M243H/T314N;
Variant 28:
  K14R/K33A/R115H//R214D/K215A/E216V/N217Q//
  M243H/G317E;
more preferably selected from
Variant 2: K33A/R115H//R214D/K215A/E216V/
  N217Q//M243H;
Variant 3:
  K14R/K30R//A205K/H207V/K208R/D210E//R214D/
  K215A/E216V/N217Q//M243H;
Variant 14:
  K14R/K30R/R143L//A205K/H207V/K208R/D210E//
  R214D/K215A/E216V/N217Q//M243H;
Variant 15:
  K14R/K30R/R147E//A205K/H207V/K208R/D210E//
  R214D/K215A/E216V/N217Q//M243H;
Variant 16:
  K14R/K30R//A205K/H207V/K208R/D210E//R214D/
  K215A/E216V/N217Q//M243H/E267D;
Variant 19:
  K14R/K33A/R115H//R214D/K215A/E216V/N217Q//
  M243H;
Variant 20:
  K14R/K30R/R147E//A205K/H207V/K208R/D210E//
  R214D/K215A/E216V/N217Q//M243H/T314N;
Variant 21:
  K14R/K30R/R143L//A205K/H207V/K208R/D210E//
  R214D/K215A/E216V/N217Q//M243H/E267D;
Variant 23:
  K14R/K30R/R143L//A205K/H207V/K208R/D210E/
  R214D/K215A/E216V/N217Q//M243H/G317E;
Variant 24:
  K14R/K33A/R115H/R143L//R214D/K215A/E216V/
  N217Q//M243H;
Variant 25:
  K14R/K33A/R115H/R147E//R214D/K215A/E216V/
  N217Q//M243H;
Variant 26:
  K14R/K33A/R115H//R214D/K215A/E216V/N217Q//
  M243H/E267D;
Variant 27:
  K14R/K33A/R115H//R214D/K215A/E216V/N217Q//
  M243H/T314N;
Variant 28:
  K14R/K33A/R115H//R214D/K215A/E216V/N217Q//
  M243H/G317E.

These variants of SB10 transposase may also be selected from variants with combined mutations consisting of the group indicated above, preferably from those wherein the difference of the amino acid sequence of these variants from native SB10 transposase is consisting of the combination of mutations indicated above.

In another preferred embodiment of the inventive polypeptide, the variants of SB10 transposase comprise a sequence of amino acids differing from the amino acid sequence of native SB10 transposase according to SEQ ID NO: 1 by at least the group of mutations [0165] R214D/K215A/E216V/N217Q.

Accordingly, the variants of SB10 transposase which are selected from variants comprising the following combination of mutations are preferred:

Variant 1: K14R//R214D/K215A/E216V/N217Q;
Variant 2: K33A/R115H//R214D/K215A/E216V/N217Q//M243H;
Variant 3: K14R/K30R//A205K/H207V/K208R/D210E//R214D/K215A/E216V/N217Q//M243H;
Variant 5: K13A/K33A//R214D/K215A/E216V/N217Q;
Variant 6: K33A/T83A//R214D/K215A/E216V/N217Q//G317E;
Variant 13: K14R/K30R/I100L//A205K/H207V/K208R/D210E//R214D/K215A/E216V/N217Q//M243H;
Variant 14: K14R/K30R/R143L//A205K/H207V/K208R/D210E//R214D/K215A/E216V/N217Q//M243H;
Variant 15: K14R/K30R/R147E//A205K/H207V/K208R/D210E//R214D/K215A/E216V/N217Q//M243H;
Variant 16: K14R/K30R//A205K/H207V/K208R/D210E//R214D/K215A/E216V/N217Q//M243H/E267D;
Variant 17: K14R/K30R//A205K/H207V/K208R/D210E//R214D/K215A/E216V/N217Q//M243H/T314N;
Variant 18: K14R/K30R//A205K/H207V/K208R/D210E//R214D/K215A/E216V/N217Q//M243H/G317E;
Variant 19: K14R/K33A/R115H//R214D/K215A/E216V/N217Q//M243H;
Variant 20: K14R/K30R/R147E//A205K/H207V/K208R/D210E//R214D/K215A/E216V/N217Q//M243H/T314N;
Variant 21: K14R/K30R/R143L//A205K/H207V/K208R/D210E//R214D/K215A/E216V/N217Q//M243H/E267D;
Variant 22: K14R/K30R/R143L//A205K/H207V/K208R/D210E//R214D/K215A/E216V/N217Q//M243H/T314N;
Variant 23: K14R/K30R/R143L//A205K/H207V/K208R/D210E//R214D/K215A/E216V/N217Q//M243H/G317E;
Variant 24: K14R/K33A/R115H/R143L//R214D/K215A/E216V/N217Q//M243H;
Variant 25: K14R/K33A/R115H/R147E//R214D/K215A/E216V/N217Q//M243H;
Variant 26: K14R/K33A/R115H//R214D/K215A/E216V/N217Q//M243H/E267D;
Variant 27: K14R/K33A/R115H//R214D/K215A/E216V/N217Q//M243H/T314N;
Variant 28: K14R/K33A/R115H//R214D/K215A/E216V/N217Q//M243H/G317E;
preferably selected from
Variant 1: K14R//R214D/K215A/E216V/N217Q;
Variant 2: K33A/R115H//R214D/K215A/E216V/N217Q//M243H;
Variant 3: K14R/K30R//A205K/H207V/K208R/D210E//R214D/K215A/E216V/N217Q//M243H;
Variant 5: K13A/K33A//R214D/K215A/E216V/N217Q;
Variant 6: K33A/T83A//R214D/K215A/E216V/N217Q//G317E;
Variant 14: K14R/K30R/R143L//A205K/H207V/K208R/D210E//R214D/K215A/E216V/N217Q//M243H;
Variant 15: K14R/K30R/R147E//A205K/H207V/K208R/D210E//R214D/K215A/E216V/N217Q//M243H;
Variant 16: K14R/K30R//A205K/H207V/K208R/D210E//R214D/K215A/E216V/N217Q//M243H/E267D;
Variant 17: K14R/K30R//A205K/H207V/K208R/D210E//R214D/K215A/E216V/N217Q//M243H/T314N;
Variant 18: K14R/K30R//A205K/H207V/K208R/D210E//R214D/K215A/E216V/N217Q//M243H/G317E;
Variant 19: K14R/K33A/R115H//R214D/K215A/E216V/N217Q//M243H;
Variant 20: K14R/K30R/R147E//A205K/H207V/K208R/D210E//R214D/K215A/E216V/N217Q//M243H/T314N;
Variant 21: K14R/K30R/R143L//A205K/H207V/K208R/D210E//R214D/K215A/E216V/N217Q//M243H/E267D;
Variant 23: K14R/K30R/R143L//A205K/H207V/K208R/D210E//R214D/K215A/E216V/N217Q//M243H/G317E;
Variant 24: K14R/K33A/R115H/R143L//R214D/K215A/E216V/N217Q//M243H;
Variant 25: K14R/K33A/R115H/R147E//R214D/K215A/E216V/N217Q//M243H;
Variant 26: K14R/K33A/R115H//R214D/K215A/E216V/N217Q//M243H/E267D;
Variant 27: K14R/K33A/R115H//R214D/K215A/E216V/N217Q//M243H/T314N;
Variant 28: K14R/K33A/R115H//R214D/K215A/E216V/N217Q//M243H/G317E;
more preferably selected from
Variant 2: K33A/R115H//R214D/K215A/E216V/N217Q//M243H;
Variant 3: K14R/K30R//A205K/H207V/K208R/D210E//R214D/K215A/E216V/N217Q//M243H;
Variant 14: K14R/K30R/R143L//A205K/H207V/K208R/D210E//R214D/K215A/E216V/N217Q//M243H;
Variant 15: K14R/K30R/R147E//A205K/H207V/K208R/D210E//R214D/K215A/E216V/N217Q//M243H;
Variant 16: K14R/K30R//A205K/H207V/K208R/D210E//R214D/K215A/E216V/N217Q//M243H/E267D;
Variant 19: K14R/K33A/R115H//R214D/K215A/E216V/N217Q//M243H;

Variant 20:
  K14R/K30R/R147E//A205K/H207V/K208R/D210E//
  R214D/K215A/E216V/N217Q//M243H/T314N;
Variant 21:
  K14R/K30R/R143L//A205K/H207V/K208R/D210E//
  R214D/K215A/E216V/N217Q//M243H/E267D;
Variant 23:
  K14R/K30R/R143L//A205K/H207V/K208R/D210E//
  R214D/K215A/E216V/N217Q//M243H/G317E;
Variant 24:
  K14R/K33A/R115H/R143L//R214D/K215A/E216V/
  N217Q//M243H;
Variant 25:
  K14R/K33A/R115H/R147E//R214D/K215A/E216V/
  N217Q//M243H;
Variant 26:
  K14R/K33A/R115H//R214D/K215A/E216V/N217Q//
  M243H/E267D;
Variant 27:
  K14R/K33A/R115H//R214D/K215A/E216V/N217Q//
  M243H/T314N;
Variant 28:
  K14R/K33A/R115H//R214D/K215A/E216V/N217Q//
  M243H/G317E.

These variants of SB10 transposase may also be selected from variants with combined mutations consisting of the group indicated above, preferably from those wherein the difference of the amino acid sequence of these variants from native SB10 transposase is consisting of the combination of mutations indicated above.

In another preferred embodiment of the present invention variants of SB10 transposase comprise a sequence of amino acids differing from native SB10 transposase according to SEQ ID NO: 1 by 1 to 20 amino acids including at least the group of mutations and mutation
  R214D/K215A/E216V/N217Q and
  K14R.

Accordingly variants of SB10 transposase which are selected from variants comprising the following combination of mutations are preferred:
Variant 1: K14R//R214D/K215A/E216V/N217Q;
Variant 3:
  K14R/K30R//A205K/H207V/K208R/D210E//R214D/
  K215A/E216V/N217Q//M243H;
Variant 13:
  K14R/K30R/I100L//A205K/H207V/K208R/D210E//
  R214D/K215A/E216V/N217Q//M243H;
Variant 14:
  K14R/K30R/R143L//A205K/H207V/K208R/D210E//
  R214D/K215A/E216V/N217Q//M243H;
Variant 15:
  K14R/K30R/R147E//A205K/H207V/K208R/D210E//
  R214D/K215A/E216V/N217Q//M243H;
Variant 16:
  K14R/K30R//A205K/H207V/K208R/D210E//R214D/
  K215A/E216V/N217Q//M243H/E267D;
Variant 17:
  K14R/K30R//A205K/H207V/K208R/D210E//R214D/
  K215A/E216V/N217Q//M243H/T314N;
Variant 18:
  K14R/K30R//A205K/H207V/K208R/D210E//R214D/
  K215A/E216V/N217Q//M243H/G317E;
Variant 19:
  K14R/K33A/R115H//R214D/K215A/E216V/N217Q//
  M243H;
Variant 20:
  K14R/K30R/R147E//A205K/H207V/K208R/D210E//
  R214D/K215A/E216V/N217Q//M243H/T314N;
Variant 21:
  K14R/K30R/R143L//A205K/H207V/K208R/D210E//
  R214D/K215A/E216V/N217Q//M243H/E267D;
Variant 22:
  K14R/K30R/R143L//A205K/H207V/K208R/D210E//
  R214D/K215A/E216V/N217Q//M243H/T314N;
Variant 23:
  K14R/K30R/R143L//A205K/H207V/K208R/D210E//
  R214D/K215A/E216V/N217Q//M243H/G317E;
Variant 24:
  K14R/K33A/R115H/R143L//R214D/K215A/E216V/
  N217Q//M243H;
Variant 25:
  K14R/K33A/R115H/R147E//R214D/K215A/E216V/
  N217Q//M243H;
Variant 26:
  K14R/K33A/R115H//R214D/K215A/E216V/N217Q//
  M243H/E267D;
Variant 27:
  K14R/K33A/R115H//R214D/K215A/E216V/N217Q//
  M243H/T314N;
Variant 28:
  K14R/K33A/R115H//R214D/K215A/E216V/N217Q//
  M243H/G317E;
preferably selected from
Variant 1: K14R//R214D/K215A/E216V/N217Q;
Variant 3:
  K14R/K30R//A205K/H207V/K208R/D210E//R214D/
  K215A/E216V/N217Q//M243H;
Variant 14:
  K14R/K30R/R143L//A205K/H207V/K208R/D210E//
  R214D/K215A/E216V/N217Q//M243H;
Variant 15:
  K14R/K30R/R147E//A205K/H207V/K208R/D210E//
  R214D/K215A/E216V/N217Q//M243H;
Variant 16:
  K14R/K30R//A205K/H207V/K208R/D210E//R214D/
  K215A/E216V/N217Q//M243H/E267D;
Variant 17:
  K14R/K30R//A205K/H207V/K208R/D210E//R214D/
  K215A/E216V/N217Q//M243H/T314N;
Variant 18:
  K14R/K30R//A205K/H207V/K208R/D210E//R214D/
  K215A/E216V/N217Q//M243H/G317E;
Variant 19:
  K14R/K33A/R115H//R214D/K215A/E216V/N217Q//
  M243H;
Variant 20:
  K14R/K30R/R147E//A205K/H207V/K208R/D210E//
  R214D/K215A/E216V/N217Q//M243H/T314N;
Variant 21:
  K14R/K30R/R143L//A205K/H207V/K208R/D210E//
  R214D/K215A/E216V/N217Q//M243H/E267D;
Variant 23:
  K14R/K30R/R143L//A205K/H207V/K208R/D210E//
  R214D/K215A/E216V/N217Q//M243H/G317E;
Variant 24:
  K14R/K33A/R115H/R143L//R214D/K215A/E216V/
  N217Q//M243H;
Variant 25:
  K14R/K33A/R115H/R147E//R214D/K215A/E216V/
  N217Q//M243H;
Variant 26:
  K14R/K33A/R115H//R214D/K215A/E216V/N217Q//
  M243H/E267D;

Variant 27:
   K14R/K33A/R115H//R214D/K215A/E216V/N217Q//M243H/T314N;
Variant 28:
   K14R/K33A/R115H//R214D/K215A/E216V/N217Q//M243H/G317E;
more preferably selected from
Variant 3:
   K14R/K30R//A205K/H207V/K208R/D210E//R214D/K215A/E216V/N217Q//M243H;
Variant 14:
   K14R/K30R/R143L//A205K/H207V/K208R/D210E//R214D/K215A/E216V/N217Q//M243H;
Variant 15:
   K14R/K30R/R147E//A205K/H207V/K208R/D210E//R214D/K215A/E216V/N217Q//M243H;
Variant 16:
   K14R/K30R//A205K/H207V/K208R/D210E//R214D/K215A/E216V/N217Q//M243H/E267D;
Variant 19:
   K14R/K33A/R115H//R214D/K215A/E216V/N217Q//M243H;
Variant 20:
   K14R/K30R/R147E//A205K/H207V/K208R/D210E//R214D/K215A/E216V/N217Q//M243H/T314N;
Variant 21:
   K14R/K30R/R143L//A205K/H207V/K208R/D210E//R214D/K215A/E216V/N217Q//M243H/E267D;
Variant 23:
   K14R/K30R/R143L//A205K/H207V/K208R/D210E//R214D/K215A/E216V/N217Q//M243H/G317E;
Variant 24:
   K14R/K33A/R115H/R143L//R214D/K215A/E216V/N217Q//M243H;
Variant 25:
   K14R/K33A/R115H/R147E//R214D/K215A/E216V/N217Q//M243H;
Variant 26:
   K14R/K33A/R115H//R214D/K215A/E216V/N217Q//M243H/E267D;
Variant 27:
   K14R/K33A/R115H//R214D/K215A/E216V/N217Q//M243H/T314N;
Variant 28:
   K14R/K33A/R115H//R214D/K215A/E216V/N217Q//M243H/G317E.
most preferably selected from
Variant 19:
   K14R/K33A/R115H//R214D/K215A/E216V/N217Q//M243H;
Variant 24:
   K14R/K33A/R115H/R143L//R214D/K215A/E216V/N217Q//M243H;
Variant 25:
   K14R/K33A/R115H/R147E//R214D/K215A/E216V/N217Q//M243H;
Variant 26:
   K14R/K33A/R115H//R214D/K215A/E216V/N217Q//M243H/E267D;
Variant 27:
   K14R/K33A/R115H//R214D/K215A/E216V/N217Q//M243H/T314N;
Variant 28:
   K14R/K33A/R115H//R214D/K215A/E216V/N217Q//M243H/G317E.
These variants of SB10 transposase may also be selected from variants with combined mutations consisting of the group indicated above, preferably from those wherein the difference of the amino acid sequence of these variants from native SB10 transposase is consisting of the combination of mutations indicated above.

In another very preferred embodiment of the present invention variants of SB10 transposase comprise a sequence of amino acids differing from native SB10 transposase according to SEQ ID NO: 1 by 1 to 20 amino acids including at least the group of mutations and mutation
   R214D/K215A/E216V/N217Q and
   K14R,
   and 2 to 6 additional mutations or groups of mutations selected from
   K30R,
   K33A,
   R115H,
   R143L,
   R147E,
   A205K/H207V/K208R/D210E;
   M243H;
   E267D;
   T314N;
   G317E;
   preferably 3 to 5 additional mutations selected from
   K30R,
   K33A,
   R115H,
   R143L,
   R147E,
   A205K/H207V/K208R/D210E;
   M243H;
   E267D;
   T314N;
   G317E.

Accordingly variants of SB10 transposase which are selected from variants comprising the following combination of mutations are preferred:
   Variant 3:
      K14R/K30R//A205K/H207V/K208R/D210E//R214D/K215A/E216V/N217Q//M243H;
   Variant 14:
      K14R/K30R/R143L//A205K/H207V/K208R/D210E//R214D/K215A/E216V/N217Q//M243H;
   Variant 15:
      K14R/K30R/R147E//A205K/H207V/K208R/D210E//R214D/K215A/E216V/N217Q//M243H;
   Variant 16:
      K14R/K30R//A205K/H207V/K208R/D210E//R214D/K215A/E216V/N217Q//M243H/E267D;
   Variant 17:
      K14R/K30R//A205K/H207V/K208R/D210E//R214D/K215A/E216V/N217Q//M243H/T314N;
   Variant 18:
      K14R/K30R//A205K/H207V/K208R/D210E//R214D/K215A/E216V/N217Q//M243H/G317E;
   Variant 19:
      K14R/K33A/R115H//R214D/K215A/E216V/N217Q//M243H;
   Variant 20:
      K14R/K30R/R147E//A205K/H207V/K208R/D210E//R214D/K215A/E216V/N217Q//M243H/T314N;
   Variant 21:
      K14R/K30R/R143L//A205K/H207V/K208R/D210E//R214D/K215A/E216V/N217Q//M243H/E267D;
   Variant 23:
      K14R/K30R/R143L//A205K/H207V/K208R/D210E//R214D/K215A/E216V/N217Q//M243H/G317E;

Variant 24:
K14R/K33A/R115H/R143L//R214D/K215A/E216V/N217Q//M243H;
Variant 25:
K14R/K33A/R115H/R147E//R214D/K215A/E216V/N217Q//M243H;
Variant 26:
K14R/K33A/R115H//R214D/K215A/E216V/N217Q//M243H/E267D;
Variant 27:
K14R/K33A/R115H//R214D/K215A/E216V/N217Q//M243H/T314N;
Variant 28:
K14R/K33A/R115H//R214D/K215A/E216V/N217Q//M243H/G317E;
preferably selected from
Variant 14:
K14R/K30R/R143L//A205K/H207V/K208R/D210E//R214D/K215A/E216V/N217Q//M243H;
Variant 19:
K14R/K33A/R115H//R214D/K215A/E216V/N217Q//M243H;
Variant 20:
K14R/K30R/R147E//A205K/H207V/K208R/D210E//R214D/K215A/E216V/N217Q//M243H/T314N;
Variant 21:
K14R/K30R/R143L//A205K/H207V/K208R/D210E//R214D/K215A/E216V/N217Q//M243H/E267D;
Variant 23:
K14R/K30R/R143L//A205K/H207V/K208R/D210E//R214D/K215A/E216V/N217Q//M243H/G317E;
Variant 24:
K14R/K33A/R115H/R143L//R214D/K215A/E216V/N217Q//M243H;
Variant 25:
K14R/K33A/R115H/R147E//R214D/K215A/E216V/N217Q//M243H;
Variant 26:
K14R/K33A/R115H//R214D/K215A/E216V/N217Q//M243H/E267D;
Variant 27:
K14R/K33A/R115H//R214D/K215A/E216V/N217Q//M243H/T314N;
Variant 28:
K14R/K33A/R115H//R214D/K215A/E216V/N217Q//M243H/G317E.

These variants of SB10 transposase may also be selected from variants with combined mutations consisting of the group indicated above, preferably from those wherein the difference of the amino acid sequence of these variants from native SB10 transposase is consisting of the combination of mutations indicated above.

In a highly preferred embodiment of the present invention variants of SB10 transposase comprise an amino acid sequence differing from the native SB10 transposase according to SEQ ID NO: 1 by 1 to 20 amino acids including at least the mutations
R214D/K215NE216V/N217Q,
K14R
and 3 to 4 additional mutations selected from
K33A,
R115H,
R143L,
R147E,
M243H;
E267D;
T314N;
G317E;
preferably comprising an amino acid sequence differing from native SB10 transposase according to SEQ ID NO: 1 by 1 to 20 amino acids including at least the group of mutations and mutations
R214D/K215NE216V/N217Q,
K14R
K33A,
R115H, and
M243H;
and 0 or 1 additional mutation selected from
R143L,
R147E,
E267D;
T314N;
G317E.

Accordingly variants of SB10 transposase, which are selected from variants comprising the following combination of mutations, are preferred:
Variant 19:
K14R/K33A/R115H//R214D/K215A/E216V/N217Q//M243H;
Variant 24:
K14R/K33A/R115H/R143L//R214D/K215A/E216V/N217Q//M243H;
Variant 25:
K14R/K33A/R115H/R147E//R214D/K215A/E216V/N217Q//M243H;
Variant 26:
K14R/K33A/R115H//R214D/K215A/E216V/N217Q//M243H/E267D;
Variant 27:
K14R/K33A/R115H//R214D/K215A/E216V/N217Q//M243H/T314N;
Variant 28:
K14R/K33A/R115H//R214D/K215A/E216V/N217Q//M243H/G317E.

These variants of SB10 transposase may also be selected from variants with combined mutations consisting of the group indicated above, preferably from those wherein the difference of the amino acid sequence of these variants from native SB10 transposase is consisting of the combination of mutations indicated above.

Another aspect of the present invention refers to a nucleic acid comprising a nucleotide sequence encoding an inventive polypeptide as defined above. Nucleic acids according to the present invention typically comprise ribonucleic acids, including mRNA, DNA, cDNA, chromosomal DNA, extrachromosomal DNA, plasmid DNA, viral DNA or RNA, including also a recombinant viral vector. Thus, in a preferred embodiment of the nucleic acid according to the invention the nucleic acid is DNA or RNA and in another preferred embodiment the nucleic acid is part of a plasmid or a recombinant viral vector. An inventive nucleic acid is preferably selected from any nucleic sequence encoding the amino acid sequence of the inventive polypeptide. Therefore all nucleic acid variants coding for the abovementioned inventive mutated SB10 variants including nucleic acid variants with varying nucleotide sequences due to the degeneration of the genetic code. In particular nucleotide sequences of nucleic acid variants which lead to an improved expression of the encoded fusion protein in a selected host organism, are preferred. Tables for appropriately adjusting a nucleic acid sequence to the host cell's specific transcription/translation machinery are known to a skilled person. In general, it is preferred to adapt the G/C-content of the nucleotide sequence to the specific host cell conditions. For expression in human cells an increase of the G/C content by at least 10%, more preferred at least 20%, 30%, 50%, 70% and even more preferred 90% of the maximum G/C content (coding for the respective inventive peptide variant) is preferred. Preparation and purification of such nucleic acids and/or derivatives are usually carried out by standard procedures (see Sambrook et al. 2001, Molecular Cloning: A Laboratory Manual, Cold Spring Harbor, N.Y.).

These sequence variants preferably lead to inventive polypeptides or proteins selected from variants of SB10 transposase comprising an amino acid sequence according to SEQ ID NO:1, which have at least one amino acid substituted as compared to the native nucleic acid sequence (SEQ ID NO:1) of SB10. Therefore, inventive nucleic acid sequences code for 30 modified (non-natural) variants of SB10. Further, promoters or other expression control regions can be operably linked with the nucleic acid encoding the inventive polypeptide to regulate expression of the polypeptide/protein in a quantitative or in a tissue-specific manner.

The inventive polypeptide as defined above can be transfected into a cell as a protein or as ribonucleic acid, including mRNA, as DNA, e.g. as extrachromosomal DNA including, but not limited to, episomal DNA, as plasmid DNA, or as viral nucleic acid. Furthermore, the inventive nucleic acid encoding the inventive polypeptide/protein can be transfected into a cell as a nucleic acid vector such as a plasmid, or as a gene expression vector, including a viral vector. Therefore, the nucleic acid can be circular or linear. A vector, as used herein, refers to a plasmid, a viral vector or a cosmid that can incorporate nucleic acid encoding the polypeptide or the transposon (described in more detail below) of this invention. The terms "coding sequence" or "open reading frame" refer to a region of nucleic acid that can be transcribed and/or translated into a polypeptide in vivo when placed under the control of the appropriate regulatory sequences.

So, in a preferred embodiment of the nucleic acid according to the invention the nucleic acid additionally comprises at least an open reading frame. In another preferred embodiment, the nucleic acid additionally comprises at least a regulatory region of a gene. Preferably, the regulatory region is a transcriptional regulatory region, and more specifically the regulatory region is selected from the group consisting of a promoter, an enhancer, a silencer, a locus-control region, and a border element.

DNA encoding the inventive polypeptide can be stably inserted into the genome of the cell or into a—preferably autonomously replicating—vector for constitutive or inducible expression. Where the inventive polypeptide/protein is transfected into the cell or inserted into the vector as nucleic acid, the inventive polypeptide/protein (an SB10 transposase variant) encoding sequence is preferably operably linked to a promoter. There are a variety of promoters that may be used including, but not limited to, constitutive promoters, tissue-specific promoters, inducible promoters, and the like. Promoters are regulatory signals that bind RNA polymerase in a cell to initiate transcription of a downstream (3' direction) coding sequence. A DNA sequence is operably linked to an expression-control sequence, such as a promoter when the expression control sequence controls and regulates the transcription and translation of that DNA sequence. The term "operably linked" includes having an appropriate start signal (e.g., ATG) upstream of the DNA sequence to be expressed and maintaining the correct reading frame to permit expression of the DNA sequence under the control of the expression control sequence to yield production of the desired protein product. In reference to the disclosure above, the inventive DNA or RNA nucleotide sequences may vary even though they code for the same inventive polypeptide, due to the degeneracy of the three letter codons. For example, it is well known in the art that various specific RNA codons (corresponding DNA codons, with a T substituted for a U) can be used interchangeably to code for specific amino acids.

Methods for manipulating DNA and proteins are known in the art and are explained in detail in the literature such as Sambrook et al, (1989) Molecular Cloning: A Laboratory Manual., Cold Spring Harbor Laboratory Press or Ausubel, R. M., ed. (1994). Current Protocols in Molecular Biology.

In another aspect of the invention refers to an antisense-nucleic acid comprising a nucleotide sequence which hybridizes under stringent conditions to a nucleic acid according to the invention. This antisense RNA may be used for silencing purposes. In another embodiment an siRNA is coding for this antisense-RNA according to the invention.

Another aspect of this invention refers to a transposon, also referred to herein as a transposable element, that includes a nucleic acid sequence positioned between at least two repeats (IRs and/or RSDs), at least one repeat on either side of the nucleic acid sequence. Preferably, the inventive transposon comprises the nucleic acid sequence positioned between at least two repeats (IRs and/or RSDs) on either side flanking the nucleic acid sequence in between, wherein these repeats can bind to an inventive polypeptide as defined above and wherein the transposon is capable of inserting into DNA of a cell, especially is capable of inserting the nucleic acid sequence or a portion of the into nucleic acid into the DNA of a cell. In other words, repeats are defined as sequences which are recognized and bound by the inventive polypeptide as defined above.

The basic structure of an inventive transposon, which is bound by an inventive polypeptide (a transposase variant), contains a pair of repeat sequences. Therein, the first repeat is typically located upstream to the above mentioned nucleic acid sequence and the second repeat is typically located downstream of this nucleic acid sequence. In this typical structure, the second repeat represents the same sequence as the first repeat, but shows an inverted reading direction as compared with the first repeat (5' and 3' ends of the complementary double strand sequences are exchanged). These repeats are then termed "inverted repeats" (IRs), due to the fact that both repeats are just inversely repeated sequences.

By another structure repeats as defined above may occur in a multiple number upstream and downstream of the above mentioned nucleic acid sequence. Then, preferably two, or eventually three, four, or more repeats are located upstream and/or downstream to the above mentioned nucleic acid sequence. Preferably, the number of repeats located upstream and downstream of the above mentioned nucleic acid sequence is identical. If multiple copies of IRs exist on each terminus of the nucleic acid sequence, some or, more preferably, all of these multiple copies of the IRs at each terminus may have the same orientation as the IRs and are herein termed "repeats of the same direction" (RSD). In such a preferred situation the repeat assembly is termed IR/RSD.

For the (IR/RSD) structure, the multiple repeats located upstream and/or downstream of the above mentioned nucleic acid sequence may be arranged such as to be ligated directly to each other. Alternatively, these repeats may be separated by a spacer sequence. This spacer sequence is typically formed by a number of nucleic acids, preferably 50 to 200 nucleic acids.

The repeats (IRs and/or RSDs) as defined above preferably flank a nucleic acid sequence which is inserted into the DNA of a cell. The nucleic acid sequence can include an open reading frame, especially all or part of an open reading frame of a gene (i.e., the protein coding region), one or more expression control sequences (i.e., regulatory regions in nucleic acid) alone or together with all or part of an open reading frame. Preferred expression control sequences include, but are not limited to promoters, enhancers, border control elements, locus-control regions or silencers. In a preferred embodiment, the nucleic acid sequence comprises a promoter operably linked to at least a portion of an open reading frame. Finally the inventive transposons preferably occur as a linear transposon (extending from the 5' end to the 3' end, by convention) that can be used as a linear fragment or circularized, for example in a plasmid.

In one alternative embodiment of the inventive transposon, the nucleic acid sequence positioned between at least two repeats (IRs and/or RSDs) is a nucleic acid according to the invention comprising a nucleotide sequence which encodes an inventive polypeptide. Alternatively, the transposon may also contain more than one, e.g. 2, 3, or 4, or more coding regions (regulated under a common promoter and/or individually) for an inventive polypeptide with improved transposase functionality.

In another alternative embodiment of the inventive transposon, the nucleic acid sequence positioned between at least two repeats (IRs and/or RSDs) can be of any recombinant protein. E.g. the protein encoded by the nucleic acid sequence can be a marker protein such as green fluorescent protein (GFP), the blue fluorescent protein (BFP), the photo activatable-GFP (PA-GFP), the yellow shifted green fluorescent protein (Yellow GFP), the yellow fluorescent protein (YFP), the enhanced yellow fluorescent protein (EYFP), the cyan fluorescent protein (CFP), the enhanced cyan fluorescent protein (ECFP), the monomeric red fluorescent protein (mRFP1), the kindling fluorescent protein (KFP1), aequorin, the autofluorescent proteins (AFPs), or the fluorescent proteins JRed, TurboGFP, PhiYFP and PhiYFP-m, tHc-Red (HcRed-Tandem), PS-CFP2 and KFP-Red (all available from EVRΩGEN, see also www.evrogen.com), or other suitable fluorescent proteins chloramphenicol acetyltransferase (CAT). The protein further may be selected from "proteins of interest". Proteins of interest include growth hormones, for example to promote growth in a transgenic animal, or from [beta]-galactosidase (lacZ), luciferase (LUC), and insulin-like growth factors (IGFs), □-antitrypsin, erythropoietin (EPO), factors VIII and XI of the blood clotting system, LDL-receptor, GATA-1, etc. The nucleic acid sequence further may be a suicide gene encoding e.g. apoptotic or apoptose related enzymes and genes including AIF, Apaf e.g. Apaf-1, Apaf-2, Apaf-3, or APO-2 (L), APO-3 (L), Apopain, Bad, Bak, Bax, Bcl-2, Bcl-x$_L$, Bcl-x$_S$, bik, CAD, Calpain, Caspases e.g. Caspase-1, Caspase-2, Caspase-3, Caspase-4, Caspase-5, Caspase-6, Caspase-7, Caspase-8, Caspase-9, Caspase-10, Caspase-11, or Granzyme B, ced-3, ced-9, Ceramide, c-Jun, c-Myc, CPP32, crm A, Cytochrome c, D4-GDP-DI, Daxx, CdR1, DcR1, DD, DED, DISC, DNA-PKcs, DR3, DR4, DR5, FADD/MORT-1, FAK, Fas, Fas-ligand CD95/fas (receptor), FLICE/MACH, FLIP, Fodrin, fos, G-Actin, Gas-2, Gelsolin, glucocorticoid/glucocorticoid receptor, granzyme A/B, hnRNPs C1/C2, ICAD, ICE, JNK, Lamin A/B, MAP, MCL-1, Mdm-2, MEKK-1, MORT-1, NEDD, NF-□B, NuMa, p53, PAK-2, PARP, Perforin, PITSLRE, PKC□, pRb, Presenilin, prICE, RAIDD, Ras, RIP, Sphingomyelinase, SREBPs, thymidine kinase from Herpes simplex, TNF-□, TNF-□ receptor, TRADD, TRAF2, TRAIL-R1, TRAIL-R2, TRAIL-R3, Transglutaminase, U1 70 kDa snRNP, YAMA, etc. Finally, the nucleic acid sequence being located in the inventive transposon may be selected from short RNA hairpin expression cassettes. Also, the nucleic acid sequence may be either an siRNA (double-stranded RNA of 20 to 25, in particular 21 to 23 oligonucleotides, corresponding e.g. to the coding region of a gene the expression of which shall be reduced or suppressed or may be an antisense-RNA comprising a nucleotide sequence, which hybridizes under stringent conditions to e.g. an mRNA sequence in the cell, thereby reducing or suppressing the translation of the cellular mRNA.

In a further embodiment, the region between the flanking sequence may be composed of more than one coding regions, e.g. 2, 3, 4 coding regions, which may be mono- or multicistronic. If at least one nucleic acid sequence, which may be involved in therapeutics, diagnostic or scientific applications, is provided to the core of the transposon, at least one further coding region may code for an inventive polypeptide with improved transposase functionality.

In general the therapeutic applications of this invention may be manifold and thus polypeptide, the nucleic acid, and especially the transposon and/or the gene transfer system according to the invention may also find use in therapeutic applications, in which the transposon systems are employed to stably integrate a therapeutic nucleic acid ("nucleic acid of therapeutic interest"), e.g. gene (nucleic acid of therapeutic interest), into the genome of a target cell, i.e. gene therapy applications. This may also be of interest for vaccination therapy for the integration of antigens into antigen presenting cells, e.g specific tumor antigens, e.g. MAGE-1, for tumor vaccination or pathological antigens for the treatment of infectious diseases derived from pathogens, e.g. leprosy, tetanus, Whooping Cough, Typhoid Fever, Paratyphoid Fever, Cholera, Plague, Tuberculosis, Meningitis, Bacterial Pneumonia, Anthrax, Botulism, Bacterial Dysentry, Diarrhoea, Food Poisoning, Syphilis, Gasteroenteritis, Trench Fever, Influenza, Scarlet Fever, Diphtheria, Gonorrhoea, Toxic Shock Syndrome, Lyme Disease, Typhus Fever, Listeriosis, Peptic Ulcers, and Legionnaires' Disease; for the treatment of viral infections resulting in e.g. Acquired Immunodeficiency Syndrome, Adenoviridae Infections, Alphavirus Infections, Arbovirus Infections, Borna Disease, Bunyaviridae Infections, Caliciviridae Infections, Chickenpox, Condyloma Acuminata, Coronaviridae Infections, Coxsackievirus Infections, Cytomegalovirus Infections, Dengue, DNA Virus Infections, Ecthyma, Contagious, Encephalitis, Arbovirus, Epstein-Barr Virus Infections, Erythema Infectiosum, Hantavirus Infections, Hemorrhagic Fevers, Viral, Hepatitis, Viral, Human, Herpes Simplex, Herpes Zoster, Herpes Zoster Oticus, Herpesviridae Infections, Infectious Mononucleosis, Influenza in Birds, Influenza, Human, Lassa Fever, Measles, Molluscum Contagiosum, Mumps, Paramyxoviridae Infections, Phlebotomus Fever, Polyomavirus Infections, Rabies, Respiratory Syncytial Virus Infections, Rift Valley Fever, RNA Virus Infections, Rubella, Slow Virus Diseases, Smallpox, Subacute Sclerosing Panencephalitis, Tumor Virus Infections, Warts, West Nile Fever, Virus Diseases, Yellow Fever; for the treatment of protozoological infections resulting in e.g. malaria. Typically, the antigen used to treat infectious diseases by the inventive transposon system contains at least one surface antigen of any bacterial, viral or protozoological pathogen.

The subject transposon systems may be used to deliver a wide variety of therapeutic nucleic acids. Therapeutic nucleic acids of interest include genes that replace defective genes in the target host cell, such as those responsible for genetic defect based diseased conditions; genes which have therapeutic utility in the treatment of cancer; and the like. Specific therapeutic genes for use in the treatment of genetic defect based disease conditions include genes encoding the following products: factor VIII, factor IX, [beta]-globin, low-density protein receptor, adenosine deaminase, purine nucleoside phosphorylase, sphingomyelinase, glucocerebrosidase, cystic fibrosis transmembrane regulator, [alpha]-antitrypsin, CD-18, ornithine transcarbamylase, arginosuccinate synthetase, phenylalanine hydroxylase, branched-chain [alpha]-ketoacid dehydrogenase, fumarylacetoacetate hydrolase, glucose 6-phosphatase, [alpha]-L-fucosidase, [beta]-glucuronidase, [alpha]-L-iduronidase, galactose 1-phosphate uridyltransferase, and the like. Cancer therapeutic genes that may be delivered via the subject methods include: genes that enhance the antitumor activity of lymphocytes, genes whose expression product enhances the immunogenicity of tumor cells, tumor suppressor genes, toxin genes, suicide genes, multiple-drug resistance genes, antisense sequences, and the like. The subject methods can be used to not only introduce a therapeutic gene of interest, but also any expression regulatory elements, such as promoters, and the like, which may be desired so as to obtain the desired temporal and spatial expression of the therapeutic gene. An important feature of the subject methods, the gene therapy application, as described supra, is that the subject methods may be used for in vivo gene therapy applications. By in vivo gene therapy applications is meant that the target cell or cells in which expression of the therapeutic gene is desired are not removed from the host prior to contact with the transposon system. In contrast, vectors that include the transposon system are administered directly, preferably by injection, to the multicellular organism and are taken up by the target cells, following which integration of the gene into the target cell genome occurs.

In a preferred embodiment in the transposon according to the invention the nucleic acid sequence is a nucleic acid sequence according to the invention and/or a nucleic acid sequence coding for a marker protein such as green fluorescent protein (GFP), chloramphenicol acetyltransferase (CAT), a growth hormone, [beta]-galactosidase (lacZ), luciferase (LUC), or insulin-like growth factor (IGFs) and/or a nucleic acid of therapeutic or diagnostic interest.

In a further preferred embodiment, the inventive transposon may occur in a so called "sandwich structure". By this "sandwich structure" the inventive transposon occurs in two copies flanking a (additional) gene of interest (being located between these two transposons). The gene flanked by the two transposons may directly be linked to the transposon(s). Alternatively, the active gene(s) may be separated by a spacer sequence from the transposon(s). This spacer sequence is typically formed by a number of nucleic acids, preferably 50 to 200 nucleic acids. Furthermore, the proteins or genes encoded by the two transposons, forming the sandwich structure, may be the same or different. When combining such a "sandwich structure" with an inventive polypeptide preferably the entire sequence starting from the first transposon until the end of the second transposon, will be inserted into a target (insertion) site of the inventive polypeptide.

In further embodiments thus
the transposon according to the invention thus is part of a plasmid;
in the transposon according to the invention the nucleic acid sequence comprises an open reading frame;
in the transposon according to the invention the nucleic acid sequence comprises at least one expression control region; preferably the expression control region is selected from the group consisting of a promoter, an enhancer or a silencer;
in the transposon according to the invention the nucleic acid sequence comprises a promoter operably linked to at least a portion of an open reading frame;
the transposon according to the invention is part of a cell obtained from an animal, preferably from a vertebrate or an invertebrate, with preferably the vertebrate being selected from the group consisting of a fish, a bird, or a mammal, preferably a mammal; the transposon according to the invention is integrated into the cell DNA selected from the group consisting of the cell genome or extrachromosomal cell DNA (selected from the group consisting of an episome or a plasmid) or is autonomously replicated as part of an autonomous vector, e.g. plasmid; and/or
in the transposon according to the invention at least one of the repeats comprises at least one direct repeat.

Another embodiment of the present invention refers to a gene transfer system. As mentioned above, the inventive polypeptide preferably recognizes repeats (IRs and/or RSDs) on the inventive transposon. The gene transfer system of this invention, therefore, preferably comprises two components: the inventive polypeptide (the respective transposase) as defined above and a cloned, non-autonomous (i.e., non-self inserting) element or transposon (referred to herein as a transposon having at least two repeats (IRs and/or RSDs)) that encompasses between the repeats (IRs and/or RSDs) the transposon substrate DNA. When put together these two components of the inventive gene transfer system provide active transposon activity and allow the transposon (preferably with a gene or a sequence of interest with therapeutic, scientific or diagnostic application) to be relocated. In use, the inventive polypeptide (transposase variants) binds to the repeats (IRs and/or RSDs) of an inventive transposon and promotes insertion of the intervening nucleic acid sequence into DNA of a cell as defined below. More precisely, the inventive gene transfer system comprises an inventive transposon as defined above in combination with a polypeptide according to the invention (or nucleic acid encoding the inventive polypeptide to provide a transposase activity in a cell). Such an inventive combination preferably results in the insertion of the nucleic acid sequence into the DNA of the cell. Alternatively, it is possible to insert the transposon of the present invention into DNA of a cell through non-homologous recombination through a variety of reproducible mechanisms. In either event the inventive transposon can be used for gene transfer by using the inventive system.

Thus a further aspect of the invention refers to a gene transfer system for introducing DNA into the DNA of a cell comprising:
a) a transposon according to the invention; and
b) a polypeptide according to the invention and/or a nucleic acid according to the invention (thus encoding the polypeptide according to the invention); and/or a transposon of the invention containing a coding region for a polypeptide of the invention with improved transposase activity.

In another embodiment of the gene transfer system, being an autonomous system, the nucleic acid positioned between the at least two repeats in the transposon according to the invention, comprises the nucleic acid according to the invention encoding the polypeptide according to the invention and e.g. a nucleic acid of interest.

The inventive gene transfer system mediates insertion of the inventive transposon into the DNA of a variety of cell types and a variety of species by using the inventive polypeptide. Preferably, such cells include any cell suitable in the present context, including but not limited to animal cells or cells from bacteria, fungi (e.g., yeast, etc.) or plants. Preferred animal cells can be vertebrate or invertebrate. Preferred invertebrate cells include cells derived from crustaceans or mollusks including, but not limited to shrimp, scallops, lobster, claims, or oysters. Preferred vertebrate cells include cells from fish, birds and other animals, e.g. and preferably cells from mammals including, but not limited to, rodents, such as rats or mice, ungulates, such as cows or goats, sheep, swine or cells from a human, preferably rats, mice or humans. In a specifically preferred embodiment, cells suitable for the present invention include CHO, HeLa and COS cells.

Furthermore, such cells, particularly cells derived from a mammals as defined above, can be pluripotent (i.e., a cell whose descendants can differentiate into several restricted cell types, such as hematopoietic stem cells or other stem cells) and totipotent cells (i.e., a cell whose descendants can become any cell type in an organism, e.g., embryonic stem cells). Such cells are advantageously used in order to affirm stable expression of the inventive polypeptide (a transposase variant) or to obtain a multiple number of cells already transfected with the components of the inventive gene transfer system. Additionally, cells such as oocytes, eggs, and one or more cells of an embryo may also be considered as targets for stable transfection with the present gene transfer system.

In another aspect the invention refers to a cell producing the inventive polypeptide or to a cell containing the inventive nucleic acid or transposon.

Cells receiving the inventive transposon and/or the inventive polypeptide/protein and capable of inserting the inventive transposon into the DNA of that cell also include without being limited thereto, lymphocytes, hepatocytes, neural cells (e.g. neurons, glia cells), muscle cells, a variety of blood cells, and a variety of cells of an organism, embryonic stem cells, somatic stem cells e.g. (lympho)-hematopoietic cells, embryos, zygotes, sperm cells (some of which are open to be manipulated by an in vitro setting). More specifically, the cells derived from the hematopoietic system may be B cells, T cells, NK cells, dendritic cells, granulocytes, macrophages, platelets, erythrocytes or their (common) progenitor cells, e.g. multipotent progenitor cells, in particular long term or short term CD34+ cells of the hematopoietic system.

In this context, the cell DNA that acts as a recipient of the transposon of this invention includes any DNA present in a cell (as mentioned above) to be transfected, if the inventive transposon is in contact with an inventive polypeptide within said cell. For example, the cellular DNA can be part of the cell genome or it can be extrachromosomal, such as an episome, a plasmid, a circular or linear DNA fragment. Typical targets for insertion are e.g. cellular double-stranded DNA molecules.

The components of the inventive gene transfer system, i.e. the inventive polypeptide/protein (provided in whatever form, e.g. as such (a protein) or encoded by an inventive nucleic acid or as a component of an inventive transposon) and the inventive transposon containing a nucleotide sequence (coding for a protein of interest) can be transfected into a cell, preferably into a cell as defined above, and more preferably into the same cell. Transfection of these components may furthermore occur in subsequent order or in parallel. E.g. the inventive polypeptide, its encoding nucleic acid or a transposon containing the inventive nucleic acid, may be transfected into a cell as defined above prior to, simultaneously with or subsequent to transfection of the inventive transposon containing a nucleotide sequence (coding for a protein of interest). Alternatively, the inventive transposon may be transfected into a cell as defined above prior to, simultaneously with or subsequent to transfection of the inventive polypeptide or its encoding nucleic acid or a transposon containing the inventive nucleic acid. If transfected parallel, preferably both components are provided in a separated formulation and/or mixed with each other directly prior to administration in order to avoid transposition prior to transfection. Additionally, administration of at least one component of the gene transfer system may occur repeatedly, e.g. by administering at least one, two or multiple doses of this component, or both components.

For any of the above transfection reactions, the inventive gene transfer system may be formulated in a suitable manner as known in the art, or as a pharmaceutical composition or kit as defined below.

Furthermore, the components of the inventive gene transfer system are preferably transfected into one or more cells by techniques such as particle bombardment, electroporation, microinjection, combining the components with lipid-containing vesicles, such as cationic lipid vesicles, DNA condensing reagents (e.g., calcium phosphate, polylysine or polyethyleneimine), and inserting the components (i.e. the nucleic acids thereof) into a viral vector and contacting the viral vector with the cell. Where a viral vector is used, the viral vector can include any of a variety of viral vectors known in the art including viral vectors selected from the group consisting of a retroviral vector, an adenovirus vector or an adeno-associated viral vector.

As already mentioned above the nucleic acid encoding the inventive polypeptide may be RNA or DNA. Similarly, either the inventive nucleic acid encoding the inventive polypeptide or the transposon of this invention can be transfected into the cell as a linear fragment or as a circularized, isolated fragment or inserted into a vector, preferably as a plasmid or as recombinant viral DNA.

Furthermore, the inventive nucleic acid encoding the inventive polypeptide/protein or the transposon of the invention is thereby preferably stably or transiently inserted into the genome of the host cell to facilitate temporary or prolonged expression of the inventive polypeptide in the cell.

The present invention furthermore provides an efficient method for producing transgenic animals, including the step of applying the inventive gene transfer system to an animal.

Another embodiment of the present invention refers to a transgenic animal produced by such methods as disclosed above, preferably by using the inventive gene transfer system. Inventive transgenic animals preferably contain a nucleic acid sequence inserted into the genome of the animal by the inventive gene transfer system, thereby enabling the transgenic animal to produce its gene product, e.g. a protein. In inventive transgenic animals this protein is preferably a product for isolation from a cell. Therefore, in one alternative, inventive transgenic animals may be used as bioreactors. The inventive protein can be produced in quantity in milk, urine, blood or eggs. Promoters can be used that promote expression in milk, urine, blood or eggs and these promoters include, but are not limited to, casein promoter, the mouse urinary protein promoter, [beta]-globin promoter and the ovalbumin promoter respectively. Recombinant growth hormone, recombinant insulin, and a variety of other recombinant proteins have been produced using other methods for producing protein in a cell. Nucleic acids encoding these or other proteins can be inserted into the transposon of this invention and transfected into a cell. Efficient transfection of the inventive transposon as defined above into the DNA of a cell occurs when an inventive Polypeptide is present. Where the cell is part of a tissue or part of a transgenic animal, large amounts of recombinant protein can be obtained.

Inventive transgenic animals may be selected from vertebrates and invertebrates, selected form e.g. fish, birds, mammals including, but not limited to, rodents, such as rats or mice, ungulates, such as cows or goats, sheep, swine or humans.

The present invention furthermore provides a method of treatment for a patient in need thereof by applying the inventive gene transfer system, in which the method is an in-vivo or ex-vivo gene therapy and a nucleic acid of interest is used.

Thus the present invention furthermore provides a method for gene therapy comprising the step of introducing the inventive gene transfer system into cells as defined above. Therefore, the inventive transposon as defined above preferably comprises a gene to provide a gene therapy to a cell or an organism. Preferably, the gene is placed under the control of a tissue specific promoter or of a ubiquitous promoter or one or more other expression control regions for the expression of a gene in a cell in need of that gene. A variety of genes are being tested for a variety of gene therapies including, but not limited to, the CFTR gene for cystic fibrosis, adenosine deaminase (ADA) for immune system disorders, factors involved in blood clotting, e.g. Factor VII, VIII, factor IX and interleukin-2 (IL-2) for blood cell diseases, alpha-1-antitrypsin for lung disease, and tumor necrosis factors (TNFs). These and a variety of human or animal specific gene sequences including gene sequences to encode marker proteins and a variety of recombinant proteins are available in the known gene databases such as GenBank, and the like.

Particularly for gene therapy purposes, but also for other inventive purposes the inventive gene transfer system may be transfected into cells by a variety of methods, e.g. by microinjection, lipid-mediated strategies or by viral-mediated strategies. For example, where microinjection is used, there is very little restraint on the size of the intervening sequence of the transposon of this invention. Similarly, lipid-mediated strategies do not have substantial size limitations. However, other strategies for introducing the gene transfer system into a cell, such as viral-mediated strategies could limit the length of the nucleic acid sequence positioned between the repeats (IRs and/or RSDs), according to this invention.

In this context, the inventive gene transfer system as defined above can be delivered to cells via viruses, including retroviruses (such as lentiviruses, etc.), adenoviruses, adeno-associated viruses, herpesviruses, and others. There are several potential combinations of delivery mechanisms for the inventive transposon portion containing the transgene of interest flanked by the terminal repeats (IRs and/or RSDs) and the gene encoding the inventive polypeptide (transposase variant). For example, both, the inventive transposon and the inventive polypeptide (or transposase gene) can be contained together on the same recombinant viral genome; a single infection delivers both parts of the inventive gene transfer system such that expression of the transposase then directs cleavage of the transposon from the recombinant viral genome for subsequent insertion into a cellular chromosome. In another example, the inventive polypeptide (transposase variant) and the inventive transposon can be delivered separately by a combination of viruses and/or non-viral systems such as lipid-containing reagents. In these cases, either the transposon and/or the transposase gene can be delivered by a recombinant virus. In every case, the expressed transposase gene directs liberation of the transposon from its carrier DNA (viral genome) for insertion into chromosomal DNA.

In a specific embodiment of the present invention inventive transposons may be utilized for insertional mutagenesis, preferably followed by identification of the mutated gene. DNA transposons, particularly the inventive transposons, have several advantages compared to approaches in the prior art, e.g. with respect to viral and retroviral methods. For example, unlike proviral insertions, transposon insertions can be remobilized by supplying the transposase activity in trans. Thus, instead of performing time-consuming microinjections, it is possible according to the present invention to generate transposon insertions at new loci by crossing stocks transgenic for the above mentioned two components of the transposon system, the inventive transposon and the inventive polypeptide. In a preferred embodiment the inventive gene transfer system is directed to the germ line of the experimental animals in order to mutagenize germ cells. Alternatively, transposase expression can be directed to particular tissues or organs by using a variety of specific promoters. In addition, remobilization of a mutagenic transposon out of its insertion site can be used to isolate revertants and, if transposon excision is associated with a deletion of flanking DNA, the inventive gene transfer system may be used to generate deletion mutations. Furthermore, since transposons are composed of DNA, and can be maintained in simple plasmids, inventive transposons and particularly the use of the inventive gene transfer system is much safer and easier to work with than highly infectious retroviruses. The transposase activity can be supplied in the form of DNA, mRNA or protein as defined above in the desired experimental phase.

When the inventive gene transfer system is used in insertional mutagenesis screens, inventive transposons preferably comprise four major classes of constructs to identify the mutated genes rapidly, i.e. enhancer traps, promoter traps, polyA traps and gene traps (or exon traps) as defined below. These inventive transposons preferably contain a reporter gene, which should be expressed depending on the genetic context of the integration.

In enhancer traps, the expression of the reporter typically requires the presence of a genomic cis-regulator to act on an attenuated promoter within the integrated construct.

Promoter traps typically contain no promoter at all. In order to ensure expression of vectors, the vectors are preferably in-frame in an exon or close downstream to a promoter of an expressed gene.

In polyA traps, the marker gene preferably lacks a polyA signal, but contains a splice donor (SD) site. Thus, when integrating into an intron, a fusion transcript can be synthesized comprising the marker and the downstream exons of the trapped gene.

Gene traps (or exon traps) typically lack promoters, but are equipped with a splice acceptor (SA) preceding the marker gene. Reporter activation occurs if the vector is integrated into an expressed gene, and splicing between the reporter and an upstream exon takes place.

Finally, gene trap and polyA trap cassettes can be combined. In that case, the marker of the polyA trap part preferably carries a promoter so that the vector can also trap downstream exons, and both upstream and downstream fusion transcripts of the trapped gene can be obtained. These constructs also offer the possibility to visualize spatial and temporal expression patterns of the mutated genes by using LacZ or fluorescent proteins as a marker gene.

In a specific form of the inventive method, the present invention furthermore provides an efficient system for gene tagging by introducing a "tag" into a genomic sequence using the inventive gene transfer system. Any of the above mentioned inventive transposons, e.g. enhancer traps, promoter traps, polyA traps and gene traps (or exon traps), etc. may be used.

Due to their inherent ability to move from one chromosomal location to another within and between genomes, inventive transposons are suitable as genetic vectors for genetic manipulations in several organisms. Generally, transposon tagging is a technique in which transposons are mobilized to "hop" into genes, thereby inactivating them by insertional mutagenesis. These methods are discussed e.g. by Evans et al., TIG 1997 13, 370-374. In the inventive process, the inactivated genes are "tagged" by the transposon which then can be used to recover the mutated allele. The ability of the human and other genome projects to acquire gene sequence data has outpaced the ability of scientists to ascribe biological function to the new genes. Therefore, the present invention provides an efficient method for introducing a tag into the genome of a cell. Where the tag is inserted into a location in the cell that disrupts expression of a protein that is associated with a particular phenotype, expression of an altered phenotype in a cell containing the nucleic acid of this invention permits the association of a particular phenotype with a particular gene that has been disrupted by the transposon of this invention. Preferably, the inventive transposon as defined above functions as a tag. Primers designed to sequence the genomic DNA flanking the transposon of this invention can be used to obtain sequence information about the disrupted gene.

In a further embodiment the present invention also provides an efficient system for gene discovery, e.g. genome mapping, by introducing an inventive transposon as defined above into a gene using the inventive gene transfer system. In one example, the inventive transposon encoding a protein of interest in combination with the inventive Polypeptide or a nucleic acid encoding the inventive polypeptide or an inventive transposon containing the nucleic acid coding for the inventive polypeptide is transfected into a cell. The transposon—encoding the protein of interest—preferably comprises a nucleic acid sequence positioned between at least two repeats (IRs and/or RSDs), wherein the repeats (IRs and/or RSDs) bind to the inventive polypeptide and wherein the transposon is inserted into the DNA of the cell in the presence of the inventive polypeptide. In a preferred embodiment, the nucleic acid sequence includes a marker protein, such as GFP and a restriction endonuclease recognition site, preferably a 6-base recognition sequence. Following insertion, the cell DNA is isolated and digested with the restriction endonuclease. Where a restriction endonuclease is used that employs a 6-base recognition sequence, the cell DNA is cut into about 4000-bp fragments on average. These fragments can be either cloned or linkers can be added to the ends of the digested fragments to provide complementary sequence for PCR primers. Where linkers are added, PCR reactions are used to amplify fragments using primers from the linkers and primers binding to the direct repeats of the repeats (IRs and/or RSDs) in the transposon. The amplified fragments are then sequenced and the DNA flanking the direct repeats is used to search computer databases such as GenBank.

Using the inventive gene transfer system for methods as disclosed above such as gene discovery and/or gene tagging, permits e.g. the following:
1) identification, isolation, and characterization of genes involved with growth and development through the use of transposons as insertional mutagens (e.g., see Kaiser et al., 1995, "Eukaryotic transposons as tools to study gene structure and function." In Mobile Genetic Elements, IRL Press, pp. 69-100).
2) identification, isolation and characterization of transcriptional regulatory sequences controlling growth and development.
3) use of marker constructs for quantitative trait loci (QTL) analysis.
4) identification of genetic loci of economically important traits, besides those for growth and development, i.e., disease resistance (e.g., Anderson et al., 1996, Mol. Mar. Biol. Biotech., 5, 105-113). In one example, the system of this invention can be used to produce sterile transgenic fish. Broodstock with inactivated genes could be mated to produce sterile offspring for either biological containment or for maximizing growth rates in aquacultured fish.

The inventive gene transfer system can also be used as part of a method for working with or for screening a library of recombinant sequences, for example, to assess the function of the sequences or to screen for protein expression, or to assess the effect of a particular protein or a particular expression control region on a particular cell type. In this example, a library of recombinant sequences, such as the product of a combinatorial library or the product of gene shuffling, both techniques now known in the art and not the focus of this invention, can be inserted into the transposon of this invention encoding a protein of interest to produce a library of transposons with varying nucleic acid sequences positioned between constant repeat sequences (IRs and/or RSDs). The library is then transfected into cells together with the inventive polypeptide as discussed above.

In another embodiment of this invention, the invention provides a method for mobilizing a nucleic acid sequence in a cell. According to this method the inventive transposon is inserted into DNA of a cell, as disclosed above. Additionally, the inventive polypeptide, nucleic acid encoding the inventive polypeptide, or a transposon containing the nucleic acid coding for the inventive polypeptide, respectively, is transfected into the cell and the protein is able to mobilize (i.e. move) the transposon from a first position within the DNA of the cell to a second position within the DNA of the cell. The DNA of the cell is preferably genomic DNA or extrachromosomal DNA. The inventive method allows movement of the transposon from one location in the genome to another location in the genome, or for example, from a plasmid in a cell to the genome of that cell.

Additionally, the inventive gene transfer system can also be used as part of a method involving RNA-interference techniques. RNA interference (RNAi), is a technique in which exogenous, double-stranded RNAs (dsRNAs), being complementary to mRNA's or genes/gene fragments of the cell, are introduced into this cell to specifically bind to a particular mRNA and/or a gene and thereby diminishing or abolishing gene expression. The technique has proven effective in *Drosophila, Caenorhabditis elegans*, plants, and recently, in mammalian cell cultures. In order to apply this technique in context with the present invention, the inventive transposon preferably contains short hairpin expression cassettes encoding small interfering RNAs (siRNAs), which are complementary to mRNA's and/or genes/gene fragments of the cell. These siRNAs have preferably a length of 20 to 30 nucleic acids, more preferably a length of 20 to 25 nucleic acids and most preferably a length of 21 to 23 nucleic acids. The siRNA may be directed to any mRNA and/or a gene, that encodes any protein as defined above, e.g. an oncogene. This inventive use, particularly the use of inventive transposons for integration of siRNA vectors into the host genome advantageously provides a long-term expression of siRNA in vitro or in vivo and thus enables a long-term silencing of specific gene products.

The present invention further refers to pharmaceutical compositions containing either
- an inventive Polypeptide as such or encoded by an inventive nucleic acid, and/or
- an inventive transposon; and/or
- an inventive gene transfer system as defined above comprising an inventive polypeptide as a protein or encoded by an inventive nucleic acid, in combination with an inventive transposon.

The pharmaceutical composition may optionally be provided together with a pharmaceutically acceptable carrier, adjuvant or vehicle. In this context, a pharmaceutically acceptable carrier, adjuvant, or vehicle according to the invention refers to a non-toxic carrier, adjuvant or vehicle that does not destroy the pharmacological activity of the component(s) with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The pharmaceutical compositions of the present invention may be administered orally, parenterally, by inhalation spray, topically, rectally, nasally, buccally, vaginally or via an implanted reservoir.

The term parenteral as used herein includes subcutaneous, intravenous, intramuscular, intra-articular, intra-synovial, intrasternal, intrathecal, intrahepatic, intralesional and intracranial injection or infusion techniques. Preferably, the pharmaceutical compositions are administered orally, intraperitoneally or intravenously. Sterile injectable forms of the pharmaceutical compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavouring or colouring agents may also be added.

Alternatively, the pharmaceutically acceptable compositions of this invention may be administered in the form of suppositories for rectal administration. These can be prepared by mixing the inventive gene transfer system or components thereof with a suitable non-irritating excipient that is solid at room temperature but liquid at rectal temperature and Therefore will melt in the rectum to release the drug. Such materials include cocoa butter, beeswax and polyethylene glycols.

The pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutically acceptable compositions may be formulated in a suitable ointment containing the inventive gene transfer system or components thereof suspended or dissolved in one or more carriers. Carriers for topical administration of the components of this invention include, but are not limited to, mineral oil, liquid petrolatum, white petrolatum, propylene glycol, polyoxyethylene, polyoxypropylene component, emulsifying wax and water. Alternatively, the pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

The pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The amount of the components of the present invention that may be combined with the carrier materials to produce a composition in a single dosage form will vary depending upon the host treated, the particular mode of administration. It has to be noted that a specific dosage and treatment regimen for any particular patient will depend upon a variety of factors, including the activity of the specific component employed, the age, body weight, general health, sex, diet, time of administration, rate of excretion, drug combination, and the judgment of the treating physician and the severity of the particular disease being treated. The amount of a component of the present invention in the composition will also depend upon the particular component(s) in the composition.

The inventive pharmaceutical composition is preferably suitable for the treatment of diseases, particular diseases caused by gene defects such as cystic fibrosis, hypercholesterolemia, hemophilia, e.g. A, B, C or XIII, immune deficiencies including HIV, Huntington disease, □-anti-Trypsin deficiency, as well as cancer selected from colon cancer, melanomas, kidney cancer, lymphoma, acute myeloid leukemia (AML), acute lymphoid leukemia (ALL), chronic myeloid leukemia (CML), chronic lymphocytic leukemia (CLL), gastrointestinal tumors, lung cancer, gliomas, thyroid cancer, mamma carcinomas, prostate tumors, hepatomas, diverse virus-induced tumors such as e.g. papilloma virus induced carcinomas (e.g. cervix carcinoma), adeno carcinomas, herpes virus induced tumors (e.g. Burkitt's lymphoma, EBV induced B cell lymphoma), Hepatitis B induced tumors (Hepato cell carcinomas), HTLV-1 and HTLV-2 induced lymphoma, akustikus neurinoma, lungen cancer, pharyngeal cancer, anal carcinoma, glioblastoma, lymphoma, rectum carcinoma, astrocytoma, brain tumors, stomach cancer, retinoblastoma, basalioma, brain metastases, medullo blastoma, vaginal cancer, pancreatic cancer, testis cancer, melanoma, bladder cancer, Hodgkin syndrome, meningeoma, Schneeberger's disease, bronchial carcinoma, pituitary cancer, mycosis fungoides, gullet cancer, breast cancer, neurinoma, spinalioma, Burkitt's lymphoma, lyryngeal cancer, thymoma, corpus carcinoma, bone cancer, non-Hodgkin lymphoma, urethra cancer, CUP-syndrome, oligodendroglioma, vulva cancer, intestinal cancer, oesphagus carcinoma, small intestine tumors, craniopharyngeoma, ovarial carcinoma, ovarian cancer, liver cancer, leukemia, or cancers of the skin or the eye; etc.

The present invention finally refers to kits comprising:
an inventive polypeptide as such or encoded by an inventive nucleic acid, and/or
an inventive transposon; and/or
an inventive gene transfer system as defined above comprising an inventive polypeptide as such or encoded by an inventive nucleic acid, in combination with an inventive transposon;
optionally together with a pharmaceutically acceptable carrier, adjuvant or vehicle, and optional with instructions for use.

Any of the components of the inventive kit may be administered and/or transfected into cells in a subsequent order or in parallel. E.g. the inventive Polypeptide/protein or its encoding nucleic acid may be administered and/or transfected into a cell as defined above prior to, simultaneously with or subsequent to administration and/or transfection of the inventive transposon. Alternatively, the inventive transposon may be transfected into a cell as defined above prior to, simultaneously with or subsequent to transfection of the inventive Polypeptide or its encoding nucleic acid. If transfected parallel, preferably both components are provided in a separated formulation and/or mixed with each other directly prior to administration in order to avoid transposition prior to transfection. Additionally, administration and/or transfection of at least one component of the inventive kit may occur in a time staggered mode, e.g. by administering multiple doses of this component.

All references, patents and publications cited herein are expressly incorporated by reference into this disclosure. Particular embodiments of this invention will be discussed in detail and reference has been made to possible variations within the scope of this invention. There are a variety of alternative techniques and procedures available to those of skill in the art which would similarly permit one to successfully practice the intended invention.

DESCRIPTION OF FIGURES

FIG. 4. Hyperactive mutations forming the base for the shuffling, and their grouping to the particular restriction digestions for reducing the wt sequence content.

FIG. 7. Distribution of clone classes in the unselected library1.

FIG. 8. (A) Mutational participation of the 7 most hyperactive clones isolated from the shuffling library. (B) Particular statistical features of the selected hyperactive clones of the library.

FIG. 10: FIG. 10 shows the amino acid sequence of SB10 (SEQ. ID. NO: 1).

FIG. 11. construction of the vectors used for e.g. the experiments shown in FIGS. 14 to 26

EXAMPLES

Description of the Experimental Strategy

I.) Collecting hyperactive mutations within the SB transposase coding sequence (CDS) for the Shuffling.
  a) Mutagenesis through the whole SB CDS.
  b) Selection of hyperactives using an activity test-system.
II.) In Vitro Recombination of the Selected Mutants by DNA Shuffling.
  a) Isolation of the point mutations on 100-300 bp fragments.
  b) DNaseI breakage to 30-70 bp fragments.
  c) PCR shuffling and cloning of the library.
  d) Sequencing the library.
III.) Searching for Clones Exhibiting High Transpositional Activity.
  a) Large scale purification of shuffling clones.
  b) Test of the library clones for transpositional activity in HeLa cells.
  c) Manual creation of promising new combinations based on the sequencing data of the selected hyperactive clones In all tests for activity as a transposase described here SB10 (Ivics, Z., Hackett, P. B., Plasterk, R. H. and Izsvak, Zs. (1997) Molecular reconstruction of Sleeping Beauty, a Tc1-like transposon from fish, and its transposition in human cells. *Cell* 91:501-510) was used as a comparator.

I.a) Mutagenesis Through the Whole SB Coding Sequence.

Figure 1:
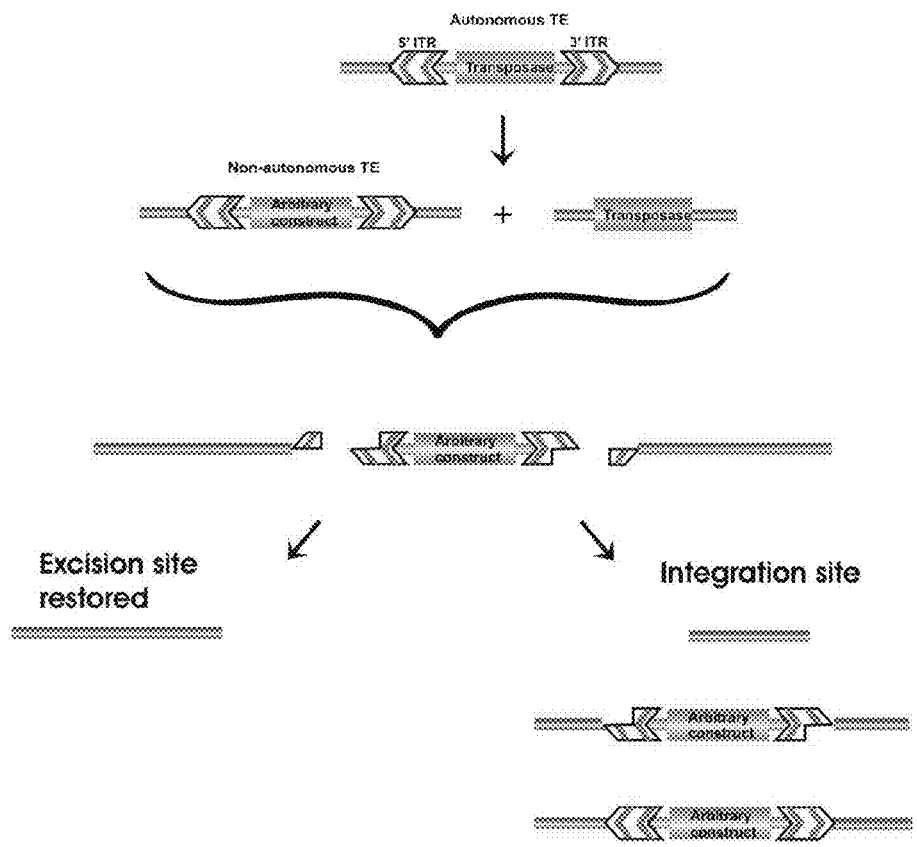
FIG. 1. Scheme of a Class II cut-and-paste transposable element (TE), the binary transposition system created by dissecting the transposase source from the transposon, and its transposition. ITR, inverted terminal repeat. TEs are moving in the host genome via a "cut-and-paste" mechanism. The mobile DNA elements are simply organized, encoding a transposase protein in their simple genome flanked by the inverted terminal repeats (ITR). The ITRs carry the transposase binding sites necessary for transposition. Their activities can easily be controlled by separating the transposase source from the transposable DNA harboring the ITRs, thereby creating a non-autonomous TE. In such a two-component system, the transposon can only move by transsupplementing the transposase protein. Practically any sequence of interest can be positioned between the ITR elements according to experimental needs. The transposition will result in excision of the element from the vector DNA and subsequent single copy integration into a new sequence environment.
Figure 2:
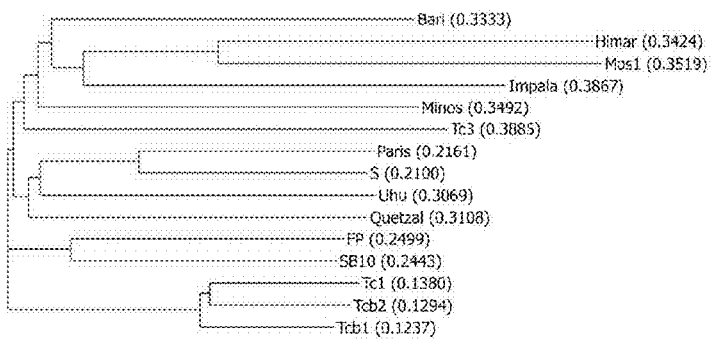
FIG. 2. A part of the protein alignment of the Tc1 transposase sequences along the whole Tc1 family with no respect of the similarity to SB. (A) Part of the alignment with one picked hyperactive AA substitution as an example. (Bari (SEQ ID NO:7); Himar (SEQ ID NO:8); Mos1 (SEQ ID NO:9); Impala (SEQ ID NO:10); Minos (SEQ ID NO:11); Tc3 (SEQ ID NO:12); Paris (SEQ ID NO:13); S (SEQ ID NO:14); Uhu (SEQ ID NO:15); Quetzal (SEQ ID NO:16); FP (SEQ ID NO:17); SB10 (SEQ ID NO:18); Tcl(SEQ ID NO:19); Tcb2 (SEQ ID NO:20); Tcb 1 (SEQ ID NO:21)). (B) Similarity tree of the alignment.
Figure 3:
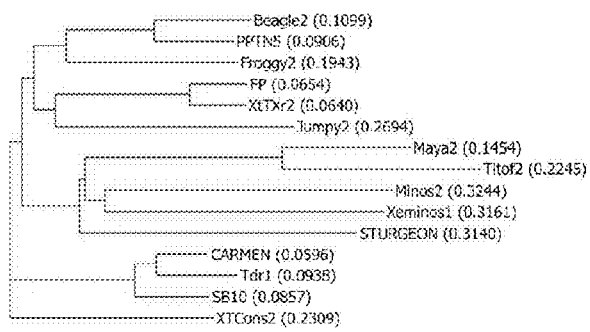
FIG. 3. A part of the protein alignment of the Tc1 transposase sequences more related to SB. (A) Part of the alignment with two picked hyperactive AA substitutions as examples. (Beagle2 (SEQ ID NO:22); PPTN5 (SEQ ID NO:23); Froggy2 (SEQ ID NO:24); FP (SEQ ID NO:25); XtTXr2 (SEQ ID NO:26); Jumpy2 (SEQ ID NO:27); Maya2 (SEQ ID NO:28); Titof2 (SEQ ID NO:29); Minos2 (SEQ ID NO:30); Xeminosl (SEQ ID NO:31); STURGEON (SEQ ID NO:32); CARMEN (SEQ ID NO:33); Tdrl (SEQ ID NO:34); SB10 (SEQ ID NO:35); XTCons2 (SEQ ID NO:36). (B) Similarity tree of the alignment.

The Tc1 family of transposons is the biggest transposon family representing a lot of related sequences available for comparison. As a first step a number of single AA substitutions were designed. A range of related transposase sequences were aligned to find promising positions to be changed in the SB CDS (coding sequence). Although emphasis was laid on getting the new AA from known active sequences, also sources with no information of their activity and some known inactive sequences were used, too. So, the transposase CDSs of other known related Tc1 transposones (FIG. 2), most of which are coding for active transposases, were aligned with SB10, followed by a second alignment with a range of other Tc1 transposase CDSs more closely related to the SB transposase sequence (compare FIG. 2B and FIG. 3B). FIG. 1A and FIG. 2A demonstrate some examples of AA substitution design using the first and the second alignments respectively.

I.b) Selection of Hyperactives Using an Activity Test-System.

The transpositional activity of all the mutations created was tested using the classical binary transposition assay (Ivics, 1997, see above). This test was the standard test for transposase activity used here. The scheme of the two component system is depicted on FIG. 1. Briefly, HeLa cells were cotransfected with the transposon vector carrying the neomycine resistance gene ($Neo^R$)) between the SB inverted repeats (pTNeo), and with the Polypeptide (transposase variant) expressing plasmid vector where the expression of the mutant SB transposases was driven by the CMV promoter. Following transfection it was selected for two weeks with G418 administration for the integration events of the $Neo^R$ transposon into the HeLa cells genome. Finally the G418 resistant colonies were stained and counted. SB10 transposase CDS were used as a control to adjust the threshold level of activity and an inactive version of the SB transposase as a negative control. The tests were performed as duplicates on 12 well tissue culture plate formats.

All the polypeptides (all single mutations) according to the invention (transposase variants) causing at least 200% hyperactivity compared to SB10 in the above assay were selected for further use in the shuffling experiment below. The hyperactivity of these variants was typically between 200-400% compared to SB10.

II.a) Isolation of the Point Mutations on 100-300 bp Fragments.

The PCR shuffling method originally published by Stemmer W.P.C. in 1994 (Stemmer, W. P. C. (1994) DNA shuffling by random fragmentation and reassembly: In vitro recombination for molecular evolution. *Proc. Natl. Acad. Sci.* 91:10747-10751) is a suitable method for mixing related parental. All the hyperactive mutations on smaller parts of the transposase CDS were isolated. The isolated fragments were broken to a 30-70 bp fragment population by DNaseI to facilitate high recombination rates.

41 single hyperactive mutations were collected to combine them in DNA shuffling (FIG. 4). The particular mutations on smaller fragments of the CDS were isolated using restriction endonucleases to reach higher average mutation number/clone. The fragment sizes and the groups of mutations isolated by the same digestions are summarized on FIG. 4. At the 5' and 3' ends of the CDS some extra flanking DNA to the fragments included to allow rebuilding the full length CDS in the shuffling. The predicted average number of mutations pro clone (see FIG. 4.) was calculated to be about 4 in the case of this particular library (FIG. 4).

II.b) DNaseI Breakage to 30-70 bp Fragments

Figure 5:
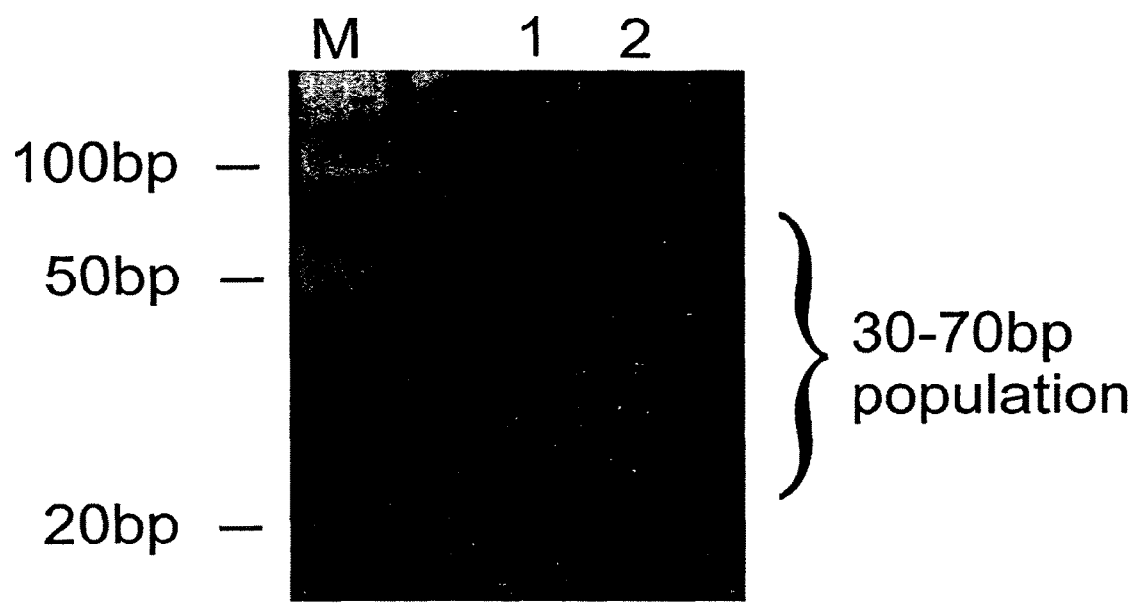
FIG. 5. DNaseI treated isolated fragment populations (lane 1 and 2) run on a 12% poly-acrylamide gel. M, marker FIG. 6. (A) PCR reassembly reaction (lane 1); M, marker. (B) Final PCR step for cloning of the full length CDS on the diluted PCR reassembly reaction template. Lane 1, forward and reverse cloning primers are added; lane 2, forward cloning primer is added; lane 3, reverse cloning primer is added; M, marker.

Next the fragments were broken in a random fashion by DNaseI digestions. The similarly sized fragments were treated in groups taking care for their same ratio in the total population. Then the mixtures of broken DNA molecules carrying the mutations were run on 12% acrylamide gels and the 30-70 bp populations of fragments were isolated. An example of the isolated fragment populations is presented on FIG. 5.

II.c) PCR Shuffling and Cloning of the Library

The isolated fragment populations were shuffled to reassemble the SB transposase CDS. Approximately the same amount of all individual mutations was used in the PCR reassembly reaction. As non-overlapping restriction fragment populations for narrowing the CDS around the mutations were used the addition of bridging oligos (for sequence see connect1-3 on Table1) was also necessary to connect the neighboring fragment groups to finally get the full length SB transposase CDS. The PCR reassembly reaction was done similarly to Stemmer, 1994, (see above). Briefly, the isolated 30-70 bp fragment populations of all the selected hyperactive mutations were added in the same ratio into the PCR reaction. The final concentration of DNA in the mixture was about 20 ng/µl. Further 2 pmol of each bridging oligos (see Table1.) was added. High-fidelity polymerase was used to minimize the introduction of further mutations created by the PCR reaction itself. The program for the PCR reassembly was the following: 1) 94° C. —60 sec, 2) 94° C. —30 sec, 3) 50° C. —30 sec, 4) 68 ° C. —1 min, 5) 68° C. —5 min, and 40 cycles has been made of the 2-4 steps. The transposase CDS reassembly to the higher molecular weight was nicely visible after 40 cycles (FIG. 6A). As the next step a second PCR reaction was carried out with the SB cloning primers SBclnfw and SBclnrev (see sequence on Table1.) using the 40× diluted assembly reaction as a template, to amplify the full length transposase CDS. The full length CDS (1023 bp) was amplified using the forward and reverse cloning primers together, in contrast to the situation when theses were added alone (FIG. 6B). The forward primer carried the recognition site of the endonuclease SpeI. and a Kozak sequence while the reverse one carried an ApaI. recognition site, besides both of the primers beard 26 bp of the very ends of the transposase CDS. This gave the possibility to efficiently clone the isolated 1023 bp product pool of the second PCR reaction into a suitable vector designed and created for the purposes of the library (data not shown) digested with the same enzymes.

TABLE I

Oligonucleotides used for the creation of the shuffling library.

| | |
|---|---|
| Connect1 | 5' gtaccacgttcatctgtacaaacaatagtacgcaagt ataa 3' SEQ ID NO: 2 |
| Connect2 | 5' cgacataagaaagccagactacggtttgcaactgcac atgggg 3' SEQ ID NO: 3 |
| Connect3 | 5' atattgaagcaacatctcaagacatcagtcaggaagt taaagcttggtcg 3' SEQ ID NO: 4 |
| SBclnfw | 5' ggtcactagtaccatgggaaaatcaaaagaaatcagc ca 3' SEQ ID NO: 5 |
| SBclnrev | 5' ggtcgggcccctagtatttggtagcattgccttta a 3' SEQ ID NO: 6 |

II.d) Sequencing the Library.

As a next step the library of the shuffling clones (see IIc) were characterized. The library was transferred into *E. Coli* DH5α competent cells, then isolated and 45 reassembled CDS fully sequenced. It was found that all the 45 CDS were full length without insertions or deletions and moreover only a very low incidence of extra mutations were observed. Only 2 specific nucleotide positions in the 1023 bp long CDS were found, where typical point mutations were inserted by the shuffling process itself into some of the clones. None of them caused AA change, and they remained silent on the protein level. After aligning the sequences to the SB10 transposase CDS the clonal distribution of the 41 mutations taken into the shuffling were identified. The incidence of the mutations was fairly statistical in the unselected library, 31 of the 41 mutations introduced into the shuffling in the 45 sequenced clones were identified (data not shown). However, the average number of mutations/clone was only about 2 mutations in contrast to the prediction (see above; FIG. 4). The reason for this is possibly the 30-70 bp length of the fragments carrying the individual mutations in the shuffling. The majority of the 41 mutations were separated from their neighboring mutations along the transposase CDS by less then 70 bp long sequences. As a consequence in the shuffling reassembly reaction the 30-70 bp fragments could partially exclude each other from a given chain elongation reaction, thereby decreasing the recombination rate between the neighboring mutations. 2 libraries were created with slight modifications in the shuffling setup (data not shown) and sequenced 23 and 22 clones of library 1 and library 2 respectively. Library 1 had 2.2 mutations/clone while library 2 had only 1.8, so library 1 was used for the further experiments. The clonal distribution of mutations in library 1 is shown on FIG. 7.

III.a) Large Scale Purification of Shuffling Clones.

The cell culture system described above was used for the activity tests. A large scale automated purification of plasmid DNA of the shuffling clones was done using a pipetting robot and a plasmid kit. The plasmid preparations were producing fairly similar yields and their quality was tissue culture compatible. All the plasmid samples were run on agarose gel to verify their similar concentrations and quality. Plasmid DNA of about 2000 clones was purified.

III.b) Test of the Library Clones for Transpositional Activity in HeLa Cells.

The clones were tested in transposition assays in HeLa cells as described in Ib) above with the difference that 96 well formats were used. All the tests were done as duplicates. For reference SB16 (Baus, 2005) was used on all the plates. All the clones that showed similar or higher activity compared to SB16 on the duplicated 96 well test plates were chosen for further operations. Further the activity of the best 20 clones on 12 well formats were verified. 7 (Variants 1 to 7) of the 20 retested clones showed clearly higher activity compared to SB16. The best 2 clones (Variants 2 and 3) exhibited about 2 times higher activity than SB16 which means about 30 times higher activity compared to SB10.

III.c) Manual Creation of Promising New Combinations Based on the Sequencing Data of the Selected Hyperactive Clones The best 20 clones retested on 12 well format and also 18 other clones still showing high activity in the range of SB16, (thus 38 clones all together), were fully sequenced to collect a data pool. The mutational content of the best 7 clones is shown in FIG. 8A. The combinations 3D5 and 6A5 (variants 2 and 3) proved to be the best showing 30-32 times higher activity compared to SB10. By analyzing the sequencing data pool of all 38 active clones it was observed that (i) the mutation number/clone is growing with the activity and it reaches the 3.6 mutations/clone as average in the group of the most hyperactive 7 clones (FIG. 8B). Moreover, (ii) it was also realized that the incidence of some of the mutations is increasing among clone groups parallel to increased transpositional activity of the groups. The most obvious example for this was the increasing incidence of the 214DAVQ (SEQ ID NO: 37)mutation (FIG. 8B). Moreover, this particular mutation appeared as the core mutation of most of the hyperactive combinations reaching or exceeding the activity range of SB16.

Among the 38 sequenced hyperactive clones only 8 containing 4 mutations and 5 containing 5 mutations were found. This means 21% and 13% incidence of 4 and 5 mutation carrying clones, respectively, in the selected library. No clones were identified bearing more than 5 mutations. Moreover, among the 7 best variants already 4 carried 4 or 5 mutations (see FIG. 8). In the unselected library the incidence of clones having 4 mutations was less then 10%. Thus, the hyperactivity in the range of SB16 really correlates well with bearing 4 or 5 mutations/clone.

Figure 9:
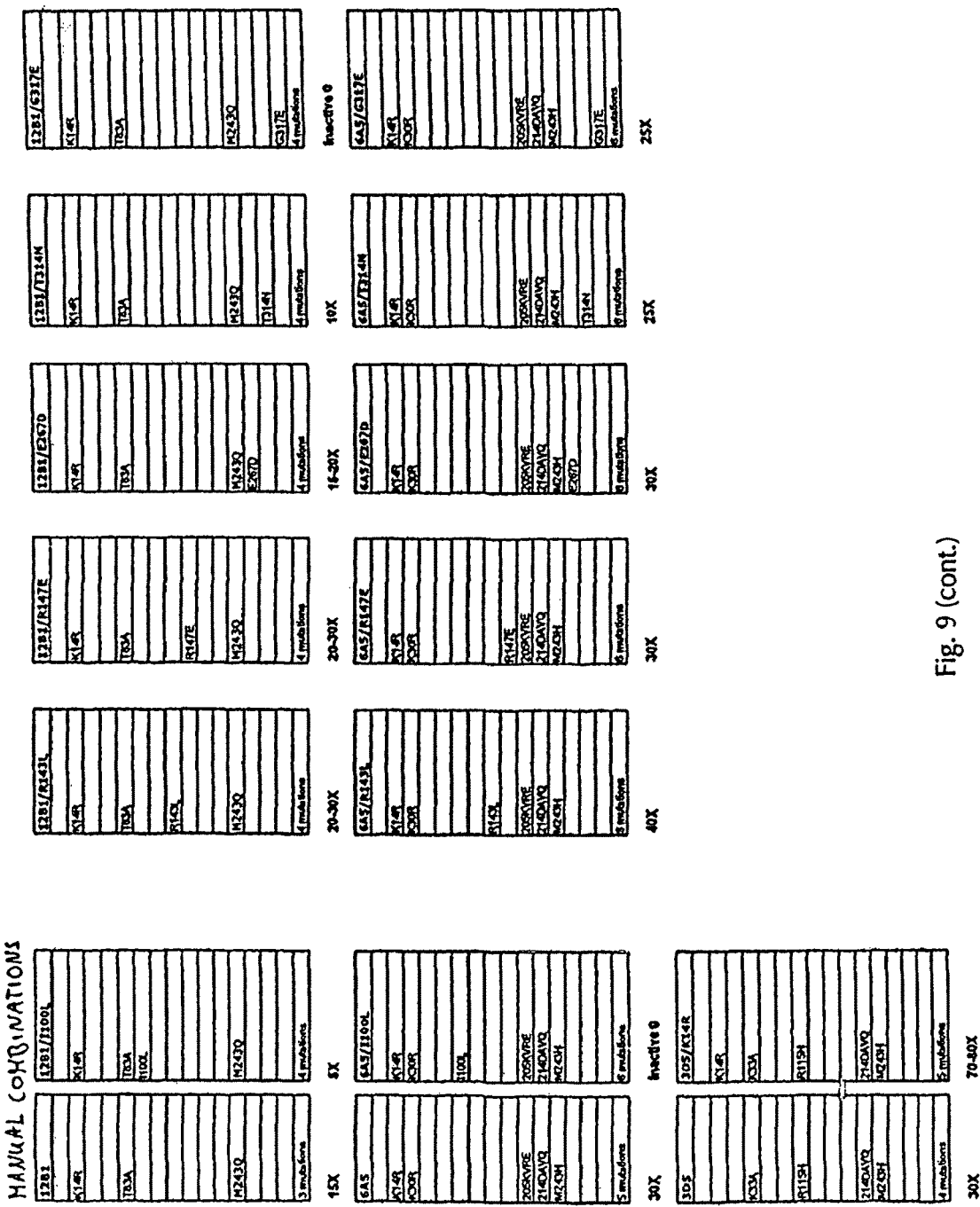
FIG. 9. Summary of our strategy for the manual improvement of the hyperactive clones harvested from the shuffling library.

After analyzing the sequencing data of the 38 most hyperactive shuffling clones 3 clones were chosen for further mutagenesis: 3D5, 6A5 and 12B1 (variants 2, 3 and 7) (FIG. 9). Also based on the sequencing data 6 "friendly" mutations were identified (FIG. 9) with the hope to successfully combining them to the 3 chosen clones. The resultant combinations and their transpositional activity were measured on 12 well formats were shown on FIG. 9 and listed in Table II. In addition, a particular clone (variant 1) was exceptionally bearing only 2 mutations. Two of these clones were identical (see 2G6 and 6G2 on FIG. 8). This exceptional combination of the K14R and the 214DAVQ (SEQ ID NO: 37)mutations was obviously not simply additive in terms of hyperactivity but it was rather a multiplier combination. Based on this observation the K14R mutation was introduced into the best 3D5 combination, by which the resultant clone containing both mutations K14R and 214 DAVQ (SEQ ID NO:37. The established clone (variant 19) showed highly enhanced activity (FIG. 9).

Overview of Transposase Activity of Tested Variants (Table II)

TABLE II

| Variant (with mutation pattern) | Activity compared to SB10 (factor) |
|---|---|
| Variant 1: K14R/R214D//K215A/E216V/N217Q; | ~20 |
| Variant 2: K33A/R115H//R214D/K215A/E216V/N217Q//M243H; | ~30 |
| Variant 3: K14R/K30R//A205K/H207V/K208R/D210E// R214D/K215A/ E216V/N217Q//M243H; | ~30 |
| Variant 4: K13D/K33A/T83A//H207V/K208R/D210E// M243Q; | ~20 |
| Variant 5: K13A/K33A//R214D/K215A/E216V/N217Q; | ~20 |
| Variant 6: K33A/T83A//R214D/K215A/E216V/N217Q// G317E; | ~20 |
| Variant 7: K14R/T83A/M243Q; | ~15 |
| Variant 8: K14R/T83A/I100L/M243Q; | ~5 |
| Variant 9: K14R/T83A/R143L/M243Q; | 20-30 |
| Variant 10: K14R/T83A/R147E/M243Q; | 20-30 |
| Variant 11: K14R/T83A/M243Q/E267D; | 15-20 |
| Variant 12: K14R/T83A/M243Q/T314N; | ~10 |

TABLE II-continued

| Variant (with mutation pattern) | Activity compared to SB10 (factor) |
|---|---|
| Variant 13: K14R/K30R/I100L//A205K/H207V/K208R/D210E// R214D/K215A/E216V/N217Q//M243H; | |
| Variant 14: K14R/K30R/R143L//A205K/H207V/K208R/D210E// R214D/K215A/E216V/N217Q//M243H; | ~40 |
| Variant 15: K14R/K30R/R147E//A205K/H207V/K208R/D210E// R214D/K215A/E216V/N217Q//M243H; | ~30 |
| Variant 16: K14R/K30R//A205K/H207V/K208R/D210E//R214D/ K215A/E216V/N217Q//M243H/E267D; | ~30 |
| Variant 17: K14R/K30R//A205K/H207V/K208R/D210E//R214D/ K215A/E216V/N217Q//M243H/T314N; | ~25 |
| Variant 18: K14R/K30R//A205K/H207V/K208R/D210E//R214D/ K215A/E216V/N217Q//M243H/G317E; | ~25 |
| Variant 19: K14R/K33A/R115H//R214D/K215A/E216V/N217Q// M243H; | 70-80 |
| Variant 20: K14R/K30R/R147E//A205K/H207V/K208R/D210E// R214D/K215A/ E216V/N217Q//M243H/T314N; | ~40 |
| Variant 21: K14R/K30R/R143L//A205K/H207V/K208R/D210E// R214D/K215A/ E216V/N217Q//M243H/E267D; | ~50 |
| Variant 22: K14R/K30R/R143L//A205K/H207V/K208R/D210E// R214D/K215A/ E216V/N217Q//M243H/T314N; | |
| Variant 23: K14R/K30R/R143L//A205K/H207V/K208R/D210E// R214D/K215A/ E216V/N217Q//M243H/G317E; | ~35 |
| Variant 24: K14R/K33A/R115H/R143L//R214D/K215A/E216V/ N217Q//M243H; | 70-80 |
| Variant 25: K14R/K33A/R115H/R147E//R214D/K215A/E216V/ N217Q//M243H; | 70-80 |
| Variant 26: K14R/K33A/R115H//R214D/K215A/E216V/N217Q// M243H/E267D; | 70-80 |
| Variant 27: K14R/K33A/R115H//R214D/K215A/E216V/N217Q// M243H/T314N; | 90-100 |
| Variant 28: K14R/K33A/R115H//R214D/K215A/E216V/N217Q// M243H/G317E; | 80-90 |
| Variant 29: K14R/T83A/M243Q/G317E; | |
| Variant 30: K13A/K33A/T83A// R214D/K215A/E216V/ N217Q | ~10 |

Further examples IV to IX were carried out with the object to determine the activity of various hyperactive transposase mutants as compared to non-hyperactive or inactive mutants (control experiments) in cell lines of various lineages (see FIGS. 14 to 26). The conditions used for these Examples are given in the following.

Description of the Experimental Strategy
Materials and Methods for Examples IV to IX
A) Sleeping Beauty Transposon System The SB transposon system is a binary system composed of (i) the inverted repeat/direct repeats (IR/DR) flanking the gene of interest, and (ii) the expression cassette encoding the transposase. Different transposons containing the gene of interest and different transposases were used in this study (see also above).

1.) SB Transposon-Based Vectors
   (i) pT2-HB-CAG-GFP

The pT2-HB-CAG-GFP transposon is a SB transposon vector in which the GFP reporter gene is transcriptionally regulated by the CAG promotor. The CAG promotor is a chimeric promoter composed of the CMV (human cytomegalovirus) immediate early enhancer in conjunction with the chicken b-actin/rabbit-b-globin hybrid promoter and intron (CAG); LMBP 2453); (pA: polyadenylation signal) (FIG. 11).

(ii) pT2-HB-CMV-FIX-neo

The pT2-HB-CMV-FIX-neo transposon is a SB transposon vector in which the human coagulation factor IX cDNA (FIX) is driven by the CMV promoter. The vector also contains a Simian Virus 40 (SV40) promoter driving a neomycin resistance gene ($Neo^R$) that confers resistance to G418 (Geneticin) in stably transfected cells (FIG. 11).

(iii) pT2-HB-CMV-GFP-neo

The pT2-HB-CMV-GFP-neo transposon is a SB transposon vector in which the GFP reporter gene is transcriptionally regulated by the CMV promotor. The vector also contains a SV40 promoter driving a neomycin resistance gene ($Neo^R$) that confers resistance to G418 (Geneticin) in stably transfected cells (FIG. 11).

(iv) pT2-HB-Apo/AAT-FIX

The pT2-HB-Apo/AAT-FIX transposon is a SB transposon vector in which the FIX cDNA was driven from the ApoE HCR/AAT promoter composed of the apolipoprotein E enhancer/al-antitrypsin promoter, the hepatocyte control region (HCR) and the first FIX intron (kindly provided by Dr. Miao, University of Washington) (FIG. 11).

2.) Transposases

Figure 12:
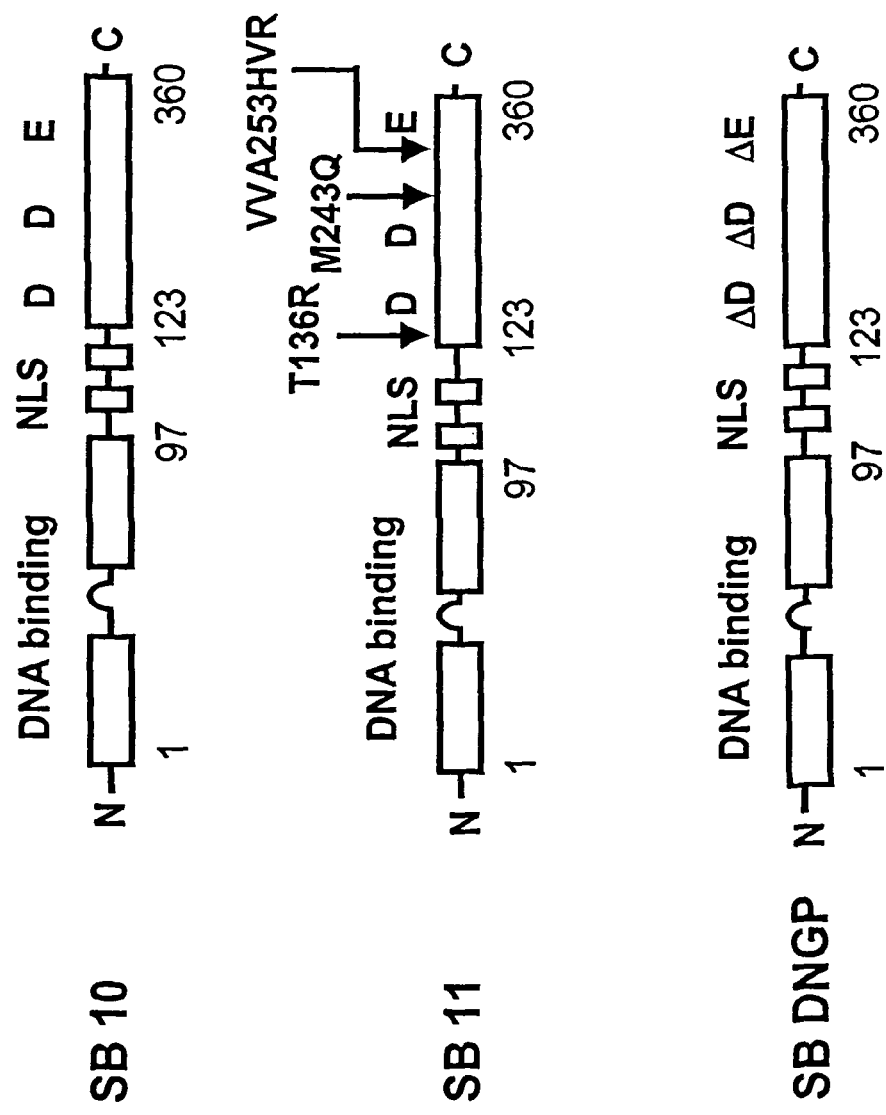
FIG. 12. overview of the non-hyperactive transposases; SB10 is the wild type transposase, SB 11 and SB DNGP are other non-hyperactive or inactive transposases having mutations over SB 10 as indicated and used herein for comparative reasons. SB10 was originally published by Ivics et al. (1997), Cell 91: 501-510 (FIG. 10), while SB 11 was originally published by Geurts et al. (2003), Mol. Therapy 8: 108-117. SB 11 contains the mutations T136R, M243Q, VVA253HVR.
Figure 13:
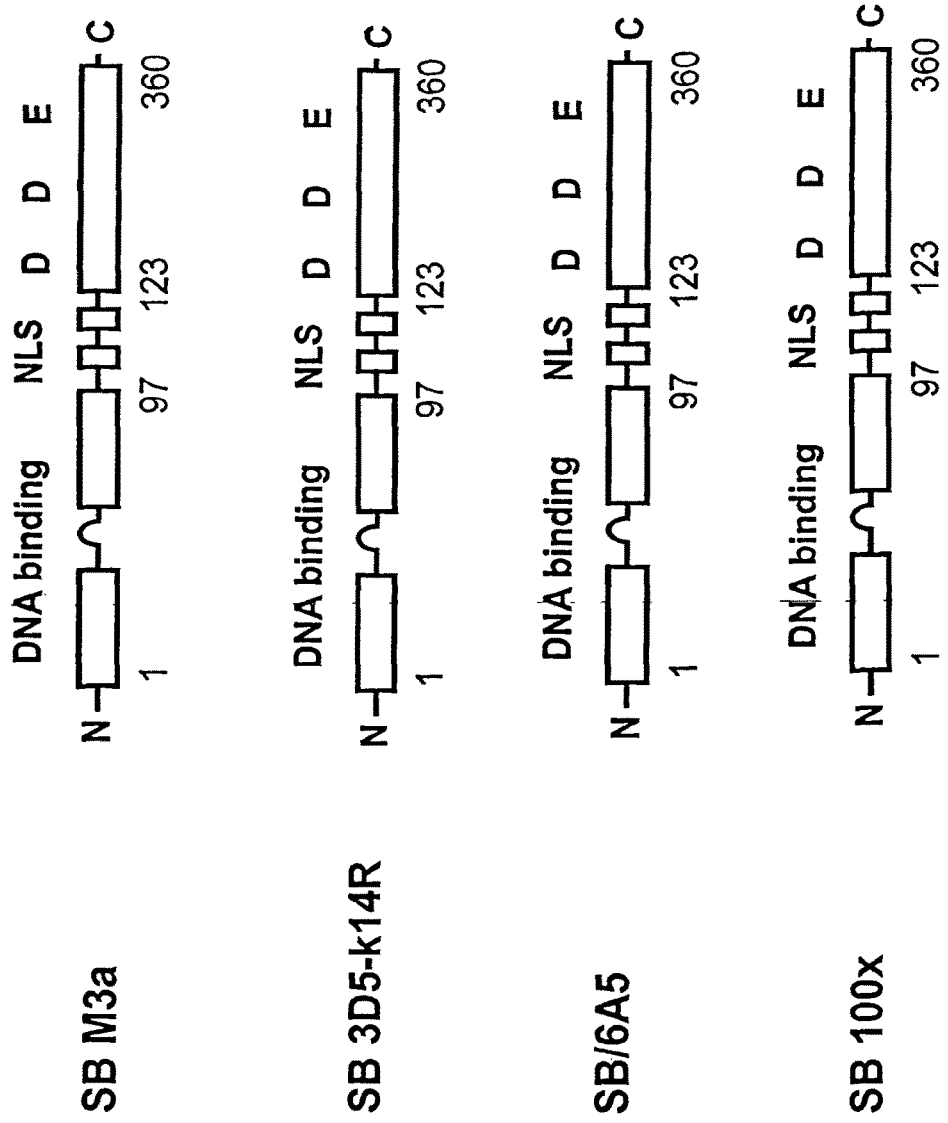
FIG. 13. overview of the hyperactive mutant transposases SB M3a (containing the mutations K13A, K33A, T83A and R214D/K215A/E216V/N217Q over SB10, Variant 30, table II), SB 3D5-K14R (Variant 19, table II), SB/6A5 (Variant 3, table II), SB 100x (Variant 27, table II), all of them derived from SB10. Preferred variants are derived from the sequence of SB10 with the mutations indicated.

All transposases (active, inactive of hyper-active) are encoded by a CMV expression plasmid and contain different mutations in the DNA binding domain, catalytic domain or both (FIGS. 12 & 13) compared to the originally reconstructed SB10 Sleeping Beauty transposase. The SB-DNGP (SEQ ID NO: 38encodes an inactive SB transposase due to the deletion of the DDE catalytic domain. To generate the SB GFP plasmid, the SB100x transposase (Variant 27) was replaced with GFP.

B) Cells

Umbilical cord blood (UCB) mononuclear cells were separated from UCB over Ficoll/Hypaque by centrifugation at 2400 rpm for 30 min at 20° C., then washed with PBS containing 2 mM EDTA and centrifuged twice at 1000 rpm for 10 min. The CD34+ cells were further enriched by immunomagnetic separation according to the manufacturer's instructions (Miltenyi Biotech Inc. CA, USA) using magnetic beads conjugated to anti-CD34 antibodies. This immunomagnetic cell separation typically yielded >95% CD34+ cells which are enriched for hematopoietic stem/progenitor (HSC) cells.

Primary human skeletal muscle stem/progenitors cells (myoblasts) were obtained by needle biopsy[5] from the vastus lateralis muscle of volunteers. Myoblasts were expanded in SkGM medium, as described by the manufacturer (Cambrex Bio Science, MD USA).

C) Mice

C57Bl/6 mice were hydrodynamically transfected with 50 micrograms of transposon with 25 μg of transposase plasmid diluted in 2 ml of PBS and injected into the tail vein. Typically, the injection took less than 10 seconds for each mouse and is results in efficient hepatic gene delivery.

D) Transfection

Nucleofection of CD34+ HSCs was done according to the optimized protocol for human CD34+ cells using the nucleofection kit developed by Aamaxa Biosystems (Amaxa Biosystems, Cologne Germany). The U-01 program was employed using the Amaxa electroporation device (Nucleofector I, Cologne Germany). Enriched CD34+ cells in PBS were centrifuged at 1200 rpm for 10 min and re-suspended in Nucleofector buffer. Typically, $1.5 \times 10^5$ cells in 100 microliter of human CD34 cell Nucleofector buffer (Amaxa Biosystems, Cologne Germany) per cuvette were subjected to electroporation with purified plasmids containing the transposon (10 microgram) and transposase (5 microgram) (concentration: 1 microgram/microliter).

Nucleofection of human muscle progenitor/stem cells (myoblasts) was done according to the optimized protocol for human myoblasts using the nucleofection kit developed by Aamaxa Biosystems (Amaxa Biosystems, Cologne Germany). The A-33 program was employed using the Amaxa electroporation device (Nucleofector I, Cologne Germany). Myoblasts in PBS were centrifuged at 1200 rpm for 10 min and resuspended in Nucleofector buffer. Typically, $10^6$ cells in 100 microliter of Primary Smooth Muscle Cell Nucleofector buffer (Amaxa Biosystems, Cologne Germany) per cuvette were subjected to electroporation with purified plasmids containing the transposon (3.6 microgram) and transposase (1.4 microgram) (concentration: 1 microgram/microliter). Transfected myoblasts were selected in G418 (400-600 microgram/ml).

E) Clonogenic Assays

1.) CFU-Mk (Megakaryocytes/Platelets)

Megakaryocytic clonogenic assays were performed by adding 50 microliter of Stemline medium (Sigma-Aldrich, USA) supplemented with SCF 100 ng/ml, IL-6 20 ng/ml, IL-3 100 ng/ml, Flt3-L 20 ng/ml and TPO 100 ng/ml to the 100 microliter of electroporated CD34+ cell suspension. Fifty microliter of the final cell suspension was then added to 450 microliter of megakaryocyte differentiation medium corresponding to Myelocult H5100 (Stemcell Technologies, Vancouver Canada) supplemented with TPO 25 ng/ml, hSCF 25 ng/ml, hIL-6 10 ng/ml, hIL1b 10 ng/ml and seeded over 3 wells in a 24-well plate, hence containing $5 \times 10^4$ cells per well. At day 6 post-transfection, medium was changed by centrifuging the plate briefly, discarding the supernatant and adding fresh megakaryocyte differentiation medium. At day 10, colonies were counted. GFP expression was monitored using the Olympus fluorescence inverted microscope and CFU-Mk colonies were scored with this microscope. In addition, the automated Zeiss Inverted Microscope was employed.

2.) CFU-GM (Granulocyte/Monocyte/Macrophage)

Granulocyte/monocyte/macrophage clonogenic assays were performed by adding 30 microliter of the final cell suspension to 270 microliter of granulocyte/monocyte/macrophage differentiation medium corresponding to semi-solid Methocult GF H4534 (Stemcell Technologies, Vancouver Canada) composed of 1% methylcellulose (4000 cps), 30% fetal bovine serum, 1% bovine serum albumin, $10^{-4}$ M 2-mercaptoethanol, 2 mM L-glutamine, 50 ng/ml rhSCF, 10 ng/ml rhGM-CSF, 10 ng/ml rhIL-3 in Iscove's MDM. The cell suspension were seeded over 3 wells in a 24-well plate, hence containing $5 \times 10^4$ cells per well. At day 14, colonies were counted. GFP expression was monitored using the Olympus fluorescence inverted microscope and CFU-GM colonies were scored with this microscope. In addition, the automated Zeiss Inverted Microscope was employed.

3.) CFU-E (Erythrocytes)

Erythroid clonogenic assays were performed by adding 30 microliter of the final cell suspension to 270 microliter of erythoid differentiation medium corresponding to semi-solid Methocult SF$^{BIT}$ H4436 (Stemcell Technologies, Vancouver Canada) composed of methylcellulose, fetal bovine serum, bovine serum albumin, 2-mercaptoethanol, L-glutamine, rhSCF, rhGM-CSF, rhIL-3, rhIL-6, rhG-CSF, rh Epo in Iscove's MDM. The cell suspension were seeded over 3 wells in a 24-well plate, hence containing $5 \times 10^4$ cells per well. At day 7, colonies were counted which typically contained about 70% glycophorin A$^+$ cells, a characteristic marker of erythroid cells. GFP expression was monitored using the Olympus fluorescence inverted microscope and CFU-E colonies were scored with this microscope. In addition the automated Zeiss Inverted Microscope was employed.

F) Detection of FIX

The level of FIX in culture supernatant or in citrated plasma was assayed for FIX antigen by Asserachrome IX sandwich ELISA (Asserachrome/Diagnostica Stago, Parsippany, N.J., USA). Blood was collected by retro-orbital bleeds.

G) Microscopy

Epifluorescence and bright field images were taken with Zeiss Axiovert 200M microscope, using the Axiovision 4.6 program and AxioCam MR3 camera. If not mentioned otherwise, pictures were taken by automatic exposure time selection and optimal display of the minimum and maximum contained gray or color value (A. Min/Max option). The settings were kept as same throughout a series of imaging and were not reset at each individual image. Confocal microscopy was carried out with Axiovert 100M, LSM510, Zeiss using the AxioPlan 2 LSM 510 version 2.8 software. In all images GFP expression was monitored at 488 nm excitation wavelength.

Examples IV to IX

Example IV

Transposition in Human CD34+ Hematopoietic Stem/Progenitor Cells

Figure 14:
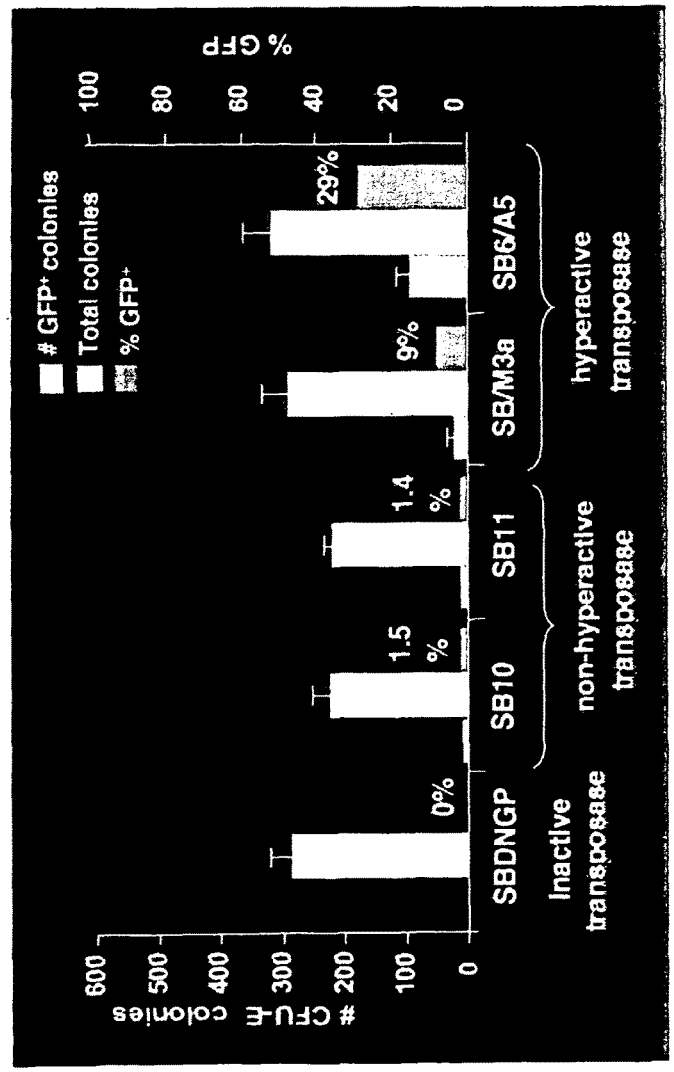
FIG. 14. comparative analysis of hyperactive transposases SB M3a, SB6/A5 versus non-hyperactive SB10 and SB11 in erythroid lineage FIG. 15. comparative analysis of hyperactive transposases M3a, SB6/A5 and SB 3D5-K14R in erythroid lineage FIG. 16. comparative analysis of hyperactive transposases SB6/A5 and SB100X in erythroid lineage FIG. 17. comparative analysis of hyperactive transposases SB6/A5 and SB100X in megakaryotic lineage FIG. 18. comparative analysis of hyperactive transposases SB6/A5 and SB100X in granulocyte/macrophage/monocyte lineage FIG. 19. relative gene transfer efficiency of transposase SB100X as compared with the hyperactive transposase SB6/A5

This Example was intended to provide a comparative analysis of hyperactive transposases SB M3a and SB6/A5, respectively, versus the non-hyperactive transposases SB10 and SB11 in erythroid lineage. Human CD34+ HSC were transfected by nucleofection with the pT2-HB-CAG-GFP and transposase expression vectors encoding SB M3a and SB 6/A5 as described in the Materila and Method section for Examples IV to IX. The performance of these novel engineered transposases was compared with that of the originally derived SB10 transposase and SB11. The total number of CFU-E colonies, the absolute number of GFP+ CFU-E colonies and the % GFP+ CFU-E colonies are shown in FIG. 14.

The results indicate that transposases SB M3a and SB 6/A5 lead to a robust increase in % GFP+ colonies compared to the originally derived SB10 transposase and SB11. In contrast, no GFP+ CFU-E colonies were detectable after co-transfection with the inactive transposase SB DNGP in which the catalytic site had been mutated. Hence, the inventive SB M3a and SB 6/A5 transposases correspond to the inventive group of "hyper-active" transposases that result in more efficient transposition in human CD34+ HSC compared to non-hyperactve transposase SB10 and SB11. The total number of CFU-E colonies remained unchanged after electroporation with the various constructs, suggesting that there is no overt toxicity associated with over-expression of these hyper-active transposases which underscores the safety of this approach.

Example V

Transposition in Human CD34/Hematopoietic Stem/Progenitor Cells

Figure 15:
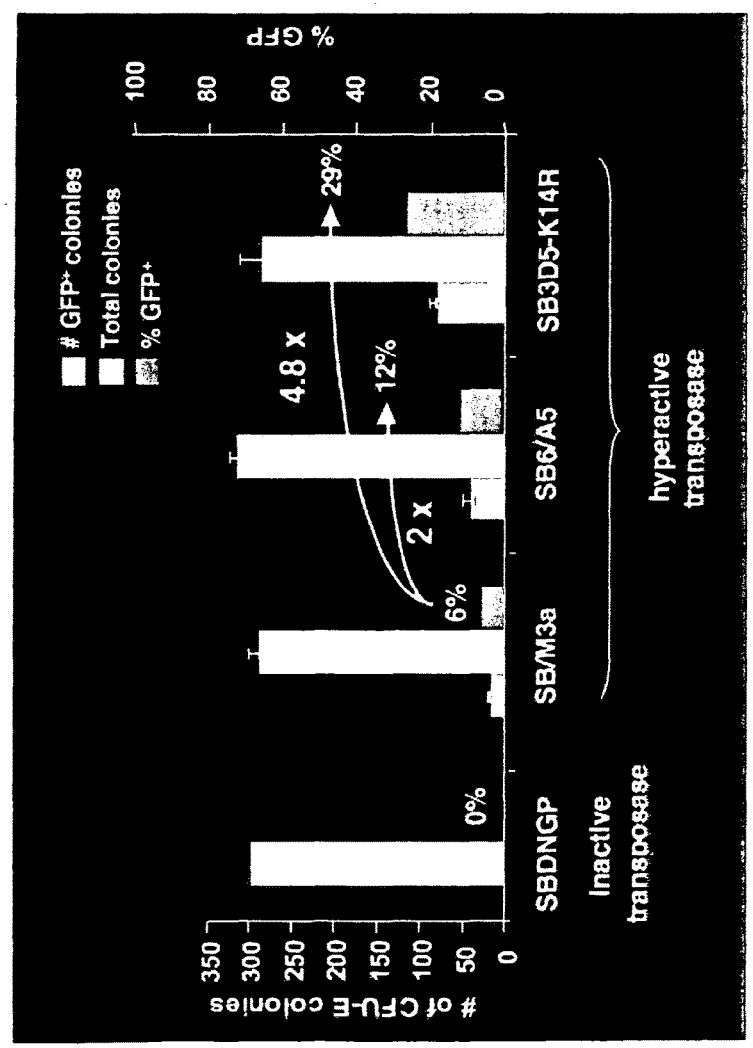

This comparative analysis was designed to determine the results of hyperactive transposases M3a, SB6/A5 and SB 3D5-K14R in erythroid lineage. Human CD34+ HSC were transfected by nucleofection with the pT2-HB-CAG-GFP and transposase expression vector encoding SB M3a, SB 6/A5 or SB 3D5-K14R, as described above. The total number of CFU-E colonies, the absolute number of GFP+ CFU-E colonies and the % GFP+ CFU-E colonies are shown in FIG. 15.

The results indicate that the transposases SB 6/A5 and SB 3D5-K14R lead to a significant increase of 2 and 4.8-fold in % GFP+ relative to the hyperactive transposase SB M3a. In contrast, no GFP+ CFU-E colonies were detectable after co-transfection with the inactive transposase SB DNGP in which the catalytic site had been mutated. This indicates that the SB 3D5-K14R results in even more robust transposition than the hyperactive SB M3a and SB 6/A5 transposases. Hence, the data shown in FIGS. 14 & 15 indicate that SB M3a, SB 6/A5 and SB 3D5-K14R correspond to the group of "hyper-active" transposases that result in more efficient gene transfer in human CD34+ HSC compared to non-hyperactive transposases SB10 and SB11. The total number of CFU-E colonies remained unchanged after electroporation with the various constructs, suggesting that there is no overt toxicity associated with over-expression of these hyper-active transposases which underscores the safety of this approach.

Example VI

Transposition in Human CD34+ Hemapoietic Stem/Progenitor Cells

Figure 16:
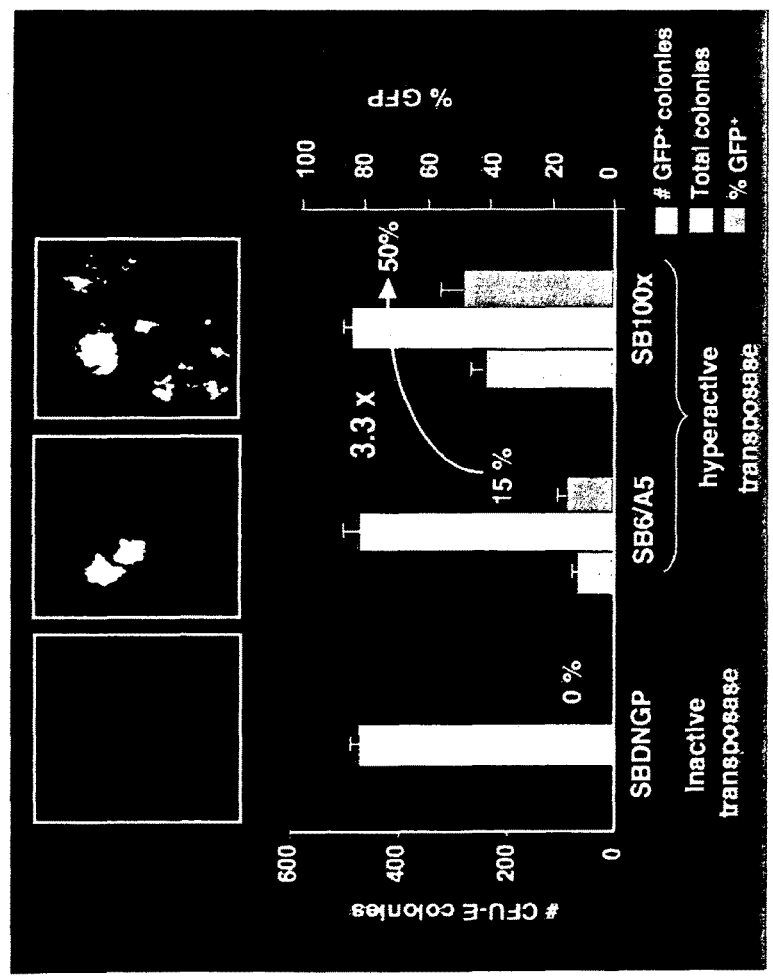
Figure 17:
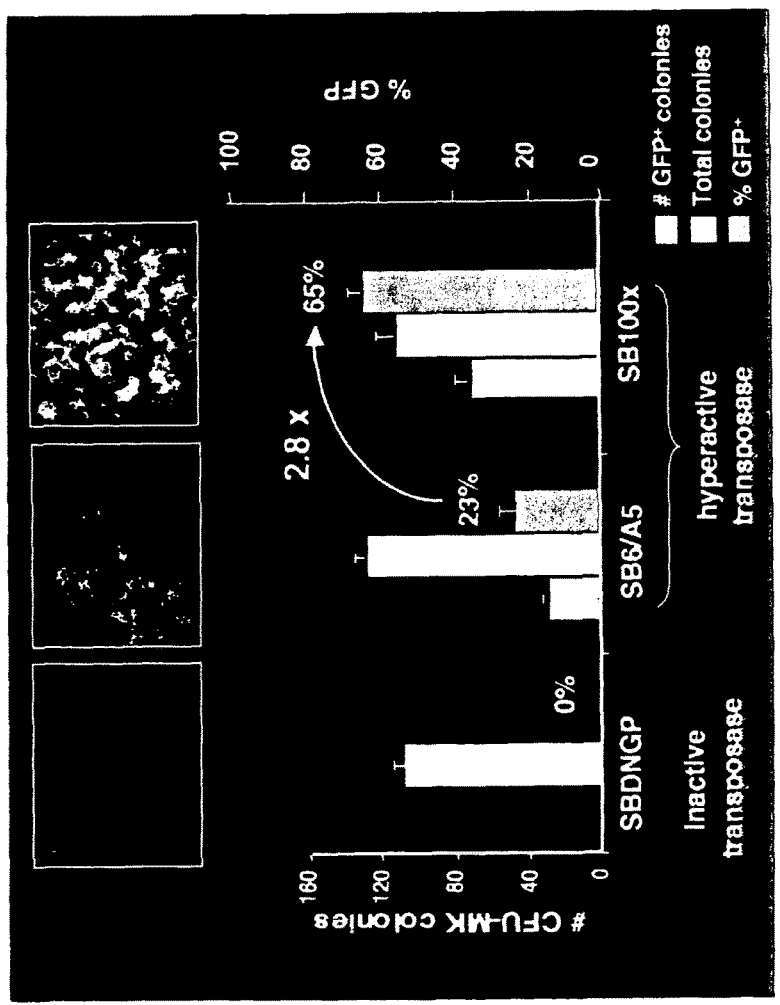
Figure 18:
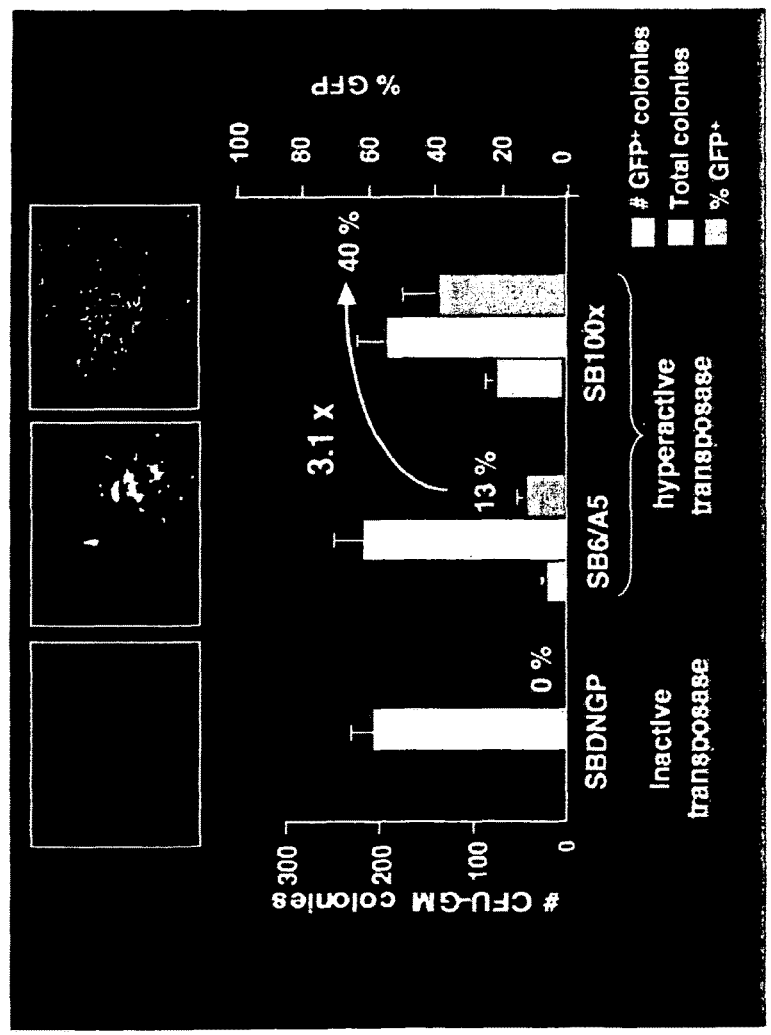
Figure 19:
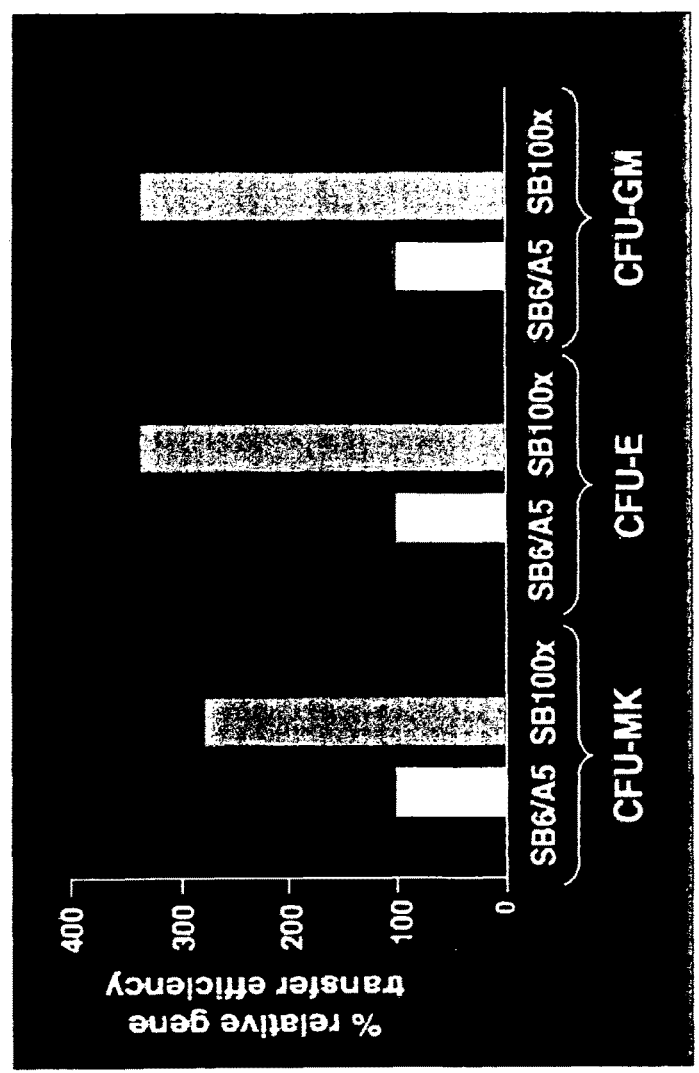

This Example was intended to provide a comparative analysis of hyperactive transposases SB6/A5 (Variant 3) versus SB100X (Variant 27) in erythroid, megakaryocytic and granulocytic/macrophage monocyte/lineage. Human CD34+ HSC were transfected by nucleofection with the pT2-HB-CAG-GFP and transposase expression vector encoding SB 6/A5 or SB 100x, as described above. The total number of CFU-E colonies, the absolute number of GFP+ CFU-E colonies and the % GFP+ CFU-E colonies are shown in FIG. 16. The total number of CFU-Mk colonies, the absolute number of GFP+ CFU-Mk colonies and the % GFP+ CFU-Mk colonies are shown in FIG. 17. The total number of CFU-GM colonies, the absolute number of GFP+ CFU-GM colonies and the % GFP+ CFU-GM colonies are shown in FIG. 18. The % relative increase in % GFP+ CFU-E, CFU-Mk and CFU-GM colonies following transposition with SB100 vs. SB 6/A5 is shown in FIG. 19.

The results indicate that the transposases SB 100x (Variant 27) lead to a robust increase in % GFP+ colonies compared to the hyperactive transposase SB 6/A5 in all lineages (CFU-E, CFU-Mk, CFU-GM). The increase in % GFP CFU's, that reflects the concomitant increase in stable gene transfer efficiencies following SB-mediated transposition, was consistent among the different lineages and hereby provides compelling evidence that a genuine hematopoietic stem/progenitor cells had been stable and efficiently transfected using this transposon technology. In contrast, no GFP+ CFU-E, CFU-Mk and CFU-GM colonies were detectable after co-transfection with the inactive transposase SB DNGP in which the catalytic site had been mutated. The total number of CFU-E, CFU-Mk and CFU-GM colonies remained unchanged after electroporation with the various constructs, suggesting that there is no overt toxicity associated with over-expression of hyper-active transposases SB100x or SB 6/A5.

Figure 20:
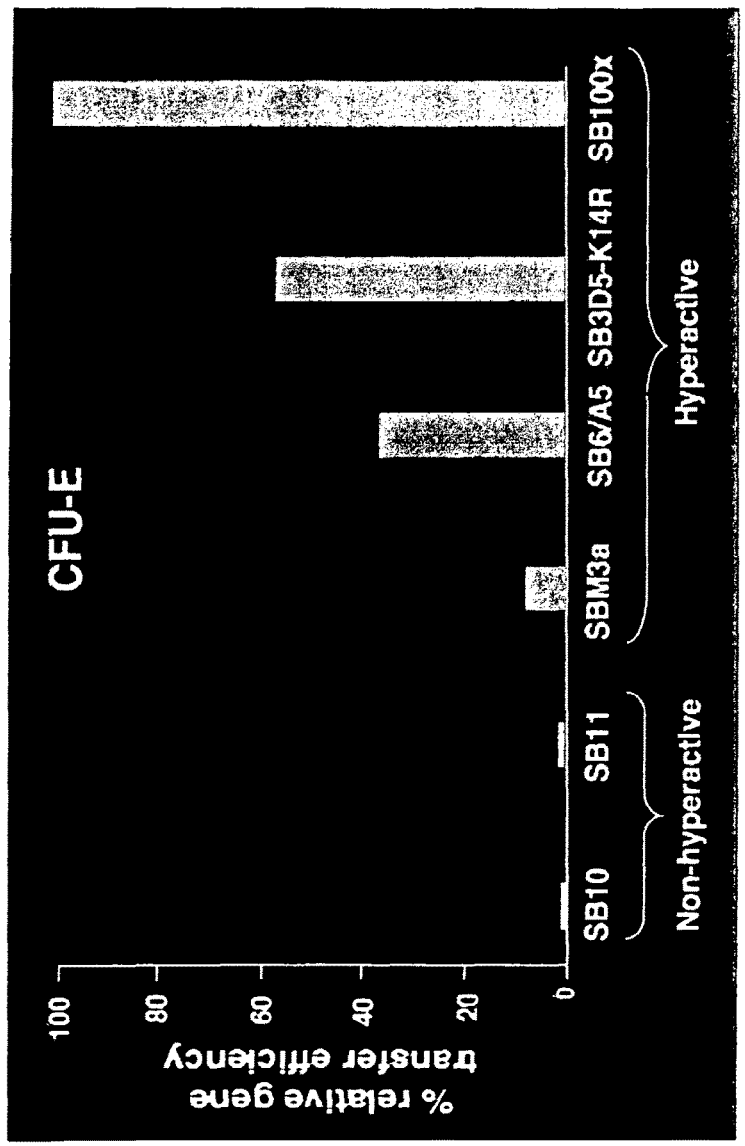
FIG. 20. relative gene transfer activity of the mutant hyperactive transposases SB M3a, SB6/A5, SB3D5-K14R and SB100X, compared to wild type transposase SB10 and the mutant non-hyperactive transposase SB11

Comparative analysis of the different transposases in the erythroid lineage indicates that all inventive hyperactive transposases (SB M3a, SB 6A5, SB 3D5-K14R and SB 100x) result in more efficient stable gene transfer in CD34+ HSCs and hence a higher % GFP+ colonies compared to when the originally derived transposase SB10 and its derivative SB11 were used (FIG. 20). The SB100x was the most efficient transposase resulting in ~100-fold increase in GFP expression and stable gene transfer efficiencies compared to SB10. This is the first demonstration of such robust stable gene transfer in primary cells, particularly lymphohematopoietic cells, including stem cells, and more in particular hematopoietic stem/progenitor cells using transposon technology. Up to now, no such high stable gene transfer efficiencies have ever been reported using a non-viral gene transfer approach in stem cells, particularly in CD34+ HSCs. These data are consistent with a recent demonstration that only a minor fraction of CD34+ HSCs can be stably transfected when non-hyperactive transposases are used consistent with the low % GFP expression in clonogenic assays (Hollis et al. Exp Hematol. 2006 October; 34(10): 1333-43) which warrants and justifies the development of hyper-active transposases as provided herein.

Example VII

Transposition in Human Muscle Stem/Progenitor Cells

Figure 21:
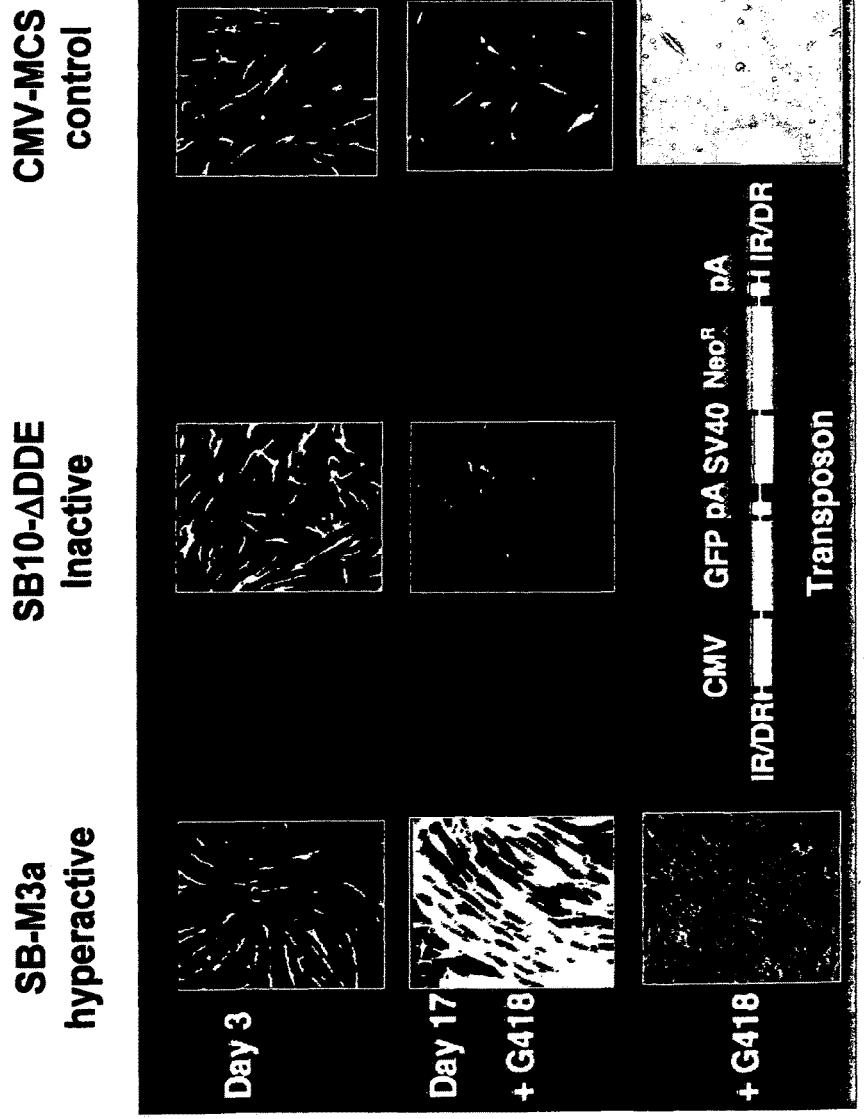
FIG. 21. Stable gene transfer efficiency in human muscle progenitor/stem cells using mutant hyperactive transposase SB M3a FIG. 22. Comparative analysis of gene transfer in human muscle progenitor/stem cells using mutant hyperactive transposase SB M3a or SB6/A5, compared with wild type transposase SB10 or mutant non-hyperactive transposase SB11
Figure 22:
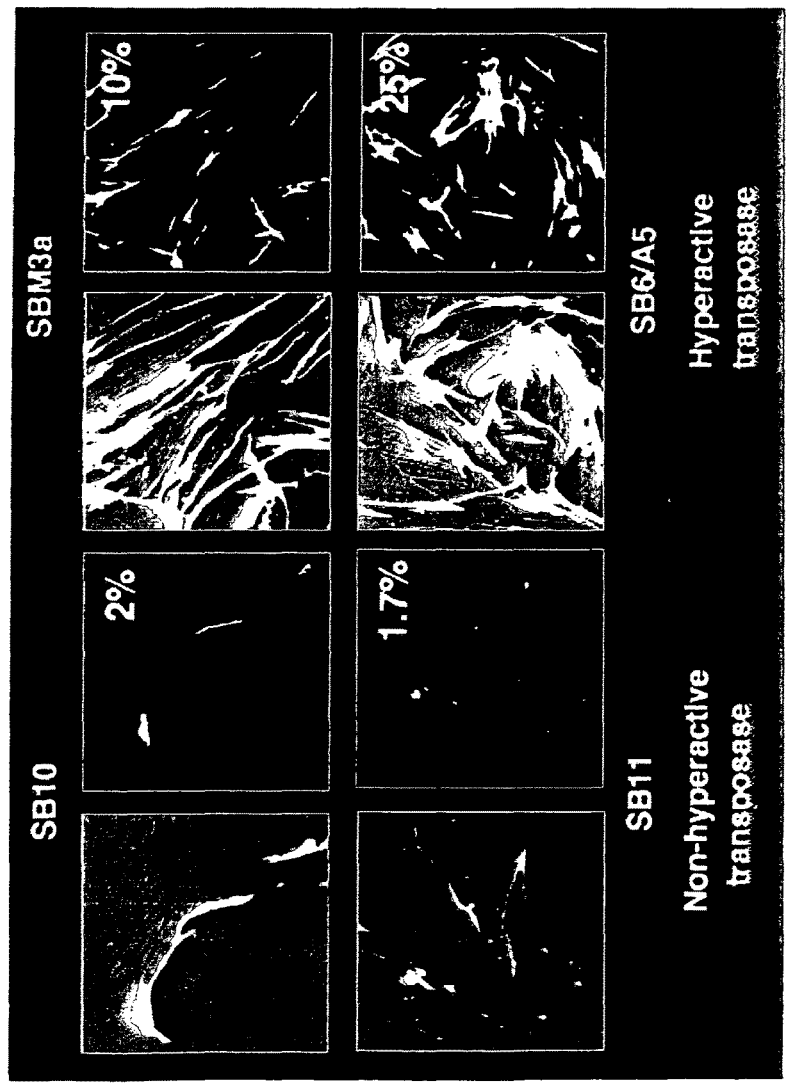

This Example was intended to validate inventive hyperactive transposases SBM3a and SB6/A5. Human muscle stem/progenitor cells (myoblasts) were transfected by nucleofection with the pT2-HB-CMV-GFP-Neo (see FIG. 11) and transposase expression vector encoding the hyperactive SB M3a transposase, as described above. Transfected cells were enriched after G418 selection. High and stable levels of GFP expression were obtained and most cells survived the G418 selection (FIG. 21). In contrast, only a limited number of GFP+ cells were detectable after cotransfection with the inactive transposase SB DNGP (SEQ ID NO: 38) in which the catalytic site had been mutated. These cells ultimately failed to survive the G418 selection consistent with poor stable gene tranfer efficiencies. Comparison of the hyperactive SB M3a transposase with the originally derived SB10 and its derivative SB11 confirm the superior transposition efficiency of SB M3a consistent with a robust increase in GFP+ transfected cells. Hence, the superior gene transfer efficiencies that can be obtained with hyperactive transposases is not unique to a given primary cell but can be extended to other cell types, including other stem/progenitor cells such as muscle stem/progenitor cells (myoblasts). This superior gene transfer potential of inventive hyperactive transposases translates into efficient and stable production of therapeutically relevant proteins like human coagulation factor IX (FIG. 22).

Example VIII

Transposition in Human Muscle Stem/Progenitor Cells

Figure 23:
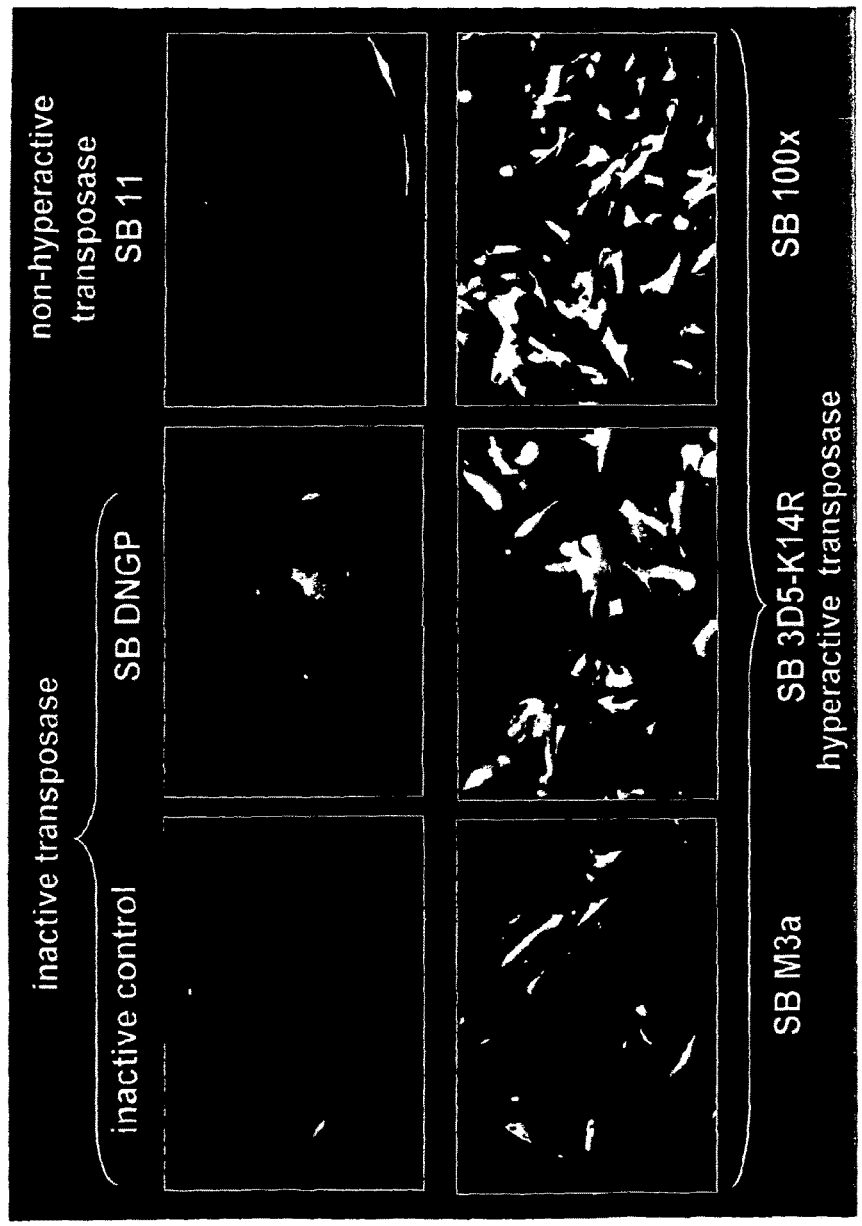
FIG. 23. Comparative analysis of hyperactive transposase SB100x, SB 3D5-K14R, SB M3a versus non-hyperactive transposase SB11 in muscle progenitor cells.

This Example serves to validate hyperactive transposases SB 100x, SB 3D5-K14R, SB M3a vs. non-hyperactive SB 11. Human muscle stem/progenitor cells (myoblasts) were transfected by nucleofection with the pT2-HB-CMV-GFP-Neo and transposase expression vector encoding the hyperactive SB 100x, SB 3D5-K14R, SB M3a transposase, vs.

non-hyperactive SB transposase (SB11) as described above. Transfected cells were enriched after G418 selection (7 days selection). High and stable levels of GFP expression were obtained and most cells survived the G418 selection (FIG. 23). In contrast, only a limited number of GFP+ cells were detectable after cotransfection with the inactive transposase SB DNGP or SB ("inactive control") in which the catalytic site had been mutated. These cells ultimately failed to thrive under G418 selection consistent with poor stable gene tranfer efficiencies. The percentage GFP+ cells was limited when the non-hyperactive SB 11 transposase was used.

Figure 24:
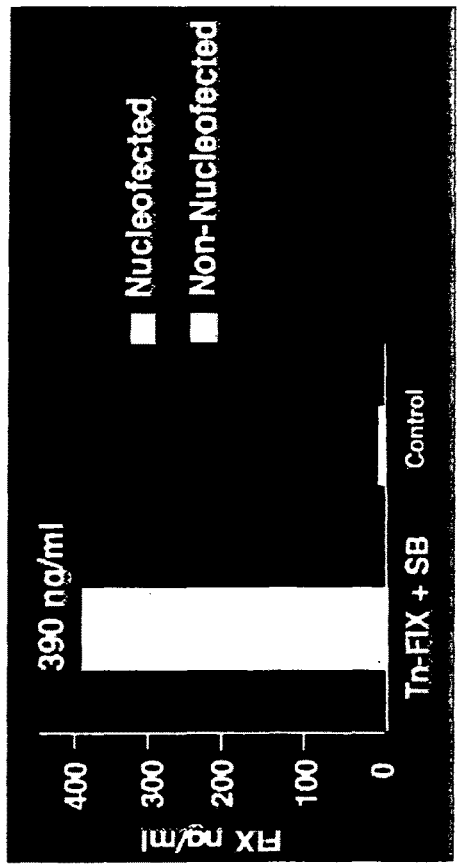
FIG. 24. Levels of Factor IX expression in human muscle progenitor cells following stable transfection using the mutant hyperactive transposase SB M3a FIG. 25. Levels of in vivo expression of Factor IX in liver of mice after transfection using the mutant hyperactive SB 100X transposase, in comparison with the mutant non-hyperactive SB11 transposase, or an inactive control.

Comparison of the hyperactive SB transposases with the SB10-derivative SB11, confirm the superior transposition efficiency of the SB 100x, SB 3D15-K14R and SB M3a, consistent with a robust increase in % GFP+ transfected cells. The SB100x transposase yielded the highest % GFP+ cells. The stable gene transfer efficiency as reflected by the % GFP cells was less when the SB 3D15 transposase was used relative to SB100x. The stable gene transfer efficiency as reflected by the % GFP cells was less with the SB M3a transposase compared to SB 3D5-K14R. Hence, the relative differences in transposition/stable gene transfer obtained with different transposases in human muscle progenitor/stem cells correlated with the relative differences in gene transfer in other primary cell types, particularly CD34 human hematopoietic stem/progenitor cells (FIG. 20). Hence, the superior gene transfer efficiencies that can be obtained with hyperactive transposases is not unique to a given primary cell but can be extended to other cell types, including other stem/progenitor cells such as muscle stem/progenitor cells (myoblasts). This superior gene transfer potential of hyperactive transposases translates into efficient and stable production of therapeutically relevant proteins like human coagulation factor IX following transfection with the SB 3D5-K14R transposase and an SB transposon containing FIX (FIG. 24).

Example IX

Transposition In Vivo

Figure 25:
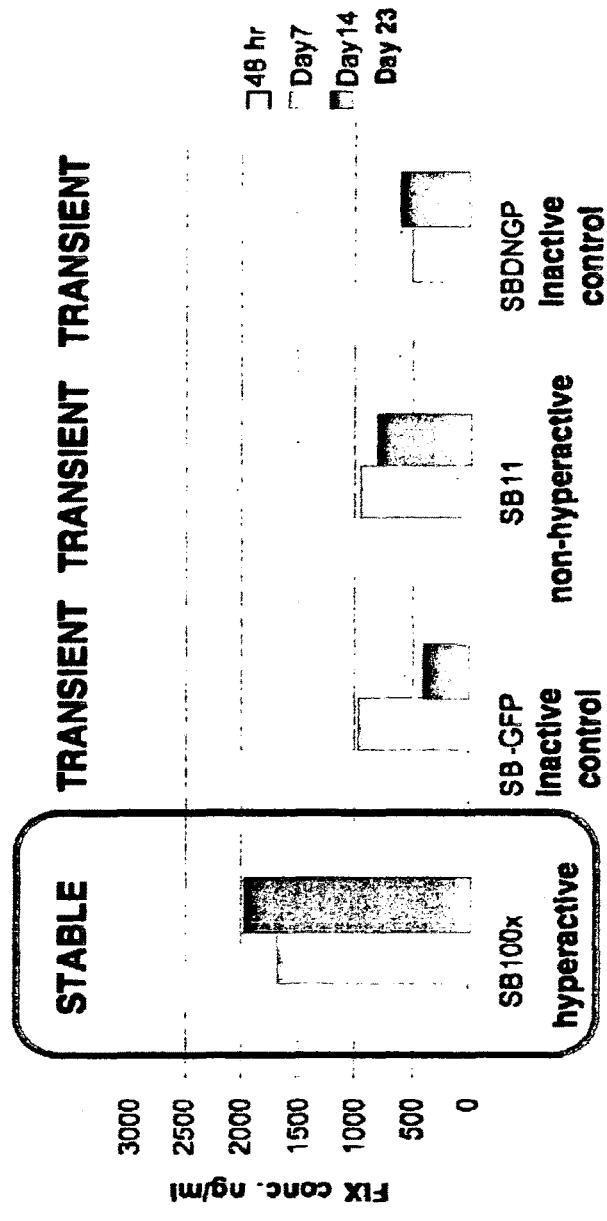

This Example was intended to validate inventive hyperactive transposase SB100X. To assess whether the hyperactive transposase SB100x also resulted in more robust gene transfer in vivo compared to when non-hyperactive transposases are used, a liver-directed gene transfer experiment was conducted as described above. To achieve this, a plasmid containing a transposon expressing factor IX (FIX) from a potent liver-specific promoter (pT2-HB-Apo/AAT-FIX) (see FIG. 11) was hydrodynamically transfected along with the transposase construct (hyperactive SB 100x vs. non-hyperactive SB 11 vs. inactive SB DNGP or SB GFP) by rapid tail vein injection in C57Bl/6 mice. Stable and high therapeutic factor IX levels were obtained when the hyperactive SB 100x was used (FIG. 25). In contrast, expression gradually declined when the inactive transposase control was employed (SB GFP). Expression of FIX following co-transfection in vivo of the FIX transposon with the hyper-active SB 100x transposase was also much more robust than when the non-hyperactive SB 11 transposase was used. Indeed, SB11-mediated transposition resulted in FIX expression that gradually declined to levels slightly above that of the control plasmid that encodes a defective transposase (SB DNGP). These results indicate that prolonged expression of FIX following SB 100x transfection in vivo could be ascribed to efficient stable transposition and hereby confirm the hyper-active transposition properties of SB 100x in vivo.

Figure 26:
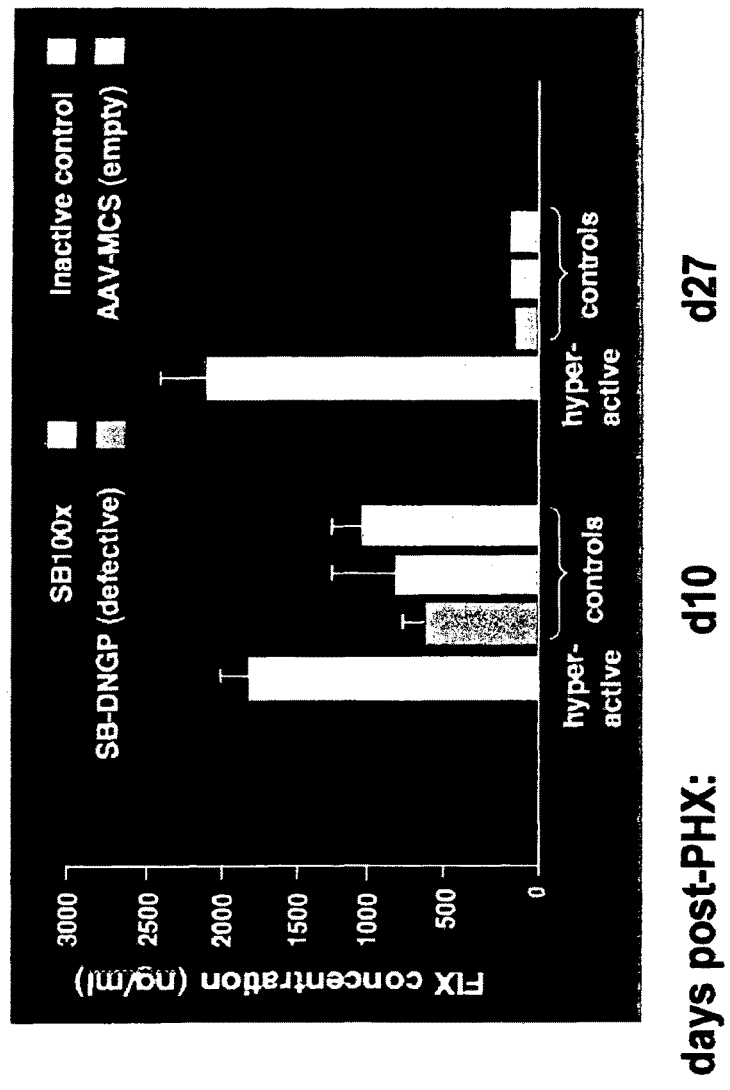
FIG. 26. Levels of in vivo expression of Factor IX in liver of mice, after transfection using the mutant hyperactive SB 100X transposase, showing a stable expression after partial hepatectomy.

To confirm that the FIX transposon had been stably integrated into the hepatocyte genome following in vivo gene transfer, hepatocyte cell cycling was induced following partial hepatectomy (Phx) (FIG. 26). This procedure consists of surgically removing 60% of the liver. In the weeks following Phx, the liver regenerates by de novo proliferation of hepatocytes until the normal liver mass had been re-established. Since Phx did not reduce the FIX levels when the SB 100x was used, it provides conclusive evidence that the transgene had integrated into the genome of the in vivo transfected hepatocytes. In contrast, FIX expression declined in the absence of stable genomic integration following hydrodynamic co-transfection of the FIX transposon with expression plasmids that encoded either an inactive transposase (SB-DNGP, inactive control) or no transposase (AAV-MCS).

The invention claimed is:

1. An isolated nucleic acid encoding sleeping beauty 10 (SB 10) polypeptide variant of SEQ ID NO: 1, wherein said variant has transpositional activity at least twice the transpositional activity of SEQ ID NO: 1, wherein the amino acid sequence of said SB 10 polypeptide variant differs from SEQ ID NO: 1 by 1 to 20 amino acids and wherein one mutation is K14R.

2. The isolated nucleic acid encoding the SB 10 polypeptide of claim 1, wherein the variant comprises 2 to 20 mutations.

3. The isolated nucleic acid encoding the SB 10 polypeptide of claim 1, wherein the SB 10 polypeptide variant comprises a combination of mutations selected from the group consisting of:
   Variant 1: K14R//R214D/K215A/E216V/N217Q;
   Variant 3: K14R/K30R//A205K/H207V/K208R/D210E// R214D/K215A/E216V/N217Q//M243H;
   Variant 7: K14R/T83A/M243Q;
   Variant 8: K14R/T83A/I100L/M243Q;
   Variant 9: K14R/T83A/R143L/M243Q;
   Variant 10: K14R/T83A/R147E/M243Q;
   Variant 11: K14R/T83A/M243Q/E267D;
   Variant 12: K14R/T83A/M243Q/T314N;
   Variant 13: K14R/K30R/I100L//A205K/H207V/K208R/ D210E//R214D/K215A/E216V/N217Q//M243H;
   Variant 14: K14R/K30R/R143L//A205K/H207V/K208R/ D210E//R214D/K215A/E216V/N217Q//M243H;
   Variant 15: K14R/K30R/R147E//A205K/H207V/K208R/ D210E//R214D/K215A/E216V/N217Q//M243H;
   Variant 16: K14R/K30R//A205K/H207V/K208R/ D210E//R214D/K215A/E216V/N217Q//M243H/ E267D;
   Variant 17: K14R/K30R//A205K/H207V/K208R/ D210E//R214D/K215A/E216V/N217Q//M243H/ T314N;
   Variant 18: K14R/K30R//A205K/H207V/K208R/ D210E//R214D/K215A/E216V/N217Q//M243H/ G317E;
   Variant 19: K14R/K33A/R115H//R214D/K215A/E216V/ N217Q//M243H;
   Variant 20: K14R/K30R/R147E//A205K/H207V/K208R/ D210E//R214D/K215A/E216V/N217Q//M243H/ T314N;
   Variant 21: K14R/K30R/R143L//A205K/H207V/K208R/ D210E//R214D/K215A/E216V/N217Q//M243H/ E267D;
   Variant 22: K14R/K30R/R143L//A205K/H207V/K208R/ D210E//R214D/K215A/E216V/N217Q//M243H/ T314N;
   Variant 23: K14R/K30R/R143L//A205K/H207V/K208R/ D210E//R214D/K215A/E216V/N217Q//M243H/ G317E;
   Variant 24: K14R/K33A/R115H/R143L//R214D/K215A/ E216V/N217Q//M243H;
   Variant 25: K14R/K33A/R115H/R147E//R214D/K215A/ E216V/N217Q//M243H;
   Variant 26: K14R/K33A/R115H//R214D/K215A/E216V/ N217Q//M243H/E267D;
   Variant 27: K14R/K33A/R115H//R214D/K215A/E216V/ N217Q//M243H/T314N;
   Variant 28: K14R/K33A/R115H//R214D/K215A/E216V/ N217Q//M243H/G317E; and
   Variant 29: K14R/T83A/M243Q/G317E.

4. The isolated nucleic acid encoding the SB10 polypeptide of claim 1, wherein the variant further comprises mutations R214D/K215A/E216V/N217Q.

5. The isolated nucleic acid encoding the SB10 polypeptide of claim 4, wherein the variant comprises a combination of mutations selected from the group consisting of:
   Variant 1: K14R//R214D/K215A/E216V/N217Q;
   Variant 3: K14R/K30R//A205K/H207V/K208R/D210E// R214D/K215A/E216V/N217Q//M243H;
   Variant 13: K14R/K30R/I100L//A205K/H207V/K208R/ D210E//R214D/K215A/E216V/N217Q//M243H;
   Variant 14: K14R/K30R/R143L//A205K/H207V/K208R/ D210E//R214D/K215A/E216V/N217Q//M243H;
   Variant 15: K14R/K30R/R147E//A205K/H207V/K208R/ D210E//R214D/K215A/E216V/N217Q//M243H;
   Variant 16: K14R/K30R//A205K/H207V/K208R/ D210E//R214D/K215A/E216V/N217Q//M243H/ E267D;
   Variant 17: K14R/K30R//A205K/H207V/K208R/ D210E//R214D/K215A/E216V/N217Q//M243H/ T314N;
   Variant 18: K14R/K30R//A205K/H207V/K208R/ D210E//R214D/K215A/E216V/N217Q//M243H/ G317E;
   Variant 19: K14R/K33A/R115H//R214D/K215A/E216V/ N217Q//M243H;
   Variant 20: K14R/K30R/R147E//A205K/H207V/K208R/ D210E//R214D/K215A/E216V/N217Q//M243H/ T314N;
   Variant 21: K14R/K30R/R143L//A205K/H207V/K208R/ D210E//R214D/K215A/E216V/N217Q//M243H/ E267D;
   Variant 22: K14R/K30R/R143L//A205K/H207V/K208R/ D210E//R214D/K215A/E216V/N217Q//M243H/ T314N;
   Variant 23: K14R/K30R/R143L//A205K/H207V/K208R/ D210E//R214D/K215A/E216V/N217Q//M243H/ G317E;
   Variant 24: K14R/K33A/R115H/R143L//R214D/K215A/ E216V/N217Q//M243H;
   Variant 25: K14R/K33A/R115H/R147E//R214D/K215A/ E216V/N217Q//M243H;
   Variant 26: K14R/K33A/R115H//R214D/K215A/E216V/ N217Q//M243H/E267D;
   Variant 27: K14R/K33A/R115H//R214D/K215A/E216V/ N217Q//M243H/T314N; and
   Variant 28: K14R/K33A/R115H//R214D/K215A/E216V/ N217Q//M243H/G317E.

6. The isolated nucleic acid encoding the SB10 polypeptide of claim 1, wherein the variant comprises a combination of mutations selected from the group consisting of:

Variant 1: K14R//R214D/K215A/E216V/N217Q;
Variant 3: K14R/K30R//A205K/H207V/K208R/D210E//R214D/K215A/E216V/N217Q//M243H;
Variant 13: K14R/K30R/I100L//A205K/H207V/K208R/D210E//R214D/K215A/E216V/N217Q//M243H;
Variant 14: K14R/K30R/R143L//A205K/H207V/K208R/D210E//R214D/K215A/E216V/N217Q//M243H;
Variant 15: K14R/K30R/R147E//A205K/H207V/K208R/D210E//R214D/K215A/E216V/N217Q//M243H;
Variant 16: K14R/K30R//A205K/H207V/K208R/D210E//R214D/K215A/E216V/N217Q//M243H/E267D;
Variant 17: K14R/K30R//A205K/H207V/K208R/D210E//R214D/K215A/E216V/N217Q//M243H/T314N;
Variant 18: K14R/K30R//A205K/H207V/K208R/D210E//R214D/K215A/E216V/N217Q//M243H/G317E;
Variant 19: K14R/K33A/R115H//R214D/K215A/E216V/N217Q//M243H;
Variant 20: K14R/K30R/R147E//A205K/H207V/K208R/D210E//R214D/K215A/E216V/N217Q//M243H/T314N;
Variant 21: K14R/K30R/R143L//A205K/H207V/K208R/D210E//R214D/K215A/E216V/N217Q//M243H/E267D;
Variant 22: K14R/K30R/R143L//A205K/H207V/K208R/D210E//R214D/K215A/E216V/N217Q//M243H/T314N;
Variant 23: K14R/K30R/R143L//A205K/H207V/K208R/D210E//R214D/K215A/E216V/N217Q//M243H/G317E;
Variant 24: K14R/K33A/R115H/R143L//R214D/K215A/E216V/N217Q//M243H;
Variant 25: K14R/K33A/R115H/R147E//R214D/K215A/E216V/N217Q//M243H;
Variant 26: K14R/K33A/R115H//R214D/K215A/E216V/N217Q//M243H/E267D;
Variant 27: K14R/K33A/R115H//R214D/K215A/E216V/N217Q//M243H/T314N; and
Variant 28: K14R/K33A/R115H//R214D/K215A/E216V/N217Q//M243H/G317E.

7. The isolated nucleic acid encoding the SB10 polypeptide of claim 1, wherein the variant comprises at least mutations
R214D/K215A/E216V/N217Q and K14R; and 2 to 6 additional mutations or groups of mutations selected from the group consisting of:
K30R;
K33A;
R115H;
R143L;
R147E;
A205K/H207V/K208R/D210E;
M243H;
E267D;
T314N; and
G317E.

8. The isolated nucleic acid encoding the SB10 polypeptide of claim 7, wherein the variant comprises a combination of mutations selected from the group consisting of mutations:
Variant 3: K14R/K30R//A205K/H207V/K208R/D210E//R214D/K215A/E216V/N217Q//M243H;
Variant 14: K14R/K30R/R143L//A205K/H207V/K208R/D210E//R214D/K215A/E216V/N217Q//M243H;
Variant 15: K14R/K30R/R147E//A205K/H207V/K208R/D210E//R214D/K215A/E216V/N217Q//M243H;
Variant 16: K14R/K30R//A205K/H207V/K208R/D210E//R214D/K215A/E216V/N217Q//M243H/E267D;
Variant 17: K14R/K30R//A205K/H207V/K208R/D210E//R214D/K215A/E216V/N217Q//M243H/T314N;
Variant 18: K14R/K30R//A205K/H207V/K208R/D210E//R214D/K215A/E216V/N217Q//M243H/G317E;
Variant 19: K14R/K33A/R115H//R214D/K215A/E216V/N217Q//M243H;
Variant 20: K14R/K30R/R147E//A205K/H207V/K208R/D210E//R214D/K215A/E216V/N217Q//M243H/T314N;
Variant 21: K14R/K30R/R143L//A205K/H207V/K208R/D210E//R214D/K215A/E216V/N217Q//M243H/E267D;
Variant 23: K14R/K30R/R143L//A205K/H207V/K208R/D210E//R214D/K215A/E216V/N217Q//M243H/G317E;
Variant 24: K14R/K33A/R115H/R143L//R214D/K215A/E216V/N217Q//M243H;
Variant 25: K14R/K33A/R115H/R147E//R214D/K215A/E216V/N217Q//M243H;
Variant 26: K14R/K33A/R115H//R214D/K215A/E216V/N217Q//M243H/E267D;
Variant 27: K14R/K33A/R115H//R214D/K215A/E216V/N217Q//M243H/T314N; and
Variant 28: K14R/K33A/R115H//R214D/K215A/E216V/N217Q//M243H/G317E.

9. The isolated nucleic acid encoding the SB10 polypeptide of claim 1, wherein the variant includes at least the following group of mutations
R214D/K215A/E216V/N217Q; and
K14R;
and 3 to 4 additional mutations selected from the group consisting of:
K33A;
R115H;
R143L;
R147E;
M243H;
E267D;
T314N;
G317E;
and 0 or 1 additional mutation selected from the group A consisting of:
R143L;
R147E;
E267D;
T314N; and
G317E.

10. The isolated nucleic acid encoding the SB10 polypeptide of claim 9, wherein the variant comprises a combination of mutations selected from the group consisting of:
Variant 19: K14R/K33A/R115H//R214D/K215A/E216V/N217Q//M243H;
Variant 24: K14R/K33A/R115H/R143L//R214D/K215A/E216V/N217Q//M243H;
Variant 25: K14R/K33A/R115H/R147E//R214D/K215A/E216V/N217Q//M243H;
Variant 26: K14R/K33A/R115H//R214D/K215A/E216V/N217Q//M243H/E267D;
Variant 27: K14R/K33A/R115H//R214D/K215A/E216V/N217Q//M243H/T314N; and Variant 28: K14R/K33A/R115H//R214D/K215A/E216V/N217Q//M243H/G317E.

11. The isolated nucleic acid encoding the SB 10 polypeptide of claim 1, wherein the variant has transpositional activity at least ten times the transpositional activity of SEQ ID NO: 1.

12. the isolated nucleic acid of claim 1, wherein the nucleic acid is RNA or DNA.

13. The isolated nucleic acid of claim 1, wherein the nucleic acid is part of a plasmid or a recombinant viral vector.

14. The isolated nucleic acid of claim 1, wherein the isolated nucleic acid additionally comprises an open reading frame.

15. The isolated nucleic acid of claim 1, wherein the isolated nucleic acid additionally comprises at least one regulatory region of a gene.

16. The isolated nucleic acid of claim 15, wherein the regulatory region is a transcriptional regulatory region.

17. The isolated nucleic acid of claim 16, wherein the regulatory region is selected from the group consisting of a promoter, an enhancer, a silencer, a locus-control region, and a border element.

18. A pharmaceutical composition comprising the isolated nucleic acid encoding the SB10 polypeptide variant of claim 1 and a pharmaceutically acceptable carrier, adjuvant or vehicle.

19. A cell comprising the isolated nucleic acid of claim 1.

* * * * *

SEQUENCE LISTING

```
<160> NUMBER OF SEQ ID NOS: 38

<210> SEQ ID NO 1
<211> LENGTH: 340
<212> TYPE: PRT
<213> ORGANISM: unknown
<220> FEATURE:
<223> OTHER INFORMATION: SB10 transposase (see Fig. 10)

<400> SEQUENCE: 1

Met Gly Lys Ser Lys Glu Ile Ser Gln Asp Leu Arg Lys Lys Ile Val
1               5                   10                  15

Asp Leu His Lys Ser Gly Ser Ser Leu Gly Ala Ile Ser Lys Arg Leu
            20                  25                  30

Lys Val Pro Arg Ser Ser Val Gln Thr Ile Val Arg Lys Tyr Lys His
        35                  40                  45

His Gly Thr Thr Gln Pro Ser Tyr Arg Ser Gly Arg Arg Val Leu
    50                  55                  60

Ser Pro Arg Asp Glu Arg Thr Leu Val Arg Lys Val Gln Ile Asn Pro
65                  70                  75                  80
```

-continued

Arg Thr Thr Ala Lys Asp Leu Val Lys Met Leu Glu Glu Thr Gly Thr
                85                  90                  95

Lys Val Ser Ile Ser Thr Val Lys Arg Val Leu Tyr Arg His Asn Leu
            100                 105                 110

Lys Gly Arg Ser Ala Arg Lys Lys Pro Leu Leu Gln Asn Arg His Lys
        115                 120                 125

Lys Ala Arg Leu Arg Phe Ala Thr Ala His Gly Asp Lys Asp Arg Thr
    130                 135                 140

Phe Trp Arg Asn Val Leu Trp Ser Asp Glu Thr Lys Ile Glu Leu Phe
145                 150                 155                 160

Gly His Asn Asp His Arg Tyr Val Trp Arg Lys Gly Glu Ala Cys
                165                 170                 175

Lys Pro Lys Asn Thr Ile Pro Thr Val Lys His Gly Gly Ser Ile
            180                 185                 190

Met Leu Trp Gly Cys Phe Ala Ala Gly Gly Thr Gly Ala Leu His Lys
        195                 200                 205

Ile Asp Gly Ile Met Arg Lys Glu Asn Tyr Val Asp Ile Leu Lys Gln
    210                 215                 220

His Leu Lys Thr Ser Val Arg Lys Leu Lys Leu Gly Arg Lys Trp Val
225                 230                 235                 240

Phe Gln Met Asp Asn Asp Pro Lys His Thr Ser Lys Val Val Ala Lys
                245                 250                 255

Trp Leu Lys Asp Asn Lys Val Lys Val Leu Glu Trp Pro Ser Gln Ser
            260                 265                 270

Pro Asp Leu Asn Pro Ile Glu Asn Leu Trp Ala Glu Leu Lys Lys Arg
        275                 280                 285

Val Arg Ala Arg Arg Pro Thr Asn Leu Thr Gln Leu His Gln Leu Cys
    290                 295                 300

Gln Glu Glu Trp Ala Lys Ile His Pro Thr Tyr Cys Gly Lys Leu Val
305                 310                 315                 320

Glu Gly Tyr Pro Lys Arg Leu Thr Gln Val Lys Gln Phe Lys Gly Asn
                325                 330                 335

Ala Thr Lys Tyr
            340

<210> SEQ ID NO 2
<211> LENGTH: 41
<212> TYPE: DNA
<213> ORGANISM: artificial
<220> FEATURE:
<223> OTHER INFORMATION: Connect1 (see description page 56)

<400> SEQUENCE: 2
gtaccacgtt catctgtaca aacaatagta cgcaagtata a                          41

<210> SEQ ID NO 3
<211> LENGTH: 43
<212> TYPE: DNA
<213> ORGANISM: artificial
<220> FEATURE:
<223> OTHER INFORMATION: Connect2 (see description page 56)

<400> SEQUENCE: 3
cgacataaga aagccagact acggtttgca actgcacatg ggg                        43

<210> SEQ ID NO 4
<211> LENGTH: 50

-continued

```
<212> TYPE: DNA
<213> ORGANISM: artificial
<220> FEATURE:
<223> OTHER INFORMATION: Connect3 (see description page 56)

<400> SEQUENCE: 4
atattgaagc aacatctcaa gacatcagtc aggaagttaa agcttggtcg      50

<210> SEQ ID NO 5
<211> LENGTH: 39
<212> TYPE: DNA
<213> ORGANISM: artificial
<220> FEATURE:
<223> OTHER INFORMATION: SBclnfw (see description page 56)

<400> SEQUENCE: 5
ggtcactagt accatgggaa atcaaaaga aatcagcca                   39

<210> SEQ ID NO 6
<211> LENGTH: 36
<212> TYPE: DNA
<213> ORGANISM: artificial
<220> FEATURE:
<223> OTHER INFORMATION: SBclnrev (see description page 56).

<400> SEQUENCE: 6
ggtcgggccc ctagtatttg gtagcattgc cttta                      36

<210> SEQ ID NO 7
<211> LENGTH: 56
<212> TYPE: PRT
<213> ORGANISM: unknown
<220> FEATURE:
<223> OTHER INFORMATION: Bari (see Fig. 2)

<400> SEQUENCE: 7

His Leu Lys Asn Asn Gln Lys His Leu Ala Ala Gln Pro Thr Asn Arg
1               5                   10                  15

Phe Gly Gly Gly Thr Val Met Phe Trp Gly Cys Leu Ser Tyr Tyr Gly
                20                  25                  30

Phe Gly Asp Leu Val Pro Ile Glu Gly Thr Leu Asn Gln Asn Gly Tyr
            35                  40                  45

Leu Leu Ile Leu Asn Asn His Ala
    50                  55

<210> SEQ ID NO 8
<211> LENGTH: 60
<212> TYPE: PRT
<213> ORGANISM: unknown
<220> FEATURE:
<223> OTHER INFORMATION: Himar (see Fig. 2)

<400> SEQUENCE: 8

Ala Glu Trp Thr Ala Thr Gly Glu Pro Ser Pro Lys Arg Gly Lys Thr
1               5                   10                  15

Gln Lys Ser Ala Gly Lys Val Met Ala Ser Val Phe Phe Asp Ala His
                20                  25                  30

Gly Ile Ile Phe Ile Asp Tyr Leu Glu Lys Gly Lys Thr Ile Asn Ser
            35                  40                  45

Asp Tyr Tyr Met Ala Leu Leu Glu Arg Leu Lys Val
    50                  55                  60

<210> SEQ ID NO 9
```

-continued

```
<211> LENGTH: 59
<212> TYPE: PRT
<213> ORGANISM: unknown
<220> FEATURE:
<223> OTHER INFORMATION: Mos1 (see Fig. 2)

<400> SEQUENCE: 9

Ser Tyr Val Asp Pro Gly Gln Pro Ala Thr Ser Thr Ala Arg Pro Asn
1               5                   10                  15

Arg Phe Gly Lys Lys Thr Met Leu Cys Val Trp Trp Asp Gln Ser Gly
            20                  25                  30

Val Ile Tyr Tyr Glu Leu Leu Lys Pro Gly Glu Thr Val Asn Thr Ala
        35                  40                  45

Arg Tyr Gln Gln Gln Leu Ile Asn Leu Asn Arg
    50                  55

<210> SEQ ID NO 10
<211> LENGTH: 52
<212> TYPE: PRT
<213> ORGANISM: unknown
<220> FEATURE:
<223> OTHER INFORMATION: Impala (see Fig. 2)

<400> SEQUENCE: 10

Phe Leu Ser Pro Arg Glu Pro Tyr Ala Tyr Arg Met Phe Lys Lys Leu
1               5                   10                  15

Gly Gly Arg Ser Cys Arg Gln Met Phe Trp Ala Ala Phe Gly His Arg
            20                  25                  30

Ser Arg Thr Pro Leu Val Pro Leu Val Gly Lys Leu Asn Ala Ile Gly
        35                  40                  45

Ile Tyr Glu Leu
    50

<210> SEQ ID NO 11
<211> LENGTH: 57
<212> TYPE: PRT
<213> ORGANISM: unknown
<220> FEATURE:
<223> OTHER INFORMATION: Minos (see Fig. 2)

<400> SEQUENCE: 11

Ile Arg Lys Arg Ser Glu Thr Tyr His Lys Asp Cys Leu Lys Arg Thr
1               5                   10                  15

Thr Lys Phe Pro Ala Ser Thr Met Val Trp Gly Cys Met Ser Ala Lys
            20                  25                  30

Gly Leu Gly Lys His Leu Phe Ile Glu Gly Thr Val Asn Ala Glu Lys
        35                  40                  45

Tyr Ile Asn Ile Leu Gln Asp Ser Leu
    50                  55

<210> SEQ ID NO 12
<211> LENGTH: 55
<212> TYPE: PRT
<213> ORGANISM: unknown
<220> FEATURE:
<223> OTHER INFORMATION: Tc3 (see Fig. 2)

<400> SEQUENCE: 12

Trp Arg Asp Leu Arg Lys Glu Pro Met Val Phe Ser Arg Arg Asn Phe
1               5                   10                  15

Gly Gly Gly Thr Val Met Val Trp Gly Ala Phe Thr Glu Lys Lys Lys
            20                  25                  30
```

```
Leu Glu Ile Gln Phe Val Ser Ser Lys Met Asn Ser Thr Asp Tyr Gln
        35                  40                  45

Asn Val Leu Glu Leu Glu Leu
    50                  55

<210> SEQ ID NO 13
<211> LENGTH: 58
<212> TYPE: PRT
<213> ORGANISM: unknown
<220> FEATURE:
<223> OTHER INFORMATION: Paris (see Fig. 2)

<400> SEQUENCE: 13

Trp Arg Lys Pro Asn Thr Ala Leu Glu Gln Lys Asn Ile Ile Pro Thr
1               5                  10                  15

Val Lys Phe Gly Lys Leu Ser Val Met Val Trp Gly Cys Ile Ser Ser
            20                  25                  30

Lys Gly Val Gly Glu Leu Arg Ile Phe Asn Asp Val Met Thr Lys Glu
        35                  40                  45

Phe Tyr Leu Asp Ile Leu Lys Asn Glu Leu
    50                  55

<210> SEQ ID NO 14
<211> LENGTH: 58
<212> TYPE: PRT
<213> ORGANISM: unknown
<220> FEATURE:
<223> OTHER INFORMATION: S (see Fig. 2)

<400> SEQUENCE: 14

Trp Arg Lys Pro Leu Ser Ala Leu Glu Thr Gln Asn Ile Ile Pro Thr
1               5                  10                  15

Ile Lys Phe Gly Lys Leu Ser Val Met Ile Trp Gly Cys Ile Ser Ser
            20                  25                  30

His Gly Val Gly Lys Leu Ala Phe Ile Glu Ser Thr Met Asn Ala Val
        35                  40                  45

Gln Tyr Leu Asp Ile Leu Lys Thr Asn Leu
    50                  55

<210> SEQ ID NO 15
<211> LENGTH: 57
<212> TYPE: PRT
<213> ORGANISM: unknown
<220> FEATURE:
<223> OTHER INFORMATION: Uhu (see Fig. 2)

<400> SEQUENCE: 15

Arg Arg Gln Ser Asn Thr Glu Leu Asn Pro Lys Asn Leu Lys Ala Thr
1               5                  10                  15

Val Lys His Gly Gly Ser Val Met Val Trp Ala Cys Ile Ser Ala Ala
            20                  25                  30

Ser Val Gly Asn Leu Val Cys Ile Glu Thr Thr Thr Asp Arg Asn Val
        35                  40                  45

Asp Leu Ser Ile Leu Lys Glu Asn Leu
    50                  55

<210> SEQ ID NO 16
<211> LENGTH: 58
<212> TYPE: PRT
<213> ORGANISM: unknown
<220> FEATURE:
```

<223> OTHER INFORMATION: Quetzal (see Fig. 2)

<400> SEQUENCE: 16

Trp Arg Pro Pro Gly Glu Gly Leu Asn Pro Lys Tyr Thr Ala Lys Thr
1               5                   10                  15

Val Lys His Asn Gly Gly Gly Val Leu Val Trp Gly Cys Met Ala Ala
            20                  25                  30

Asn Gly Val Gly Asn Leu Gln Val Ile Asp Gly Ile Met Asp Gln Tyr
        35                  40                  45

Val Tyr Ile Asn Ile Leu Lys Gln Asn Leu
    50                  55

<210> SEQ ID NO 17
<211> LENGTH: 58
<212> TYPE: PRT
<213> ORGANISM: unknown
<220> FEATURE:
<223> OTHER INFORMATION: FP (see Fig. 2)

<400> SEQUENCE: 17

Trp Arg Arg Arg Asn Thr Ala Phe His Lys Lys Asn Ile Ile Pro Thr
1               5                   10                  15

Val Lys Tyr Gly Gly Gly Ser Val Met Val Trp Gly Cys Phe Ala Ala
            20                  25                  30

Ser Gly Pro Gly Arg Leu Ala Val Ile Lys Gly Thr Met Asn Ser Ala
        35                  40                  45

Val Tyr Gln Glu Ile Leu Lys Glu Asn Val
    50                  55

<210> SEQ ID NO 18
<211> LENGTH: 58
<212> TYPE: PRT
<213> ORGANISM: unknown
<220> FEATURE:
<223> OTHER INFORMATION: SB10 (see Fig. 2)

<400> SEQUENCE: 18

Trp Arg Lys Lys Gly Glu Ala Cys Lys Pro Lys Asn Thr Ile Pro Thr
1               5                   10                  15

Val Lys His Gly Gly Gly Ser Ile Met Leu Trp Gly Cys Phe Ala Ala
            20                  25                  30

Gly Gly Thr Gly Ala Leu His Lys Ile Asp Gly Ile Met Arg Lys Glu
        35                  40                  45

Asn Tyr Val Asp Ile Leu Lys Gln His Leu
    50                  55

<210> SEQ ID NO 19
<211> LENGTH: 58
<212> TYPE: PRT
<213> ORGANISM: unknown
<220> FEATURE:
<223> OTHER INFORMATION: Tc1 (see Fig. 2)

<400> SEQUENCE: 19

Arg Arg Pro Val Gly Ser Arg Tyr Ser Pro Lys Tyr Gln Cys Pro Thr
1               5                   10                  15

Val Lys His Gly Gly Gly Ser Val Met Val Trp Gly Cys Phe Thr Ser
            20                  25                  30

Thr Ser Met Gly Pro Leu Arg Arg Ile Gln Ser Ile Met Asp Arg Phe
        35                  40                  45

```
Gln Tyr Glu Asn Ile Phe Glu Thr Thr Met
    50                  55
```

```
<210> SEQ ID NO 20
<211> LENGTH: 58
<212> TYPE: PRT
<213> ORGANISM: unknown
<220> FEATURE:
<223> OTHER INFORMATION: Tcb2 (see Fig. 2)

<400> SEQUENCE: 20
```

```
Arg Arg Pro Val Gly Cys Arg Phe Asp Pro Ser Tyr Gln Leu Gln Thr
 1               5                  10                  15

Val Lys His Gly Gly Gly Ser Val Met Val Trp Gly Cys Phe Ser Gly
            20                  25                  30

Thr Ser Met Asp Pro Leu Arg Arg Ile Asp Ser Ile Met Asp Arg Phe
        35                  40                  45

Val Tyr Glu Asp Ile Leu Glu Asn Thr Met
    50                  55
```

```
<210> SEQ ID NO 21
<211> LENGTH: 58
<212> TYPE: PRT
<213> ORGANISM: unknown
<220> FEATURE:
<223> OTHER INFORMATION: Tcb1 (see Fig. 2)

<400> SEQUENCE: 21
```

```
Arg Arg Pro Ile Gly Ser Arg Tyr Ala Pro Gln Tyr Gln Cys Pro Thr
 1               5                  10                  15

Val Lys His Gly Gly Gly Ser Val Met Val Trp Gly Cys Phe Ser Asp
            20                  25                  30

Thr Ser Met Gly Pro Leu Lys Arg Ile Val Gly Thr Met Asp Arg Tyr
        35                  40                  45

Val Tyr Glu Asp Ile Leu Glu Asn Thr Met
    50                  55
```

```
<210> SEQ ID NO 22
<211> LENGTH: 59
<212> TYPE: PRT
<213> ORGANISM: unknown
<220> FEATURE:
<223> OTHER INFORMATION: Beagle2 (see Fig. 3)

<400> SEQUENCE: 22
```

```
Gly Glu Ser Val His Arg Thr Thr Ile Ser Arg Ala Leu His Lys Val
 1               5                  10                  15

Gly Leu Tyr Gly Arg Val Ala Arg Arg Lys Pro Leu Leu Thr Glu Asn
            20                  25                  30

His Lys Lys Ser His Leu Gln Phe Ala Thr Ser His Val Gly Asp Thr
        35                  40                  45

Ala Asn Thr Trp Lys Lys Val Leu Trp Ser Asp
    50                  55
```

```
<210> SEQ ID NO 23
<211> LENGTH: 59
<212> TYPE: PRT
<213> ORGANISM: unknown
<220> FEATURE:
<223> OTHER INFORMATION: PPTN5 (see Fig. 3)

<400> SEQUENCE: 23
```

Gly Glu Ser Val His Arg Thr Thr Ile Ser Arg Leu Leu His Lys Ser
1               5                   10                  15

Gly Leu Tyr Gly Arg Val Ala Arg Arg Lys Pro Leu Lys Gly Ile
            20                  25                  30

His Lys Lys Ser Arg Leu Glu Phe Ala Arg Ser His Val Gly Asp Thr
        35                  40                  45

Ala Asn Met Trp Lys Lys Val Leu Trp Ser Asp
    50                  55

<210> SEQ ID NO 24
<211> LENGTH: 59
<212> TYPE: PRT
<213> ORGANISM: unknown
<220> FEATURE:
<223> OTHER INFORMATION: Froggy2 (see Fig. 3)

<400> SEQUENCE: 24

Gly Cys Ala Val His Val Thr Thr Ile Ser Arg Ile Leu His Met Ser
1               5                   10                  15

Gly Leu Trp Gly Arg Val Ala Arg Arg Lys Pro Phe Leu Thr Lys Lys
            20                  25                  30

Asn Ile Gln Ala Arg Leu His Phe Ala Asn Thr His Leu Lys Ser Pro
        35                  40                  45

Lys Ser Met Trp Glu Lys Val Leu Trp Ser Asp
    50                  55

<210> SEQ ID NO 25
<211> LENGTH: 59
<212> TYPE: PRT
<213> ORGANISM: unknown
<220> FEATURE:
<223> OTHER INFORMATION: FP (see Fig. 3)

<400> SEQUENCE: 25

Lys Val Ser Val His Ala Ser Thr Ile Arg Lys Arg Leu Gly Lys Asn
1               5                   10                  15

Gly Leu His Gly Arg Val Pro Arg Arg Lys Pro Leu Leu Ser Lys Lys
            20                  25                  30

Asn Ile Lys Ala Arg Leu Asn Phe Ser Thr Thr His Leu Asp Asp Pro
        35                  40                  45

Gln Asp Phe Trp Asp Asn Ile Leu Trp Thr Asp
    50                  55

<210> SEQ ID NO 26
<211> LENGTH: 59
<212> TYPE: PRT
<213> ORGANISM: unknown
<220> FEATURE:
<223> OTHER INFORMATION: XtTXr2 (see Fig. 3)

<400> SEQUENCE: 26

Lys Val Ser Val His Asp Ser Thr Ile Arg Lys Arg Leu Gly Lys Asn
1               5                   10                  15

Gly Leu His Gly Arg Phe Pro Arg Arg Lys Pro Leu Leu Ser Lys Lys
            20                  25                  30

Asn Ile Lys Ala His Leu Asn Phe Ala Lys Lys His Leu Asn Asp Cys
        35                  40                  45

Gln Asp Phe Trp Glu Asn Thr Leu Trp Thr Asp
    50                  55

```
<210> SEQ ID NO 27
<211> LENGTH: 46
<212> TYPE: PRT
<213> ORGANISM: unknown
<220> FEATURE:
<223> OTHER INFORMATION: Jumpy2 (see Fig. 3)

<400> SEQUENCE: 27

Gly Ala Ser Leu Ser Ala Gln Thr Ile Arg Arg His Leu Asn Glu Met
1               5                   10                  15

Thr Gln Arg His Lys Lys Ala Arg Leu Gln Phe Ala Lys Met Tyr Leu
            20                  25                  30

Ser Lys Pro Gln Ser Phe Trp Glu Asn Val Leu Trp Thr Asp
        35                  40                  45

<210> SEQ ID NO 28
<211> LENGTH: 60
<212> TYPE: PRT
<213> ORGANISM: unknown
<220> FEATURE:
<223> OTHER INFORMATION: Maya2 (see Fig. 3)

<400> SEQUENCE: 28

Met Gln Lys Ser Ile Cys Glu Ala Thr Thr Arg Thr Thr Leu Arg Gln
1               5                   10                  15

Met Gly Tyr Asn Ser Arg Arg Pro His Arg Val Pro Leu Ile Ser Thr
            20                  25                  30

Thr Asn Arg Lys Lys Arg Leu Gln Phe Ala Gln Ala Glu Gln Asn Trp
        35                  40                  45

Thr Val Glu Asp Trp Lys Asn Val Ala Trp Ser Asp
    50                  55                  60

<210> SEQ ID NO 29
<211> LENGTH: 60
<212> TYPE: PRT
<213> ORGANISM: unknown
<220> FEATURE:
<223> OTHER INFORMATION: Titof2 (see Fig. 3)

<400> SEQUENCE: 29

Arg Gln Lys Ser Ile Ser Glu Arg Thr Val Arg Pro Thr Leu Arg Gln
1               5                   10                  15

Met Gly Tyr Ser Ser Arg Arg Pro His Arg Val Pro Leu Leu Ser Ala
            20                  25                  30

Lys Asn Arg Lys Leu Arg Leu Gln Phe Ala Gln Ala His Arg Asn Trp
        35                  40                  45

Thr Ile Glu Asp Trp Lys Asn Val Ala Trp Ser Asp
    50                  55                  60

<210> SEQ ID NO 30
<211> LENGTH: 59
<212> TYPE: PRT
<213> ORGANISM: unknown
<220> FEATURE:
<223> OTHER INFORMATION: Minos2 (see Fig. 3)

<400> SEQUENCE: 30

Leu Ala Lys Leu Ser Ser Glu Ser Gly Arg Asp Lys Leu Lys Ser Ile
1               5                   10                  15

Gly Tyr Gly Phe Tyr Lys Ala Lys Glu Lys Pro Leu Leu Thr Leu Arg
            20                  25                  30

Gln Lys Lys Lys Arg Leu Gln Trp Ala Arg Glu Arg Met Ser Trp Thr
```

35                  40                  45

Gln Arg Gln Trp Asp Thr Ile Ile Phe Ser Asp
    50                  55

<210> SEQ ID NO 31
<211> LENGTH: 59
<212> TYPE: PRT
<213> ORGANISM: unknown
<220> FEATURE:
<223> OTHER INFORMATION: Xeminos1 (see Fig. 3)

<400> SEQUENCE: 31

Phe Gln Lys Pro Leu Ser Val Asn Thr Ile His Gly Ala Ile Arg His
1               5                   10                  15

Cys Gln Leu Lys Leu Tyr Ser Ala Lys Lys Pro Phe Leu Ser Lys
            20                  25                  30

Ile His Lys Leu Arg Arg Phe His Trp Ala Arg Asp His Leu Lys Arg
        35                  40                  45

Ser Val Ala Lys Trp Lys Thr Val Leu Trp Ser
    50                  55

<210> SEQ ID NO 32
<211> LENGTH: 60
<212> TYPE: PRT
<213> ORGANISM: unknown
<220> FEATURE:
<223> OTHER INFORMATION: STURGEON (see Fig. 3)

<400> SEQUENCE: 32

Ser Gly Thr Leu Val His Pro Ser Thr Val Arg Ser Leu Val Arg
1               5                   10                  15

Ser Gly Leu His Gly Arg Leu Ala Ala Lys Lys Pro Tyr Leu Arg Arg
            20                  25                  30

Gly Asn Lys Ala Lys Arg Leu Asn Tyr Ala Arg Lys His Arg Asn Trp
        35                  40                  45

Gly Ala Glu Lys Trp Gln Gln Val Leu Trp Thr Asp
    50                  55                  60

<210> SEQ ID NO 33
<211> LENGTH: 59
<212> TYPE: PRT
<213> ORGANISM: unknown
<220> FEATURE:
<223> OTHER INFORMATION: CARMEN (see Fig. 3)

<400> SEQUENCE: 33

Gly Lys Ser Val Ser Leu Ser Thr Val Lys Arg Val Leu Tyr Arg His
1               5                   10                  15

Gly Leu Lys Gly His Ser Ala Arg Lys Lys Pro Leu Leu Gln Lys Lys
            20                  25                  30

His Lys Lys Ala Arg Leu Gln Phe Ala Asn Ala His Arg Asp Lys Asp
        35                  40                  45

Leu Asn Phe Trp Arg His Val Leu Trp Ser Asp
    50                  55

<210> SEQ ID NO 34
<211> LENGTH: 58
<212> TYPE: PRT
<213> ORGANISM: unknown
<220> FEATURE:
<223> OTHER INFORMATION: Tdr1 (see Fig. 3)

```
<400> SEQUENCE: 34

Gly Lys Arg Val Ser Leu Ser Thr Val Lys Arg Val Leu Tyr His Gly
1               5                   10                  15

Leu Lys Gly His Ser Ala Arg Lys Pro Leu Leu Gln Lys His His
            20                  25                  30

Lys Lys Ala Arg Leu Gln Phe Ala Lys Leu His Trp Glu Lys Asp Leu
            35                  40                  45

Cys Phe Trp Arg His Val Leu Trp Ser Asp
            50                  55

<210> SEQ ID NO 35
<211> LENGTH: 59
<212> TYPE: PRT
<213> ORGANISM: unknown
<220> FEATURE:
<223> OTHER INFORMATION: SB10 (see Fig. 3)

<400> SEQUENCE: 35

Gly Thr Lys Val Ser Ile Ser Thr Val Lys Arg Val Leu Tyr Arg His
1               5                   10                  15

Asn Leu Lys Gly Arg Ser Ala Arg Lys Lys Pro Leu Leu Gln Asn Arg
            20                  25                  30

His Lys Lys Ala Arg Leu Arg Phe Ala Thr Ala His Gly Asp Lys Asp
            35                  40                  45

Arg Thr Phe Trp Arg Asn Val Leu Trp Ser Asp
            50                  55

<210> SEQ ID NO 36
<211> LENGTH: 59
<212> TYPE: PRT
<213> ORGANISM: unknown
<220> FEATURE:
<223> OTHER INFORMATION: XTCons2 (see Fig. 3)

<400> SEQUENCE: 36

Gly Thr Thr Val Thr Lys Lys Thr Ile Gly Asn Thr Leu His Arg Asn
1               5                   10                  15

Gly Leu Lys Ser Cys Arg Ala Arg Lys Val Pro Leu Leu Lys Lys Ala
            20                  25                  30

His Val Gln Ala Arg Leu Lys Phe Ala Asn Glu His Leu Asn Asp Ser
            35                  40                  45

Val Ser Asp Trp Glu Lys Val Leu Trp Ser Asp
            50                  55

<210> SEQ ID NO 37
<211> LENGTH: 4
<212> TYPE: PRT
<213> ORGANISM: unknown
<220> FEATURE:
<223> OTHER INFORMATION: SB10 (see Fig. 8)

<400> SEQUENCE: 37

Asp Ala Val Gln
1

<210> SEQ ID NO 38
<211> LENGTH: 4
<212> TYPE: PRT
<213> ORGANISM: unknown
<220> FEATURE:
<223> OTHER INFORMATION: SB10
```

```
<400> SEQUENCE: 38

Asp Asn Gly Pro
1               5
```